(12) United States Patent
Neal et al.

(10) Patent No.: US 12,232,792 B2
(45) Date of Patent: Feb. 25, 2025

(54) DEVICE AND METHOD FOR ELECTROPORATION BASED TREATMENT

(71) Applicants: Virginia Tech Intellectual Properties, Inc., Blacksburg, VA (US);
AngioDynamics, Inc., Latham, NY (US)

(72) Inventors: Robert E. Neal, Richmond, VA (US);
Paulo A. Garcia, Somerville, MA (US);
Rafael V. Davalos, Aptos, CA (US);
Peter Callas, Castro Valley, CA (US)

(73) Assignees: Virginia Tech Intellectual Properties, Inc., Blacksburg, VA (US);
AngioDynamics, Inc., Latham, NY (US)

( * ) Notice: Subject to any disclaimer, the term of this patent is extended or adjusted under 35 U.S.C. 154(b) by 0 days.

(21) Appl. No.: 18/502,967

(22) Filed: Nov. 6, 2023

(65) Prior Publication Data

US 2024/0074804 A1    Mar. 7, 2024

Related U.S. Application Data

(63) Continuation of application No. 16/865,772, filed on May 4, 2020, now abandoned, which is a continuation
(Continued)

(51) Int. Cl.
*A61B 18/00* (2006.01)
*A61B 18/14* (2006.01)
*A61B 90/00* (2016.01)

(52) U.S. Cl.
CPC .......... *A61B 18/00* (2013.01); *A61B 18/1492* (2013.01); *A61B 2018/0022* (2013.01);
(Continued)

(58) Field of Classification Search
CPC ................. A61B 18/1492; A61B 2018/00613
See application file for complete search history.

(56) References Cited

U.S. PATENT DOCUMENTS

| | | | |
|---|---|---|---|
| 1,653,819 | A | 12/1927 | Northcott |
| 3,730,238 | A | 5/1973 | Butler |

(Continued)

FOREIGN PATENT DOCUMENTS

| | | | |
|---|---|---|---|
| AU | 7656800 | A | 4/2001 |
| AU | 2002315095 | A1 | 12/2002 |

(Continued)

OTHER PUBLICATIONS

Pending Application No. PCT/US23/15118, Invitation to Pay Additional Fees dated May 17, 2023, 3 pages.
(Continued)

*Primary Examiner* — Michael W Kahelin
(74) *Attorney, Agent, or Firm* — New River Valley IP Law, P.C.; Michele L. Mayberry; Ashley M. Gates

(57) ABSTRACT

The present invention relates to medical devices and methods for treating a lesion such as a vascular stenosis using non-thermal irreversible electroporation (NTIRE). Embodiments of the present invention provide a balloon catheter type NTIRE device for treating a target lesion comprising a plurality of electrodes positioned along the balloon that are electrically independent from each other so as to be individually selectable in order to more precisely treat an asymmetrical lesion in which the lesion extends only partially around the vessel.

19 Claims, 16 Drawing Sheets

ELECTRIC FIELD, V/cm

Related U.S. Application Data of application No. 13/550,307, filed on Jul. 16, 2012, now Pat. No. 10,702,326.

(60) Provisional application No. 61/508,251, filed on Jul. 15, 2011.

(52) U.S. Cl.
CPC ............... *A61B 2018/00613* (2013.01); *A61B 2018/00767* (2013.01); *A61B 2018/00875* (2013.01); *A61B 2018/1467* (2013.01); *A61B 2090/3925* (2016.02); *A61B 2090/3966* (2016.02)

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,903,707 A | 2/1990 | Knute et al. |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| D329,496 S | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran et al. |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,425,752 A | 6/1995 | Nguyen |
| 5,439,440 A | 8/1995 | Hofmann |
| 5,458,625 A | 10/1995 | Kendall |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| D376,652 S | 12/1996 | Hunt et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| D380,272 S | 6/1997 | Partika et al. |
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,718,246 A | 2/1998 | Vona |
| 5,720,921 A | 2/1998 | Meserol |
| 5,735,847 A | 4/1998 | Gough et al. |
| 5,752,939 A | 5/1998 | Makoto |

(56) References Cited

U.S. PATENT DOCUMENTS

| | | |
|---|---|---|
| 5,778,894 A | 7/1998 | Dorogi et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,865,787 A | 2/1999 | Shapland et al. |
| 5,868,708 A | 2/1999 | Hart et al. |
| 5,873,849 A | 2/1999 | Bernard |
| 5,904,648 A | 5/1999 | Arndt et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler et al. |
| 5,957,919 A | 9/1999 | Laufer |
| 5,957,963 A | 9/1999 | Dobak, III |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,096,035 A | 8/2000 | Sodhi et al. |
| 6,102,885 A | 8/2000 | Bass |
| 6,106,521 A | 8/2000 | Blewett et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,120,493 A | 9/2000 | Hofmann |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,135,999 A | 10/2000 | Fanton et al. |
| 6,139,545 A | 10/2000 | Utley et al. |
| 6,150,148 A | 11/2000 | Nanda et al. |
| 6,159,163 A | 12/2000 | Strauss et al. |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 | 6/2001 | Cosman |
| D445,198 S | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| D450,391 S | 11/2001 | Hunt et al. |
| 6,312,428 B1 | 11/2001 | Eggers et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,347,247 B1 | 2/2002 | Dev et al. |
| 6,349,233 B1 | 2/2002 | Adams |
| 6,351,674 B2 | 2/2002 | Silverstone |
| 6,375,634 B1 | 4/2002 | Carroll |
| 6,387,671 B1 | 5/2002 | Rubinsky et al. |
| 6,398,779 B1 | 6/2002 | Buysse et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,428,802 B1 | 8/2002 | Atala |
| 6,443,952 B1 | 9/2002 | Mulier et al. |
| 6,463,331 B1 | 10/2002 | Edwards |
| 6,470,211 B1 | 10/2002 | Ideker et al. |
| 6,478,793 B1 | 11/2002 | Cosman et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood et al. |
| 6,503,248 B1 | 1/2003 | Levine |
| 6,506,189 B1 | 1/2003 | Rittman et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |
| 6,537,976 B1 | 3/2003 | Gupta |
| 6,540,695 B1 | 4/2003 | Burbank et al. |
| 6,558,378 B2 | 5/2003 | Sherman et al. |
| 6,562,604 B2 | 5/2003 | Rubinsky et al. |
| 6,569,162 B2 | 5/2003 | He |
| 6,575,969 B1 | 6/2003 | Rittman et al. |
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Mccormick et al. |

(56) References Cited

U.S. PATENT DOCUMENTS

| | | |
|---|---|---|
| 6,616,657 B2 | 9/2003 | Simpson et al. |
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | Mcgovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,733,516 B2 | 5/2004 | Simons et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 | 3/2005 | Dev et al. |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | McGuckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chornenky et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 | 2/2010 | Long |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chornenky et al. |
| D630,321 S | 1/2011 | Hamilton |
| D631,154 S | 1/2011 | Hamilton |
| 7,871,406 B2 | 1/2011 | Nields et al. |
| RE42,277 E | 4/2011 | Jaafar et al. |
| 7,918,852 B2 | 4/2011 | Tullis et al. |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,048,067 B2 | 11/2011 | Davalos et al. |
| 8,055,323 B2 | 11/2011 | Sawyer |
| RE43,009 E | 12/2011 | Chornenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |
| 8,251,986 B2 | 8/2012 | Chornenky et al. |
| 8,267,927 B2 | 9/2012 | Dalal et al. |
| 8,267,936 B2 | 9/2012 | Hushka et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,361,066 B2 | 1/2013 | Long et al. |
| D677,798 S | 3/2013 | Hart et al. |
| 8,425,455 B2 | 4/2013 | Nentwick |
| 8,425,505 B2 | 4/2013 | Long |
| 8,454,594 B2 | 6/2013 | Demarais et al. |
| 8,465,464 B2 | 6/2013 | Travis et al. |
| 8,465,484 B2 | 6/2013 | Davalos et al. |
| 8,506,564 B2 | 8/2013 | Long et al. |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |
| 8,632,534 B2 | 1/2014 | Pearson et al. |
| 8,634,929 B2 | 1/2014 | Chornenky et al. |
| 8,647,338 B2 | 2/2014 | Chornenky et al. |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |
| 8,903,488 B2 | 12/2014 | Callas et al. |
| 8,906,006 B2 | 12/2014 | Chornenky et al. |
| 8,926,606 B2 | 1/2015 | Davalos et al. |
| 8,958,888 B2 | 2/2015 | Chornenky et al. |

(56) References Cited

U.S. PATENT DOCUMENTS

| | | |
|---|---|---|
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |
| 9,149,331 B2 | 10/2015 | Deem et al. |
| 9,173,704 B2 | 11/2015 | Hobbs et al. |
| 9,198,733 B2 | 12/2015 | Neal, II et al. |
| 9,283,051 B2 | 3/2016 | Garcia et al. |
| 9,414,881 B2 | 8/2016 | Callas et al. |
| 9,598,691 B2 | 3/2017 | Davalos |
| 9,700,368 B2 | 7/2017 | Callas et al. |
| 9,764,145 B2 | 9/2017 | Callas et al. |
| 9,867,652 B2 | 1/2018 | Sano et al. |
| 9,943,599 B2 | 4/2018 | Gehl et al. |
| 10,117,701 B2 | 11/2018 | Davalos et al. |
| 10,117,707 B2 | 11/2018 | Garcia et al. |
| 10,154,874 B2 | 12/2018 | Davalos et al. |
| 10,238,447 B2 | 3/2019 | Neal et al. |
| 10,245,098 B2 | 4/2019 | Davalos et al. |
| 10,245,105 B2 | 4/2019 | Davalos et al. |
| 10,272,178 B2 | 4/2019 | Davalos et al. |
| 10,286,108 B2 | 5/2019 | Davalos et al. |
| 10,292,755 B2 | 5/2019 | Davalos et al. |
| 10,448,989 B2 | 10/2019 | Arena et al. |
| 10,470,822 B2 | 11/2019 | Garcia et al. |
| 10,471,254 B2 | 11/2019 | Sano et al. |
| 10,537,379 B2 | 1/2020 | Sano et al. |
| 10,694,972 B2 | 6/2020 | Davalos et al. |
| 10,702,326 B2 * | 7/2020 | Neal, II ............... A61B 18/00 |
| 10,828,085 B2 | 11/2020 | Davalos et al. |
| 10,828,086 B2 | 11/2020 | Davalos et al. |
| 10,959,772 B2 | 3/2021 | Davalos et al. |
| 11,254,926 B2 | 2/2022 | Garcia et al. |
| 11,272,979 B2 | 3/2022 | Garcia et al. |
| 11,311,329 B2 | 4/2022 | Davalos et al. |
| 11,382,681 B2 | 7/2022 | Arena et al. |
| 11,406,820 B2 | 8/2022 | Sano et al. |
| 11,453,873 B2 | 9/2022 | Davalos et al. |
| 11,607,271 B2 | 3/2023 | Garcia et al. |
| 11,607,537 B2 | 3/2023 | Latouche et al. |
| 11,638,603 B2 | 5/2023 | Sano et al. |
| 11,655,466 B2 | 5/2023 | Neal et al. |
| 11,737,810 B2 | 8/2023 | Davalos et al. |
| 11,890,046 B2 | 2/2024 | Neal et al. |
| 11,903,690 B2 | 2/2024 | Davalos et al. |
| 11,925,405 B2 | 3/2024 | Davalos et al. |
| 11,950,835 B2 | 4/2024 | O'Brien et al. |
| 11,952,568 B2 | 4/2024 | Neal, II et al. |
| 11,974,800 B2 | 5/2024 | Sano et al. |
| 12,059,197 B2 | 8/2024 | Davalos et al. |
| 12,173,280 B2 | 12/2024 | Neal, II et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077627 A1 | 6/2002 | Johnson et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0104318 A1 | 8/2002 | Jaafar et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Edward |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0153960 A1 | 8/2003 | Chornenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1 | 11/2003 | Heil et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193042 A1 | 9/2004 | Scampini et al. |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0004507 A1 | 1/2005 | Schroeppel et al. |
| 2005/0010209 A1 | 1/2005 | Lee et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0043726 A1 | 2/2005 | McHale et al. |
| 2005/0048651 A1 | 3/2005 | Ryttsen et al. |
| 2005/0049541 A1 | 3/2005 | Behar et al. |
| 2005/0061322 A1 | 3/2005 | Freitag |
| 2005/0066974 A1 | 3/2005 | Fields et al. |
| 2005/0112141 A1 | 5/2005 | Terman |

(56) References Cited

U.S. PATENT DOCUMENTS

| | | |
|---|---|---|
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0197619 A1 | 9/2005 | Rule et al. |
| 2005/0261672 A1 | 11/2005 | Deem et al. |
| 2005/0267407 A1 | 12/2005 | Goldman |
| 2005/0282284 A1 | 12/2005 | Rubinsky et al. |
| 2005/0283149 A1 | 12/2005 | Thorne et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett et al. |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky et al. |
| 2006/0224188 A1 | 10/2006 | Libbus et al. |
| 2006/0235474 A1 | 10/2006 | Demarais |
| 2006/0247619 A1 | 11/2006 | Kaplan et al. |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0276710 A1 | 12/2006 | Krishnan |
| 2006/0278241 A1 | 12/2006 | Ruano |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016125 A1 | 1/2007 | Wong et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129720 A1 | 6/2007 | Demarais et al. |
| 2007/0129760 A1 | 6/2007 | Demarais et al. |
| 2007/0151848 A1 | 7/2007 | Novak et al. |
| 2007/0156135 A1 | 7/2007 | Rubinsky et al. |
| 2007/0191889 A1 | 8/2007 | Lang |
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bornzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0009102 A1 | 1/2008 | Yang et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0065062 A1 | 3/2008 | Leung et al. |
| 2008/0071262 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel et al. |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198231 A1 | 8/2009 | Esser et al. |
| 2009/0228001 A1 | 9/2009 | Pacey |
| 2009/0247933 A1 | 10/2009 | Maor et al. |
| 2009/0248012 A1* | 10/2009 | Maor ................. A61B 18/14 606/41 |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326346 A1 | 12/2009 | Kracker et al. |
| 2009/0326366 A1 | 12/2009 | Krieg |
| 2009/0326436 A1 | 12/2009 | Rubinsky et al. |
| 2009/0326570 A1 | 12/2009 | Brown |

(56) References Cited

U.S. PATENT DOCUMENTS

| | | |
|---|---|---|
| 2010/0004623 A1 | 1/2010 | Hamilton, Jr. et al. |
| 2010/0006441 A1 | 1/2010 | Renaud et al. |
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0147701 A1 | 6/2010 | Field |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1* | 10/2010 | Davalos .............. A61B 18/1477 600/407 |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0092973 A1 | 4/2011 | Nuccitelli et al. |
| 2011/0106221 A1 | 5/2011 | Neal et al. |
| 2011/0112531 A1 | 5/2011 | Landis et al. |
| 2011/0118727 A1 | 5/2011 | Fish et al. |
| 2011/0118732 A1 | 5/2011 | Rubinsky et al. |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Aljuri et al. |
| 2011/0166499 A1 | 7/2011 | Demarais et al. |
| 2011/0176037 A1 | 7/2011 | Benkley |
| 2011/0202053 A1 | 8/2011 | Moss et al. |
| 2011/0217730 A1 | 9/2011 | Gazit et al. |
| 2011/0251607 A1 | 10/2011 | Kruecker et al. |
| 2011/0301587 A1 | 12/2011 | Deem et al. |
| 2012/0034131 A1 | 2/2012 | Rubinsky et al. |
| 2012/0059255 A1 | 3/2012 | Paul et al. |
| 2012/0071870 A1 | 3/2012 | Salahieh et al. |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0090646 A1 | 4/2012 | Tanaka et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0226218 A1 | 9/2012 | Phillips et al. |
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303020 A1 | 11/2012 | Chornenky et al. |
| 2012/0310236 A1 | 12/2012 | Placek et al. |
| 2013/0023871 A1 | 1/2013 | Collins |
| 2013/0030239 A1 | 1/2013 | Weyh et al. |
| 2013/0090646 A1 | 4/2013 | Moss et al. |
| 2013/0108667 A1 | 5/2013 | Soikum et al. |
| 2013/0110106 A1 | 5/2013 | Richardson |
| 2013/0184702 A1 | 7/2013 | Neal et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0218157 A1 | 8/2013 | Callas et al. |
| 2013/0253415 A1 | 9/2013 | Sano et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0017218 A1 | 1/2014 | Scott et al. |
| 2014/0039489 A1 | 2/2014 | Davalos et al. |
| 2014/0046322 A1 | 2/2014 | Callas et al. |
| 2014/0066913 A1 | 3/2014 | Sherman |
| 2014/0081255 A1 | 3/2014 | Johnson et al. |
| 2014/0088578 A1 | 3/2014 | Rubinsky et al. |
| 2014/0121663 A1 | 5/2014 | Pearson et al. |
| 2014/0121728 A1 | 5/2014 | Dhillon et al. |
| 2014/0163551 A1 | 6/2014 | Maor et al. |
| 2014/0207133 A1 | 7/2014 | Model et al. |
| 2014/0276748 A1 | 9/2014 | Ku et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0152504 A1 | 6/2015 | Lin |
| 2015/0164584 A1 | 6/2015 | Davalos et al. |
| 2015/0173824 A1 | 6/2015 | Davalos et al. |
| 2015/0201996 A1 | 7/2015 | Rubinsky et al. |
| 2015/0265349 A1 | 9/2015 | Moss et al. |
| 2015/0289923 A1 | 10/2015 | Davalos et al. |
| 2015/0320478 A1 | 11/2015 | Cosman, Jr. et al. |
| 2015/0320488 A1 | 11/2015 | Moshe et al. |
| 2015/0320999 A1 | 11/2015 | Nuccitelli et al. |
| 2015/0327944 A1 | 11/2015 | Robert et al. |
| 2016/0022957 A1 | 1/2016 | Hobbs et al. |
| 2016/0066977 A1 | 3/2016 | Neal et al. |
| 2016/0074114 A1 | 3/2016 | Pearson et al. |
| 2016/0113708 A1 | 4/2016 | Moss et al. |
| 2016/0143698 A1 | 5/2016 | Garcia et al. |
| 2016/0235470 A1 | 8/2016 | Callas et al. |
| 2016/0287313 A1 | 10/2016 | Rubinsky et al. |
| 2016/0287314 A1 | 10/2016 | Arena et al. |
| 2016/0338758 A9 | 11/2016 | Davalos et al. |
| 2016/0338761 A1 | 11/2016 | Chornenky et al. |
| 2016/0354142 A1 | 12/2016 | Pearson et al. |
| 2016/0367310 A1 | 12/2016 | Onik et al. |
| 2017/0035501 A1 | 2/2017 | Chornenky et al. |
| 2017/0086713 A1 | 3/2017 | Pushpala et al. |
| 2017/0189579 A1 | 7/2017 | Davalos |
| 2017/0209620 A1 | 7/2017 | Davalos et al. |
| 2017/0266438 A1 | 9/2017 | Sano |
| 2017/0319851 A1 | 11/2017 | Athos et al. |
| 2017/0348525 A1 | 12/2017 | Sano et al. |
| 2017/0360326 A1 | 12/2017 | Davalos |
| 2018/0028260 A1 | 2/2018 | Onik et al. |
| 2018/0036529 A1 | 2/2018 | Jaroszeski et al. |
| 2018/0071014 A1 | 3/2018 | Neal et al. |
| 2018/0125565 A1 | 5/2018 | Sano et al. |
| 2018/0132922 A1 | 5/2018 | Neal et al. |
| 2018/0161086 A1 | 6/2018 | Davalos et al. |
| 2018/0177543 A1 | 6/2018 | You et al. |
| 2018/0198218 A1 | 7/2018 | Regan et al. |
| 2019/0023804 A1 | 1/2019 | Onik et al. |
| 2019/0029749 A1 | 1/2019 | Garcia et al. |
| 2019/0046255 A1 | 2/2019 | Davalos et al. |
| 2019/0069945 A1 | 3/2019 | Davalos et al. |
| 2019/0076528 A1 | 3/2019 | Soden et al. |
| 2019/0083169 A1 | 3/2019 | Single et al. |
| 2019/0133671 A1 | 5/2019 | Davalos et al. |
| 2019/0175248 A1 | 6/2019 | Neal et al. |
| 2019/0175260 A1 | 6/2019 | Davalos et al. |
| 2019/0223938 A1 | 7/2019 | Arena et al. |
| 2019/0232048 A1 | 8/2019 | Latouche et al. |
| 2019/0233809 A1 | 8/2019 | Neal et al. |
| 2019/0256839 A1 | 8/2019 | Neal et al. |

(56) References Cited

U.S. PATENT DOCUMENTS

| | | | |
|---|---|---|---|
| 2019/0282294 A1 | 9/2019 | Davalos et al. |
| 2019/0328445 A1 | 10/2019 | Sano et al. |
| 2019/0351224 A1 | 11/2019 | Sano et al. |
| 2019/0376055 A1 | 12/2019 | Davalos et al. |
| 2020/0046432 A1 | 2/2020 | Garcia et al. |
| 2020/0046967 A1 | 2/2020 | Ivey et al. |
| 2020/0093541 A9 | 3/2020 | Neal et al. |
| 2020/0197073 A1 | 6/2020 | Sano et al. |
| 2020/0260987 A1 | 8/2020 | Davalos et al. |
| 2020/0323576 A1 | 10/2020 | Neal et al. |
| 2020/0405373 A1 | 12/2020 | O'Brien et al. |
| 2021/0022795 A1 | 1/2021 | Davalos et al. |
| 2021/0023362 A1 | 1/2021 | Lorenzo et al. |
| 2021/0052882 A1 | 2/2021 | Wasson et al. |
| 2021/0113265 A1 | 4/2021 | D'Agostino et al. |
| 2021/0137410 A1 | 5/2021 | O'Brien et al. |
| 2021/0186600 A1 | 6/2021 | Davalos et al. |
| 2021/0361341 A1 | 11/2021 | Neal et al. |
| 2021/0393312 A1 | 12/2021 | Davalos et al. |
| 2022/0151688 A1 | 5/2022 | Garcia et al. |
| 2022/0161027 A1 | 5/2022 | Aycock et al. |
| 2022/0290183 A1 | 9/2022 | Davalos et al. |
| 2022/0362549 A1 | 11/2022 | Sano et al. |
| 2023/0157759 A1 | 5/2023 | Garcia et al. |
| 2023/0212551 A1 | 7/2023 | Neal et al. |
| 2023/0248414 A1 | 8/2023 | Sano et al. |
| 2023/0355293 A1 | 11/2023 | Davalos et al. |
| 2023/0355968 A1 | 11/2023 | Davalos et al. |
| 2024/0008911 A1 | 1/2024 | Davalos et al. |
| 2024/0074804 A1 | 3/2024 | Neal et al. |
| 2024/0173063 A1 | 5/2024 | Neal, II et al. |
| 2024/0268878 A1 | 8/2024 | Davalos et al. |
| 2024/0277245 A1 | 8/2024 | Davalos et al. |
| 2024/0299076 A1 | 9/2024 | O'Brien et al. |
| 2025/0000569 A1 | 1/2025 | Davalos et al. |

FOREIGN PATENT DOCUMENTS

| | | |
|---|---|---|
| AU | 2003227960 A1 | 12/2003 |
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| AU | 2009243079 A2 | 1/2011 |
| AU | 2015259303 A1 | 11/2016 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2722296 A1 | 11/2009 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| CN | 106715682 A | 5/2017 |
| CN | 112807074 A | 5/2021 |
| DE | 863111 | 1/1953 |
| DE | 4000893 A1 | 7/1991 |
| DE | 60038026 | 2/2009 |
| EP | 0218275 A1 | 4/1987 |
| EP | 0339501 A2 | 11/1989 |
| EP | 0378132 A | 7/1990 |
| EP | 0533511 A1 | 3/1993 |
| EP | 0998235 A1 | 5/2000 |
| EP | 0528891 B1 | 7/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2280741 A1 | 2/2011 |
| EP | 2381829 A1 | 11/2011 |
| EP | 2413833 A1 | 2/2012 |
| EP | 2488251 A2 | 8/2012 |
| EP | 2642937 A2 | 10/2013 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |
| EP | 3143124 A1 | 3/2017 |
| EP | 3852868 A1 | 7/2021 |
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2011137025 | 7/2011 |
| JP | 2011137025 | 7/2011 |
| JP | 2012510332 A | 5/2012 |
| JP | 2012515018 A | 7/2012 |
| JP | 2012521863 A | 9/2012 |
| JP | 2014501574 A | 1/2014 |
| JP | 2017518805 A | 7/2017 |
| JP | 6594901 B2 | 10/2019 |
| JP | 2019193668 A | 11/2019 |
| JP | 7051188 B2 | 4/2022 |
| KR | 101034682 A | 5/2011 |
| WO | 9104014 | 4/1991 |
| WO | 9634571 | 11/1996 |
| WO | 9639531 A | 12/1996 |
| WO | 9810745 | 3/1998 |
| WO | 9814238 A | 4/1998 |
| WO | 9901076 | 1/1999 |
| WO | 9904710 | 2/1999 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |
| WO | 0148153 A | 7/2001 |
| WO | 2001048153 A1 | 7/2001 |
| WO | 0170114 A1 | 9/2001 |
| WO | 0181533 A | 11/2001 |
| WO | 02078527 A | 10/2002 |
| WO | 02089686 A | 11/2002 |
| WO | 02100459 A | 12/2002 |
| WO | 2003020144 A1 | 3/2003 |
| WO | 2003047684 A2 | 6/2003 |
| WO | 03099382 A | 12/2003 |
| WO | 2004037341 A2 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |

(56) References Cited

FOREIGN PATENT DOCUMENTS

| WO | 2007067938 A2 | 6/2007 |
|---|---|---|
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2008063195 A1 | 5/2008 |
| WO | 2008034103 A3 | 11/2008 |
| WO | 2009046176 A1 | 4/2009 |
| WO | 2007137303 | 7/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010080974 A1 | 7/2010 |
| WO | 2010117806 A1 | 10/2010 |
| WO | 2010118387 A | 10/2010 |
| WO | 2010132472 A1 | 11/2010 |
| WO | 2010151277 A | 12/2010 |
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012071526 A | 5/2012 |
| WO | 2012071526 A2 | 5/2012 |
| WO | 2012088149 A | 6/2012 |
| WO | 2015175570 A1 | 11/2015 |
| WO | 2016100325 A1 | 6/2016 |
| WO | 2016164930 A1 | 10/2016 |
| WO | 2017117418 A1 | 7/2017 |
| WO | 2020061192 A1 | 3/2020 |
| WO | 2022066768 A1 | 3/2022 |
| WO | 2023172773 A1 | 9/2023 |
| WO | 2024081749 A2 | 4/2024 |

OTHER PUBLICATIONS

Phillips, M., Maor, E. & Rubinsky, B. Non-Thermal Irreversible Electroporation for Tissue Decellularization. J. Biomech. Eng, doi:10.1115/1.4001882 (2010).

Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.

Polajžer, T. et al., "Cancellation effect is present in high-frequency reversible and irreversible electroporation," Bioelectrochemistry, vol. 132, 2020, 11 pages.

Polak et al., "On the Electroporation Thresholds of Lipid Bilayers: Molecular Dynamics Simulation Investigations." The Journal of Membrane Biology, vol. 246, pp. 843-850 (2013).

Pucihar et al., "Numerical determination of transmembrane voltage induced on irregularly shaped cells." Annals of Biomedical Engineering, vol. 34, pp. 642-652 (2006).

Qiao et al. Electrical properties of breast cancer cells from impedance measurement of cell suspensions, 2010, Journal of Physics, 224, 1-4 (2010).

Rajagopal, V. and S.G. Rockson, Coronary restenosis: a review of mechanisms and management, The American Journal of Medicine, 2003, 115(7): p. 547-553.

Reberšek, M. and D. Miklavčič, "Advantages and Disadvantages of Different Concepts of Electroporation Pulse Generation," Automatika 52(2011) 1, 12-19.

Reilly, J. P. et al., "Sensory Effects of Transient Electrical Stimulation-Evaluation with a Neuroelectric Model," IEEE Trans. Biomed. Eng., vol. BME-32, No. 12, 1001-1011, 1985, 11 pages.

Ringel-Scaia, V. M. et al., High-frequency irreversible electroporation is an effective tumor ablation strategy that induces immunologic cell death and promotes systemic anti-tumor immunity. EBioMedicine, 2019, 44, 112-125.

Rogers, W. R. et al., "Strength-duration curve an electrically excitable tissue extended down to near 1 nanosecond," IEEE Trans. Plasma Sci., vol. 32, No. 4 II, 1587-1599, 2004, 13 pages.

Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.

Ron et al., "Cell-based screening for membranal and cytoplasmatic markers using dielectric spectroscopy." Biophysical chemistry, 135 (2008) pp. 59-68.

Rossmeisl et al., "Pathology of non-thermal irreversible electroporation (N-TIRE)-induced ablation of the canine brain." Journal of Veterinary Science vol. 14, pp. 433-440 (2013).

Rossmeisl, "New Treatment Modalities for Brain Tumors in Dogs and Cats." Veterinary Clinics of North America: Small Animal Practice 44, pp. 1013-1038 (2014).

Rossmeisl, John H. et al. Safety and feasibility of the NanoKnife system for irreversible electroporation ablative treatment of canine spontaneous intracranial gliomas. J. Neurosurgery 123.4 (2015): 1008-1025.

Rubinsky et al., "Optimal Parameters for the Destruction of Prostate Cancer Using Irreversible Electroporation." The Journal of Urology, 180 (2008) pp. 2668-2674.

Rubinsky, B., "Irreversible Electroporation in Medicine", Technology in Cancer Research and Treatment, vol. 6, No. 4, Aug. 1, 2007, pp. 255-259.

Rubinsky, B., ed, Cryosurgery. Annu Rev. Biomed. Eng. vol. 2 2000. 157-187.

Rubinsky, B., et al., "Irreversible Electroporation: A New Ablation Modality—Clinical Implications" Technol. Cancer Res. Treatment 6(1), 37-48 (2007).

Rubinsky, L. et al., "Electrolytic Effects During Tissue Ablation by Electroporation," Technol. Cancer Res. Treat., vol. 15, No. 5, NP95-103, 2016, 9 pages.

Sabuncu et al., "Dielectrophoretic separation of mouse melanoma clones." Biomicrofluidics, vol. 4, 7 pages (2010).

SAI Infusion Technologies, "Rabbit Ear Vein Catheters", https://www.sai-infusion.com/products/rabbit-ear-catheters, Aug. 10, 2017 webpage printout, 5 pages.

Salford, L.G., et al., "A new brain tumour therapy combining bleomycin with in vivo electropermeabilization", Biochem. Biophys. Res. Commun., 194(2): 938-943 (1993).

Salmanzadeh et al., "Investigating dielectric properties of different stages of syngeneic murine ovarian cancer cells" Biomicrofluidics 7, 011809 (2013), 12 pages.

Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).

Salmanzadeh et al., "Sphingolipid Metabolites Modulate Dielectric Characteristics of Cells in a Mouse Ovarian Cancer Progression Model." Integr. Biol., 5(6), pp. 843-852 (2013).

Sanchez, B., G. Vandersteen, R. Bragos, and J. Schoukens, "Basics of broadband impedance spectroscopy measurements using periodic excitations," Measurement Science and Technology, vol. 23, No. 10, p. 105501, 2012.

Sanchez, B., G. Vandersteen, R. Bragos, and J. Schoukens, "Optimal multisine excitation design for broadband electrical impedance spectroscopy," Measurement Science and Technology, vol. 22, No. 11, p. 115601, 2011.

Sano et al., "Contactless Dielectrophoretic Spectroscopy: Examination of the Dielectric Properties of Cells Found in Blood." Electrophoresis, 32, pp. 3164-3171, 2011.

Sano et al., "In-vitro bipolar nano- and microsecond electro-pulse bursts for irreversible electroporation therapies." Bioelectrochemistry vol. 100, pp. 69-79 (2014).

Sano et al., "Modeling and Development of a Low Frequency Contactless Dielectrophoresis (cDEP) Platform to Sort Cancer Cells from Dilute Whole Blood Samples." Biosensors & Bioelectronics, 8 pages (2011).

Sano, M. B. et al., "Burst and continuous high frequency irreversible electroporation protocols evaluated in a 3D tumor model," Phys. Med. Biol., vol. 63, No. 13, 2018, 17 pages.

(56) References Cited

OTHER PUBLICATIONS

Sano, M. B. et al., "Reduction of Muscle Contractions During Irreversible Electroporation Therapy Using High-Frequency Bursts of Alternating Polarity Pulses: A Laboratory Investigation in an Ex Vivo Swine Model," J. Vasc. Interv. Radiol., vol. 29, No. 6, 893-898.e4, Jun. 2018, 18 pages.
Sano, M. B., et al., "Towards the creation of decellularized organ constructs using irreversible electroporation and active mechanical perfusion", Biomedical Engineering Online, Biomed Central Ltd, London, GB, vol. 9, No. 1, Dec. 10, 2010, p. 83.
Saur et al., "CXCR4 expression increases liver and lung metastasis in a mouse model of pancreatic cancer." Gastroenterology, vol. 129, pp. 1237-1250 (2005).
Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.
Schoenbach et al., "Intracellular effect of ultrashort electrical pulses." Bioelectromagnetics, 22 (2001) pp. 440-448.
Seibert et al., "Clonal variation of MCF-7 breast cancer cells in vitro and in athymic nude mice." Cancer Research, vol. 43, pp. 2223-2239 (1983).
Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).
Sel, D. et al. Sequential finite element model of tissue electropermeabilization. IEEE Transactions on Biomedical Engineering 52, 816-827, doi: 10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol., 37(1): 43-8, 2003.
Shao, Qi et al. Engineering T cell response to cancer antigens by choice of focal therapeutic conditions, International Journal of Hyperthermia, 2019, DOI: 10.1080/02656736.2018.1539253.
Sharma, A., et al., "Review on Thermal Energy Storage with Phase Change Materials and Applications", Renewable Sustainable Energy Rev. 13(2), 318-345 (2009).
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, S., et al., Percutaneous ethanol injection therapy for hepatocellular carcinoma: results in 146 patients. AJR, 1993, 160: p. 1023-8.
Szot et al., "3D in vitro bioengineered tumors based on collagen I hydrogels." Biomaterials vol. 32, pp. 7905-7912 (2011).
Mulhall et al., "Cancer, pre-cancer and normal oral cells distinguished by dielectrophoresis." Analytical and Bioanalytical Chemistry, vol. 401, pp. 2455-2463 (2011).
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.
Naslund, Michael J., Transurethral Needle Ablation of the Prostate, Urology, vol. 50, No. 2, Aug. 1997.
Neal II et al., "A Case Report on the Successful Treatment of a Large Soft-Tissue Sarcoma with Irreversible Electroporation," Journal of Clinical Oncology, 29, pp. 1-6, 2011.
Neal II et al., "Experimental Characterization and Numerical Modeling of Tissue Electrical Conductivity during Pulsed Electric Fields for Irreversible Electroporation Treatment Planning," Biomedical Engineering, IEEE Transactions on Biomedical Engineering, vol. 59, pp. 1076-1085, 2012.
Neal II, R. E. et al. In Vitro and Numerical Support for Combinatorial Irreversible Electroporation and Electrochemotherapy Glioma Treatment. Annals of Biomedical Engineering, Oct. 29, 2013, 13 pages.
Neal II, R. E., et al., "Successful Treatment of a Large Soft Tissue Sarcoma with Irreversible Electroporation", Journal of Clinical Oncology, 29:13, e372-e377 (2011).
Neal II, R.E., et al., "Treatment of breast cancer through the application of irreversible electroporation using a novel minimally invasive single needle electrode." Breast Cancer Research and Treatment, 2010. 123(1): p. 295-301.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neal RE II, et al. (2013) Improved Local and Systemic Anti-Tumor Efficacy for Irreversible Electroporation in Immunocompetent versus Immunodeficient Mice. PLoS ONE 8(5): e64559. https://doi.org/10.1371/journal.pone.0064559.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).
Neumann, et al., Gene Transfer into Mouse Lyoma Cells by Electroporation in High Electric Fields, J. Embo., vol. 1, No. 7, pp. 841-845, 1982.
Neumann, et al., Permeability Changes Induced by Electric Impulses in Vesicular Membranes, J. Membrane Biol., vol. 10, pp. 279-290, 1972.
Nikolova, B., et al., "Treatment of Melanoma by Electroporation of Bacillus Calmette-Guerin". Biotechnology & Biotechnological Equipment, 25(3): p. 2522-2524 (2011).
Nuccitelli, R., et al., "A new pulsed electric field therapy for melanoma disrupts the tumor's blood supply and causes complete remission without recurrence", Int J Cancer, 125(2): p. 438-45 (2009).
O'Brien et al., "Investigation of the Alamar Blue (resazurin) fluorescent dye for the assessment of mammalian cell cytotoxicity." European Journal of Biochemistry, vol. 267, pp. 5421-5426 (2000).
O'Brien, T. J. et al., "Effects of internal electrode cooling on irreversible electroporation using a perfused organ model," Int. J. Hyperth., vol. 35, No. 1, pp. 44-55, 2018.
Okino, et al., Effects of High-Voltage Electrical Impulse and an Anticancer Drug on In Vivo Growing Tumors, Japanese Journal of Cancer Research, vol. 78, pp. 1319-1321, 1987.
Onik, et al., Sonographic Monitoring of Hepatic Cryosurgery in an Experimental Animal Model, AJR American J. of Roentgenology, vol. 144, pp. 1043-1047, May 1985.
Onik, et al., Ultrasonic Characteristics of Frozen Liver, Cryobiology, vol. 21, pp. 321-328, 1984.
Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.
Onik, G., P. Mikus, and B. Rubinsky, "Irreversible electroporation: implications for prostate ablation." Technol Cancer Res Treat, 2007. 6(4): p. 295-300.
Organ, L.W., Electrophysiological principles of radiofrequency lesion making, Apply. Neurophysiol., 1976. 39: p. 69-76.
Ott, H. C., et al., "Perfusion-decellularized matrix: using nature's platform to engineer a bioartificial heart", Nature Medicine, Nature Publishing Group, New York, Ny, US, vol. 14, No. 2, Feb. 1, 2008, pp. 213-221.
Pakhomova, O. N., Gregory, B., Semenov I., and Pakhomov, A. G., BBA—Biomembr., 2014, 1838, 2547-2554.
Partridge, B. R. et al., "High-Frequency Irreversible Electroporation for treatment of Primary Liver Cancer: A Proof-of-Principle Study in Canine Hepatocellular Carcinoma," J. Vasc. Interv. Radiol., vol. 31, No. 3, 482-491.e4, Mar. 2020, 19 pages.

(56) References Cited

OTHER PUBLICATIONS

Paszek et al., "Tensional homeostasis and the malignant phenotype." Cancer Cell, vol. 8, pp. 241-254 (2005).
Patent No. JP 7051188, Notice of Reasons for Revocation dated Jan. 30, 2023 (3 pages) with English translation (5 pages).
Patent No. JP 7051188, Opposition dated Jul. 4, 2022 (16 pages) with English translation (13 pages).
Patent No. JP 7051188, Response to Jan. 30, 2023 Notice of Reasons for Revocation, dated Apr. 27, 2023 (9 pages) with English translation (10 pages).
Patent No. JP 7051188, Response to Opposition dated Aug. 22, 2023 (21 pages) with English translation (25 pages).
Pavselj, N. et al. The course of tissue permeabilization studied on a mathematical model of a subcutaneous tumor in small animals. IEEE Trans Biomed Eng 52, 1373-1381 (2005).
Pavselj, N., et al., "A numerical model of skin electroporation as a method to enhance gene transfection in skin. 11th Mediterranean Conference on Medical and Biological Engineering and Computing", vols. 1 and 2, 16(1-2): p. 597-601 (2007).
PCT Application No. PCT/2011/062067, International Preliminary Report on Patentability dated May 28, 2013.
PCT Application No. PCT/2011/066239, International Preliminary Report on Patentability dated Jun. 25, 2013.
PCT Application No. PCT/US09/62806, International Search Report (Jan. 19, 2010), Written Opinion (Jan. 19, 2010), and International Preliminary Report on Patentability (Jan. 4, 2010), 15 pgs.
PCT Application No. PCT/US10/53077, International Search Report (Aug. 2, 2011), Written Opinion (Aug. 2, 2011), and International Preliminary Report on Patentability (Apr. 17, 2012).
PCT Application No. PCT/US15/30429, International Search Report and Written Opinion dated Oct. 16, 2015, 19 pages.
PCT Application No. PCT/US15/30429, International Report on Patentability dated Nov. 15, 2016.
PCT Application No. PCT/US15/65792, International Search Report (Feb. 9, 2016), Written Opinion (Feb. 9, 2016), and International Preliminary Report on Patentability (Jun. 20, 2017), 15 pages.
PCT Application No. PCT/US19/51731, International Preliminary Report on Patentability dated Mar. 23, 2021, 13 pages.
PCT Application No. PCT/US19/51731, International Search Report and Written Opinion dated Feb. 20, 2020, 19 pgs.
PCT Application No. PCT/US19/51731, Invitation to Pay Additional Search Fees dated Oct. 28, 2019, 2 pgs.
PCT Application No. PCT/US2004/043477, International Search Report (Aug. 26, 2005), Written Opinion (Aug. 26, 2005), and International Preliminary Report on Patentability (Jun. 26, 2006).
PCT Application No. PCT/US2009/042100, International Search Report (Jul. 9, 2009), Written Opinion (Jul. 9, 2009), and International Preliminary Report on Patentability (Nov. 2, 2010).
PCT Application No. PCT/US2010/029243, International Search Report, 4 pgs, (Jul. 30, 2010), Written Opinion, 7 pgs, (Jul. 30, 2010), and International Preliminary Report on Patentability, 8 pgs, (Oct. 4, 2011).
PCT Application No. PCT/US2010/030629, International Search Report (Jul. 15, 2010), Written Opinion (Jul. 15, 2010), and International Preliminary Report on Patentability (Oct. 11, 2011).
PCT Application No. PCT/US2011/062067, International Search Report and Written Opinion dated Jul. 25, 2012.
PCT Application No. PCT/US2011/066239, International Search Report (Aug. 22, 2012), and Written Opinion (Aug. 22, 2012).
Cosman, E. R. et al., "Electric and Thermal Field Effects in Tissue Around Radiofrequency Electrodes," Pain Med., vol. 6, No. 6, 405-424, 2005, 20 pages.
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.
Creason, S. C., J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, No. 1, pp. 9-46, 1973.
Crowley, Electrical Breakdown of Biomolecular Lipid Membranes as an Electromechanical Instability, Biophysical Journal, vol. 13, pp. 711-724, 1973.
Dahl et al., "Nuclear shape, mechanics, and mechanotransduction." Circulation Research vol. 102, pp. 1307-1318 (2008).
Daskalov, I., et al, "Exploring new instrumentation parameters for electrochemotherapy—Attacking tumors with bursts of biphasic pulses instead of single pulses", IEEE Eng Med Biol Mag, 18(1): p. 62-66 (1999).
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos et al., "Electrical impedance tomography for imaging tissue electroporation," IEEE Transactions on Biomedical Engineering, 51, pp. 761-767, 2004.
Davalos et al., "Theoretical analysis of the thermal effects during in vivo tissue electroporation." Bioelectrochemistry, vol. 61(1-2): pp. 99-107, 2003.
Davalos, et al., A Feasibility Study for Electrical Impedance Tomography as a Means to Monitor T issue Electroporation for Molecular Medicine, IEEE Transactions on Biomedical Engineering, vol. 49, No. 4, Apr. 2002.
Davalos, et al., Tissue Ablation with Irreversible Electroporation, Annals of Biomedical Engineering, vol. 33, No. 2, p. 223-231, Feb. 2005.
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
De Senneville, B. D. et al., "MR thermometry for monitoring tumor ablation," European radiology, vol. 17, No. 9, pp. 2401-2410, 2007.
De Vuyst, E., et al., "In situ bipolar Electroporation for localized cell loading with reporter dyes and investigating gap junctional coupling", Biophysical Journal, 94(2): p. 469-479 (2008).
Dean, Nonviral Gene Transfer to Skeletal, Smooth, and Cardiac Muscle in Living Animals, Am J. Physiol Cell Physiol 289: 233-245, 2005.
Demirbas, M. F., "Thermal Energy Storage and Phase Change Materials: An Overview" Energy Sources Part B 1(1), 85-95 (2006).
Dev, et al., Medical Applications of Electroporation, IEEE Transactions of Plasma Science, vol. 28, No. 1, pp. 206-223, Feb. 2000.
Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd et al., "Mathematical modeling of irreversible electroporation for treatment planning." Technology in Cancer Research and Treatment, vol. 6, No. 4, pp. 275-286 (2007).
Edd, J., et al., In-Vivo Results of a New Focal Tissue Ablation Technique: Irreversible Electroporaton, IEEE Trans. Biomed. Eng. 53 (2006) p. 1409-1415.
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).

(56) References Cited

OTHER PUBLICATIONS

Eppich et al., "Pulsed electric fields for selection of hematopoietic cells and depletion of tumor cell contaminants." Nature Biotechnology 18, pp. 882-887 (2000).
Erez, et al., Controlled Destruction and Temperature Distributions in Biological Tissues Subjected to Monoactive Electrocoagulation, Transactions of the ASME: Journal of Mechanical Design, vol. 102, Feb. 1980.
Ermolina et al., "Study of normal and malignant white blood cells by time domain dielectric spectroscopy." IEEE Transactions on Dielectrics and Electrical Insulation, 8 (2001) pp. 253-261.
Esser, A.T., et al., "Towards solid tumor treatment by irreversible electroporation: intrinsic redistribution of fields and currents in tissue". Technol Cancer Res Treat, 6(4): p. 261-74 (2007).
Esser, A.T., et al., "Towards Solid Tumor Treatment by Nanosecond Pulsed Electric Fields", Technology in Cancer Research & Treatment, 8(4): p. 289-306 (2009).
Faroja, M., et al., "Irreversible Electroporation Ablation: Is the entire Damage Nonthermal?", Radiology, 266(2), 462-470 (2013).
Fischbach et al., "Engineering tumors with 3D scaffolds." Nat Meth 4, pp. 855-860 (2007).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Foster RS, "High-intensity focused ultrasound in the treatment of prostatic disease", European Urology, 1993, vol. 23 Suppl 1, pp. 29-33.
Foster, R.S., et al., Production of Prostatic Lesions in Canines Using Transrectally Administered High-Intensity Focused Ultrasound. Eur. Urol., 1993; 23: 330-336.
Fox, et al., Sampling Conductivity Images via MCMC, Mathematics Department, Auckland University, New Zealand, May 1997.
Frandsen, S. K., H. Gissel, P. Hojman, T. Tramm, J. Eriksen, and J. Gehl. Direct therapeutic applications of calcium electroporation to effectively induce tumor necrosis. Cancer Res. 72:1336-41, 2012.
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Garcia et al., "Irreversible electroporation (IRE) to treat brain cancer." ASME Summer Bioengineering Conference, Marco Island, FL, Jun. 25-29, 2008, 2 pages.
Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.
Garcia, et al., "A Parametric Study Delineating Irreversible Electroporation from Thermal Damage Based on a Minimally Invasive Intracranial Procedure," Biomed Eng Online, vol. 10:34, 22 pages, 2011.
Garcia, P. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).
Garcia, P. et al. Intracranial nonthermal irreversible electroporation: in vivo analysis. J Membr Biol 236, 127-136 (2010).
Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.

García-Sanchez, T., A. Azan, I. Leray, J. Rosell-Ferrer, R. Bragos, and L. M. Mir, "Interpulse multifrequency electrical impedance measurements during electroporation of adherent differentiated myotubes," Bioelectrochemistry, vol. 105, pp. 123-135, 2015.
Gascoyne et al., "Membrane changes accompanying the induced differentiation of Friend murine erythroleukemia cells studied by dielectrophoresis." Biochimica et Biophysica Acta (BBA)—Biomembranes, vol. 1149, pp. 119-126 (1993).
Pending U.S. Appl. No. 16/865,031, Preliminary Amendment filed May 1, 2020, 7 pages.
Pending U.S. Appl. No. 16/865,031, Response to May 24, 2023 Final Office Action, dated Jul. 25, 2023, 8 pages.
Pending U.S. Appl. No. 16/865,031, Response to Nov. 28, 2022 Non-Final Office Action, dated Feb. 27, 2023, 10 pages.
Pending U.S. Appl. No. 16/865,031, Second Preliminary Amendment, filed Sep. 17, 2021, 10 pages.
Pending U.S. Appl. No. 16/865,772, Final Office Action dated Aug. 22, 2022, 18 pages.
Pending U.S. Appl. No. 16/865,772, Final Office Action dated Aug. 4, 2023, 19 pages.
Pending U.S. Appl. No. 16/865,772, Non-Final Office Action dated Apr. 11, 2022, 16 pages.
Pending U.S. Appl. No. 16/865,772, Non-Final Office Action dated Jan. 20, 2023, 17 pages.
Pending U.S. Appl. No. 16/865,772, Preliminary Amendment filed May 4, 2020, 6 pages.
Pending U.S. Appl. No. 16/865,772, Response to Apr. 11, 2022 Non-Final Office Action, dated Jul. 11, 2022, 8 pages.
Pending U.S. Appl. No. 16/865,772, Response to Aug. 22, 2022 Final Office Action, dated Dec. 22, 2022, 8 pages.
Pending U.S. Appl. No. 16/865,772, Response to Jan. 20, 2023 Non-Final Office Action, dated Apr. 20, 2023, 8 pages.
Pending U.S. Appl. No. 16/865,772, Second Preliminary Amendment filed Jun. 30, 2020, 4 pages.
Pending U.S. Appl. No. 16/865,772, Third Preliminary Amendment, filed Sep. 17, 2021, 6 pages.
Pending U.S. Appl. No. 16/915,760, Applicant-Initiated Interview Summary dated Aug. 8, 2023, 2 pages.
Pending U.S. Appl. No. 16/915,760, Final Office Action dated Aug. 10, 2023, 9 pages.
Pending U.S. Appl. No. 16/915,760, Final Office Action dated Jun. 2, 2023, 8 pages.
Pending U.S. Appl. No. 16/915,760, Non-Final Office Action dated Jan. 19, 2023, 8 pages.
Pending U.S. Appl. No. 16/915,760, Notice of Allowance dated Nov. 29, 2023, 7 pages.
Pending U.S. Appl. No. 16/915,760, Preliminary Amendment filed Jul. 6, 2020, 5 pages.
Pending U.S. Appl. No. 16/915,760, Response to Aug. 10, 2023 Final Office Action, dated Nov. 10, 2023, 6 pages.
Pending U.S. Appl. No. 16/915,760, Response to Jan. 19, 2023 Non-Final Office Action, dated Apr. 19, 2023, 8 pages.
Pending U.S. Appl. No. 16/915,760, Response to Sep. 20, 2022 Restriction Requirement, filed Nov. 21, 2022, 2 pages.
Pending U.S. Appl. No. 16/915,760, Restriction Requirement dated Sep. 20, 2022, 6 pages.
Pending U.S. Appl. No. 16/938,778, Non-Final Office Action dated Jan. 2, 2024, 12 pages.
Pending U.S. Appl. No. 16/938,778, Response to Oct. 24, 2023 Restriction Requirement, dated Dec. 13, 2023, 3 pages.
Pending U.S. Appl. No. 16/938,778, Restriction Requirement dated Oct. 24, 2023, 6 pages.
Pending U.S. Appl. No. 17/000,049, Non-Final Office Action dated Dec. 11, 2023, 13 pages.
Pending U.S. Appl. No. 17/000,049, Response to Jul. 31, 2023 Restriction Requirement dated Nov. 9, 2023, 8 pages.
Pending U.S. Appl. No. 17/000,049, Restriction Requirement dated Jul. 31, 2023, 6 pages.
Pending U.S. Appl. No. 17/172,731, Final Office Action dated Jul. 12, 2023, 11 pages.
Pending U.S. Appl. No. 17/172,731, Non-Final Office Action dated Feb. 15, 2023, 7 pages.

(56) References Cited

OTHER PUBLICATIONS

Pending U.S. Appl. No. 17/172,731, Non-Final Office Action dated Oct. 31, 2023, 13 pages.
Pending U.S. Appl. No. 17/172,731, Preliminary Amendment, filed Jun. 27, 2022, 9 pages.
Pending U.S. Appl. No. 17/172,731, Preliminary Amendment, filed Sep. 17, 2021, 7 pages.
Pending U.S. Appl. No. 17/172,731, Response to Feb. 15, 2023 Non-Final Office Action, dated May 15, 2023, 8 pages.
Pending U.S. Appl. No. 17/172,731, Response to Jul. 12, 2023 Final Office Action, dated Oct. 12, 2023, 10 pages.
Pending U.S. Appl. No. 17/277,662 Non-Final Office Action dated May 5, 2023, 9 pages.
Pending U.S. Appl. No. 17/277,662 Notice of Allowance dated Oct. 2, 2023, 7 pages.
Pending U.S. Appl. No. 17/277,662 Preliminary Amendment filed Mar. 18, 2021, 8 pages.
Pending U.S. Appl. No. 17/277,662 Response to May 5, 2023 Non-Final Office Action, dated Aug. 7, 2023, 8 pages.
Pending U.S. Appl. No. 17/338,960, Ex Parte Quayle Action dated May 24, 2023, 6 pages.
Pending U.S. Appl. No. 17/338,960, Response to May 24, 2023 Ex Parte Quayle Action, dated Aug. 8, 2023, 6 pages.
Pending U.S. Appl. No. 17/338,960, Response to Notice to File Missing Parts and Amendment, filed Aug. 16, 2021, 7 pages.
Pending U.S. Appl. No. 17/591,992, Preliminary Amendment dated Sep. 20, 2023, 9 pages.
Pending U.S. Appl. No. 18/027,824, Preliminary Amendment dated Mar. 22, 2023, 8 pages.
Pending U.S. Appl. No. 18/100,835, Preliminary Amendment filed Jan. 26, 2023, 8 pages.
Pending U.S. Appl. No. 18/100,835, Second Preliminary Amendment filed Feb. 6, 2023, 6 pages.
Pending U.S. Appl. No. 18/120,158, Preliminary Amendment dated Mar. 13, 2023, 195 pages.
Pending U.S. Appl. No. 18/123,719, Preliminary Amendment dated Jun. 6, 2023, 6 pages.
Kolb, J.F., et al., "Nanosecond pulsed electric field generators for the study of subcellular effects", Bioelectromagnetics, 27(3): p. 172-187 (2006).
Kotnik and Miklavcic, "Theoretical evaluation of voltage inducement on internal membranes of biological cells exposed to electric fields." Biophysical Journal, vol. 90(2), pp. 480-491 (2006).
Kotnik et al., "Sensitivity of transmembrane voltage induced by applied electric fields—A theoretical analysis", Bioelectrochemistry and Bioenergetics, vol. 43, Issue 2, 1997, pp. 285-291.
Kotnik, T. and D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses. Part II. Reduced electrolytic contamination", Bioelectrochemistry, 54(1): p. 91-5 (2001).
Kotnik, T., et al., "Role of pulse shape in cell membrane electropermeabilization", Biochimica Et Biophysica Acta—Biomembranes, 1614(2): p. 193-200 (2003).
Kranjc, M., S. Kranjc, F. Bajd, G. Sersa, I. Sersa, and D. Miklavcic, "Predicting irreversible electroporation-induced tissue damage by means of magnetic resonance electrical impedance tomography," Scientific reports, vol. 7, No. 1, pp. 1-10, 2017.
Labeed et al., "Differences in the biophysical properties of membrane and cytoplasm of apoptotic cells revealed using dielectrophoresis." Biochimica et Biophysica Acta (BBA)—General Subjects, vol. 1760, pp. 922-929 (2006).
Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).
Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.
Laufer et al., "Electrical impedance characterization of normal and cancerous human hepatic tissue." Physiological Measurement, vol. 31, pp. 995-1009 (2010).
Lebar et al., "Inter-pulse interval between rectangular voltage pulses affects electroporation threshold of artificial lipid bilayers." IEEE Transactions on NanoBioscience, vol. 1 (2002) pp. 116-120.
Lee, E. W. et al. Advanced Hepatic Ablation Technique for Creating Complete Cell Death : Irreversible Electroporation. Radiology 255, 426-433, doi:10.1148/radiol.10090337 (2010).
Lee, E.W., et al., "Imaging guided percutaneous irreversible electroporation: ultrasound and immunohistological correlation", Technol Cancer Res Treat 6: 287-294 (2007).
Lee, R. C., D. J. Canaday, and S. M. Hammer. Transient and stable ionic permeabilization of isolated skeletal muscle cells after electrical shock. J. Burn Care Rehabil. 14:528-540, 1993.
Li, W., et al., "The Effects of Irreversible Electroporation (IRE) on Nerves" PloS One, Apr. 2011, 6(4), e18831.
Liu, et al., Measurement of Pharyngeal Transit Time by Electrical Impedance Tomography, Clin. Phys. Physiol. Meas., 1992, vol. 13, Suppl. A, pp. 197-200.
Long, G., et al., "Targeted Tissue Ablation With Nanosecond Pulses". Ieee Transactions on Biomedical Engineering, 58(8) (2011).
Lundqvist, et al., Altering the Biochemical State of Individual Cultured Cells and Organelles with Ultramicroelectrodes, Proc. Natl. Acad. Sci. USA, vol. 95, pp. 10356-10360, Sep. 1998.
Lurquin, Gene Transfer by Electroporation, Molecular Biotechnology, vol. 7, 1997.
Lynn, et al., A New Method for the Generation and Use of Focused Ultrasound in Experimental Biology, The Journal of General Physiology, vol. 26, 179-193, 1942.
Maček Lebar and Miklavčič, "Cell electropermeabilization to small molecules in vitro: control by pulse parameters." Radiology and Oncology, vol. 35(3), pp. 193-202 (2001).
Macherey, O. et al., "Asymmetric pulses in cochlear implants: Effects of pulse shape, polarity, and rate," JARO—J. Assoc. Res. Otolaryngol., vol. 7, No. 3, 253-266, 2006, 14 pages.
Mahmood, F., et al., "Diffusion-Weighted MRI for Verification of Electroporation-Based Treatments", Journal of Membrane Biology 240: 131-138 (2011).
Mahnic-Kalamiza, et al., "Educational application for visualization and analysis of electric field strength in multiple electrode electroporation," BMC Med Educ, vol. 12:102, 13 pages, 2012.
Malpica et al., "Grading ovarian serous carcinoma using a two-tier system." The American Journal of Surgical Pathology, vol. 28, pp. 496-504 (2004).
Maor et al., The Effect of Irreversible Electroporation on Blood Vessels, Tech. in Cancer Res. and Treatment, vol. 6, No. 4, Aug. 2007, pp. 307-312.
Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.
Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.
Marszalek et al., "Schwan equation and transmembrane potential induced by alternating electric field." Biophysical Journal, vol. 58, pp. 1053-1058 (1990).
Martin, n.R.C.G., et al., "Irreversible electroporation therapy in the management of locally advanced pancreatic adenocarcinoma." Journal of the American College of Surgeons, 2012. 215(3): p. 361-369.
Martinsen, O. G. and Grimnes, S., Bioimpedance and bioelectricity basics. Academic press, 2011.
Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.
McIntyre, C. C. et al., "Modeling the excitability of mammalian nerve fibers: Influence of afterpotentials on the recovery cycle," J. Neurophysiol., vol. 87, No. 2, 995-1006, 2002, 12 pages.

(56) References Cited

OTHER PUBLICATIONS

McNeal, D. R., "Analysis of a Model for Excitation of Myelinated Nerve," IEEE Trans. Biomed. Eng., vol. BME-23, No. 4, 329-337, 1976, 9 pages.

Mercadal, B. et al., "Avoiding nerve stimulation in irreversible electroporation: A numerical modeling study," Phys. Med. Biol., vol. 62, No. 20, 8060-8079, 2017, 28 pages.

Mercadal, Borja et al. "Dynamics of Cell Death After Conventional IRE and H-FIRE Treatments", Annals of Biomedical Engineering, vol. 48, No. 5, 2020, p. 1451-1462.

Miklavčič, D. et al., "The effect of high frequency electric pulses on muscle contractions and antitumor efficiency in vivo for a potential use in clinical electrochemotherapy," Bioelectrochemistry, vol. 65, 121-128, 2004, 8 pages.

Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.

Miklavčič, et al., The Importance of Electric Field Distribution for Effective in Vivo Electroporation of Tissues, Biophysical Journal, vol. 74, May 1998, pp. 2152-2158.

Miller, L., et al., Cancer cells ablation with irreversible electroporation, Technology in Cancer Research and Treatment 4 (2005) 699-706.

Min, M., A. Giannitsis, R. Land, B. Cahill, U. Pliquett, T. Nacke, D. Frense, G. Gastrock, and D. Beckmann, "Comparison of rectangular wave excitations in broad band impedance spectroscopy for microfluidic applications," in World Congress on Medical Physics and Biomedical Engineering, Sep. 7-12, 2009, Munich, Germany. Springer, 2009, pp. 85-88.

Min, M., U. Pliquett, T. Nacke, A. Barthel, P. Annus, and R. Land, "Broadband excitation for short-time impedance spectroscopy," Physiological measurement, vol. 29, No. 6, p. S185, 2008.

Mir et al., "Mechanisms of Electrochemotherapy" Advanced Drug Delivery Reviews 35:107-118 (1999).

Mir, et al., Effective Treatment of Cutaneous and Subcutaneous Malignant Tumours by Electrochemotherapy, British Journal of Cancer, vol. 77, No. 12, pp. 2336-2342, 1998.

Mir, et al., Electrochemotherapy Potentiation of Antitumour Effect of Bleomycin by Local Electric Pulses, European Journal of Cancer, vol. 27, No. 1, pp. 68-72, 1991.

Mir, et al., Electrochemotherapy, a Novel Antitumor Treatment: First Clinical Trial, C.R. Acad. Sci. Paris, Ser. III, vol. 313, pp. 613-618, 1991.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, L.M., et al., Electric Pulse-Mediated Gene Delivery to Various Animal Tissues, in Advances in Genetics, Academic Press, 2005, p. 83-114.

Mir, Therapeutic Perspectives of In Vivo Cell Electropermeabilization, Bioelectrochemistry, vol. 53, pp. 1-10, 2000.

Vernier, P.T., et al., "Nanoelectropulse-driven membrane perturbation and small molecule permeabilization", Bmc Cell Biology, 7 (2006).

Vidamed, Inc., Transurethral Needle Ablation (TUNA): Highlights from Worldwide Clinical Studies, Vidamed's Office TUNA System, 2001.

Vižintin, A. et al., "Effect of interphase and interpulse delay in high-frequency irreversible electroporation pulses on cell survival, membrane permeabilization and electrode material release," Bioelectrochemistry, vol. 134, Aug. 2020, 14 pages.

Voyer, D., A. Silve, L. M. Mir, R. Scorretti, and C. Poignard, "Dynamical modeling of tissue electroporation," Bioelectrochemistry, vol. 119, pp. 98-110, 2018.

Wandel, A. et al. "Optimizing Irreversible Electroporation Ablation with a Bipolar Electrode," Journal of Vascular and Interventional Radiology, vol. 27, Issue 9, 1441-1450.e2, 2016.

Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.

Weaver et al., "A brief overview of electroporation pulse strength-duration space: A region where additional intracellular effects are expected." Bioelectrochemistry vol. 87, pp. 236-243 (2012).

Weaver, Electroporation: A General Phenomenon for Manipulating Cells and Tissues, Journal of Cellular Biochemistry, 51: 426-435, 1993.

Weaver, et al., Theory of Electroporation: A Review, Bioelectrochemistry and Bioenergetics, vol. 41, pp. 136-160, 1996.

Weaver, J. C., Electroporation of biological membranes from multicellular to nano scales, IEEE Trns. Dielectr. Electr. Insul. 10, 754-768 (2003).

Weaver, J.C., "Electroporation of cells and tissues", IEEE Transactions on Plasma Science, 28(1): p. 24-33 (2000).

Weisstein: Cassini Ovals. From MathWorld—A. Wolfram Web Resource; Apr. 30, 2010; http://mathworld.wolfram.com/ (updated May 18, 2011).

Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/s00270-014-0905-2.

Yang et al., "Dielectric properties of human leukocyte subpopulations determined by electrorotation as a cell separation criterion." Biophysical Journal, vol. 76, pp. 3307-3314 (1999).

Yao et al., "Study of transmembrane potentials of inner and outer membranes induced by pulsed-electric-field model and simulation." IEEE Trans Plasma Sci, 2007. 35(5): p. 1541-1549.

Yarmush, M. L. et al., "Electroporation-Based Technologies for Medicine: Principles, Applications, and Challenges," Annu. Rev. Biomed. Eng., vol. 16, No. 1, 295-320, 2014, 29 pages.

Zhang, Y., et al., MR imaging to assess immediate response to irreversible electroporation for targeted ablation of liver tissues: preclinical feasibility studies in a rodent model. Radiology, 2010. 256(2): p. 424-32.

Zhao, J. et al. "Irreversible electroporation reverses resistance to immune checkpoint blockade in pancreatic cancer", Nature Communications (2019) 10:899, 14 pages.

Zhao, Y. et al., "Characterization of conductivity changes during high-frequency irreversible electroporation for treatment planning," IEEE Transactions on Biomedical Engineering, vol. 65, No. 8, pp. 1810-1819, 2017.

Zimmermann, et al., Dielectric Breakdown of Cell Membranes, Biophysical Journal, vol. 14, No. 11, pp. 881-899, 1974.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.

Gauger, et al., A Study of Dielectric Membrane Breakdown in the Fucus Egg, J. Membrane Biol., vol. 48, No. 3, pp. 249-264, 1979.

Gawad, S., T. Sun, N. G. Green, and H. Morgan, "Impedance spectroscopy using maximum length sequences: Application to single cell analysis," Review of Scientific Instruments, vol. 78, No. 5, p. 054301, 2007.

Gehl, et al., In Vivo Electroporation of Skeletal Muscle: Threshold, Efficacy and Relation to Electric Field Distribution, Biochimica et Biphysica Acta 1428, 1999, pp. 233-240.

Gençer, et al., Electrical Impedance Tomography: Induced-Current Imaging Achieved with a Multiple Coil System, IEEE Transactions on Biomedical Engineering, vol. 43, No. 2, Feb. 1996.

Gilbert, et al., Novel Electrode Designs for Electrochemotherapy, Biochimica et Biophysica Acta 1334, 1997, pp. 9-14.

Gilbert, et al., The Use of Ultrasound Imaging for Monitoring Cryosurgery, Proceedings 6th Annual Conference, IEEE Engineering in Medicine and Biology, 107-111, 1984.

(56) References Cited

OTHER PUBLICATIONS

Gilbert, T. W., et al., "Decellularization of tissues and organs", Biomaterials, Elsevier Science Publishers, Barking, GB, vol. 27, No. 19, Jul. 1, 2006, pp. 3675-3683.
Gimsa et al., "Dielectric spectroscopy of single human erythrocytes at physiological ionic strength: dispersion of the cytoplasm." Biophysical Journal, vol. 71, pp. 495-506 (1996).
Glidewell, et al., The Use of Magnetic Resonance Imaging Data and the Inclusion of Anisotropic Regions in Electrical Impedance Tomography, Biomed, Sci. Instrum. 1993; 29: 251-7.
Golberg, A. and Rubinsky, B., "A statistical model for multidimensional irreversible electroporation cell death in tissue." Biomed Eng Online, 9, 13 pages, 2010.
Gothelf, et al., Electrochemotherapy: Results of Cancer Treatment Using Enhanced Delivery of Bleomycin by Electroporation, Cancer Treatment Reviews 2003: 29: 371-387.
Gowrishankar T.R., et al., "Microdosimetry for conventional and supra-electroporation in cells with organelles". Biochem Biophys Res Commun, 341(4): p. 1266-76 (2006).
Granot, Y., A. Ivorra, E. Maor, and B. Rubinsky, "In vivo imaging of irreversible electroporation by means of electrical impedance tomography," Physics in Medicine & Biology, vol. 54, No. 16, p. 4927, 2009.
Griffiths, et al., A Dual-Frequency Electrical Impedance Tomography System, Phys. Med. Biol., 1989, vol. 34, No. 10, pp. 1465-1476.
Griffiths, The Importance of Phase Measurement in Electrical Impedance Tomography, Phys. Med. Biol., 1987, vol. 32, No. 11, pp. 1435-1444.
Griffiths, Tissue Spectroscopy with Electrical Impedance Tomography: Computer Simulations, IEEE Transactions on Biomedical Engineering, vol. 42, No. 9, Sep. 1995.
Groen, M. H. A. et al., "In Vivo Analysis of the Origin and Characteristics of Gaseous Microemboli during Catheter-Mediated Irreversible Electroporation," Europace, 2021, 23(1), 139-146.
Guenther, E. et al., "Electrical breakdown in tissue electroporation," Biochem. Biophys. Res. Commun., vol. 467, No. 4, 736-741, Nov. 2015, 15 pages.
Gumerov, et al., The Dipole Approximation Method and Its Coupling with the Regular Boundary Element Method for Efficient Electrical Impedance Tomography, Boundary Element Technology XIII, 1999.
Hapala, Breaking the Barrier: Methods for Reversible Permeabilization of Cellular Membranes, Critical Reviews in Biotechnology, 17(2): 105-122, 1997.
Helczynska et al., "Hypoxia promotes a dedifferentiated phenotype in ductal breast carcinoma in situ." Cancer Research, vol. 63, pp. 1441-1444 (2003).
Heller, et al., Clinical Applications of Electrochemotherapy, Advanced Drug Delivery Reviews, vol. 35, pp. 119-129, 1999.
Hjouj, M. et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. iii114.
Hjouj, M., et al., "MRI Study on Reversible and Irreversible Electroporation Induced Blood Brain Barrier Disruption", PLOS ONE, Aug. 2012, 7:8, e42817.
Ho, et al., Electroporation of Cell Membranes: A Review, Critical Reviews in Biotechnology, 16(4): 349-362, 1996.
Hoejholt, K. L. et al. Calcium electroporation and electrochemotherapy for cancer treatment: Importance of cell membrane composition investigated by lipidomics, calorimetry and in vitro efficacy. Scientific Reports (Mar. 18, 2019) 9:4758, p. 1-12.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.

Hu, Q., et al., "Simulations of transient membrane behavior in cells subjected to a high-intensity ultrashort electric pulse", Physical Review E, 71(3) (2005).
Huang, et al., Micro-Electroporation: Improving the Efficiency and Understanding of Electrical Permeabilization of Cells, Biomedical Microdevices, vol. 2, pp. 145-150, 1999.
Hughes, et al., An Analysis of Studies Comparing Electrical Impedance Tomography with X-Ray Videofluoroscopy in the Assessment of Swallowing, Physiol. Meas. 15, 1994, pp. A199-A209.
Ibey et al., "Selective cytotoxicity of intense nanosecond-duration electric pulses in mammalian cells." Biochimica Et Biophysica Acta—General Subjects, vol. 1800, pp. 1210-1219 (2010).
Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.
Ivanuša, et al., MRI Macromolecular Contrast Agents as Indicators of Changed Tumor Blood Flow, Radiol. Oncol. 2001; 35(2): 139-47.
Ivey, J. W., E. L. Latouche, M. B. Sano, J. H. Rossmeisl, R. V. Davalos, and S. S. Verbridge, "Targeted cellular ablation based on the morphology of malignant cells," Sci. Rep., vol. 5, pp. 1-17, 2015.
Ivorra et al., "In vivo electric impedance measurements during and after electroporation of rat live." Bioelectrochemistry, vol. 70, pp. 287-295 (2007).
Ivorra et al., "In vivo electrical conductivity measurements during and after tumor electroporation: conductivity changes reflect the treatment outcome." Physics in Medicine and Biology, vol. 54, pp. 5949-5963 (2009).
Ivorra, "Bioimpedance monitoring for physicians: an overview." Biomedical Applications Group, 35 pages (2002).
Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).
Jarm et al., "Antivascular effects of electrochemotherapy: implications in treatment of bleeding metastases." Expert Rev Anticancer Ther. vol. 10, pp. 729-746 (2010).
Jaroszeski, et al., In Vivo Gene Delivery by Electroporation, Advanced Drug Delivery Review, vol. 35, pp. 131-137, 1999.
Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).
Jordan, D.W., et al., "Effect of pulsed, high-power radiofrequency radiation on electroporation of mammalian cells". Ieee Transactions on Plasma Science, 32(4): p. 1573-1578 (2004).
Jossinet et al., Electrical Impedance Endo-Tomography: Imaging Tissue From Inside, IEEE Transactions on Medical Imaging, vol. 21, No. 6, Jun. 2002, pp. 560-565.
Katsuki, S., et al., "Biological effects of narrow band pulsed electric fields", Ieee Transactions on Dielectrics and Electrical Insulation,. 14(3): p. 663-668 (2007).
Kingham et al., "Ablation of perivascular hepatic malignant tumors with irreversible electroporation." Journal of the American College of Surgeons, 2012. 215(3), p. 379-387.
Kinosita and Tsong, "Formation and resealing of pores of controlled sizes in human erythrocyte membrane." Nature, vol. 268 (1977) pp. 438-441.
Kinosita and Tsong, "Voltage-induced pore formation and hemolysis of human erythrocytes." Biochimica et Biophysica Acta (BBA)—Biomembranes, 471 (1977) pp. 227-242.
Kinosita et al., "Electroporation of cell membrane visualized under a pulsed-laser fluorescence microscope." Biophysical Journal, vol. 53, pp. 1015-1019 (1988).
Kinosita, et al., Hemolysis of Human Erythrocytes by a Transient Electric Field, Proc. Natl. Acad. Sci. USA, vol. 74, No. 5, pp. 1923-1927, 1977.
Kirson et al., "Alternating electric fields arrest cell proliferation in animal tumor models and human brain tumors." Proceedings of the National Academy of Sciences vol. 104, pp. 10152-10157 (2007).
Pending U.S. Appl. No. 18/130,330, Preliminary Amendment dated Jun. 20, 2023, 8 pages.

(56) References Cited

OTHER PUBLICATIONS

Pending U.S. Appl. No. 18/348,605, Preliminary Amendment dated Oct. 31, 2023, 7 pages.
Pending Application No. 19861489.3 Extended European Search Report dated May 16, 2022 (8 pages).
Pending Application No. 19861489.3 Response to Communication pursuant to Rules 161(2) and 162 EPC, filed Nov. 16, 2021, 7 pages.
Pending Application No. 19861489.3 Response to May 16, 2022 Extended European Search Report, dated Dec. 13, 2022, 136 pages.
Pending Application No. AU 2009243079, First Examination Report, Jan. 24, 2014, 4 pages.
Pending Application No. AU 2009243079, Voluntary Amendment filed Dec. 6, 2010, 35 pages.
Pending Application No. AU 2015259303, Certificate of Grant dated Feb. 10, 2022, 1 page.
Pending Application No. AU 2015259303, First Examination Report dated Oct. 26, 2020, 6 pages.
Pending Application No. AU 2015259303, Notice of Acceptance and Allowed Claims, dated Oct. 15, 2021, 7 pages.
Pending Application No. AU 2015259303, Response to First Examination Report dated Sep. 20, 2021, 126 pages.
Pending Application No. CA 2,722,296 Examination Report dated Apr. 2, 2015, 6 pages.
Pending Application No. CN 201580025135.6 English translation of Apr. 29, 2020 Office action, 7 pages.
Pending Application No. CN 201580025135.6 English translation of Sep. 25, 2019 Office action.
Pending Application No. CN 201580025135.6 Preliminary Amendment filed with application Nov. 14, 2016.
Pending Application No. CN 201580025135.6 Response to Sep. 25, 2019 Office action, filed Feb. 10, 2020, English language version and original document.
Pending Application No. CN 201580025135.6, First Office Action, dated Sep. 25, 2019 (Chinese and English Versions, each 6 pages).
Pending Application No. CN 201580025135.6, Response to First Office Action, Feb. 7, 2020, (Chinese Vrsion, 13 pages, and English Version, 10 pages).
Pending Application No. CN 201580025135.6, Second Office Action, dated Apr. 29, 2020 (Chinese Version, 4 pages, and English Version, 7 pages).
Pending Application No. CN 202011281572.3, Amendment filed Sep. 8, 2021 (16 pages) with English Version of the Amended Claims (7 pages).
Pending Application No. EP 09739678.2 Extended European Search Report dated May 11, 2012, 7 pages.
Pending Application No. EP 09739678.2, Communication pursuant to Rule 94.3, Apr. 16, 2014, 3 pages.
Pending Application No. EP 09739678.2, Office Action dated Apr. 16, 2014, 3 pages.
Pending Application No. EP 09739678.2, Response to Extended European Search Report and Communication pursuant to Rules 70(2) and 70a(2) EPC, dated Dec. 10, 2012.
Pending Application No. EP 10824248.8, Extended Search Report (Jan. 20, 2014), 6 pages.
Pending Application No. EP 10824248.8, Invitation Pursuant to rule 62a(1) EPC (Sep. 25, 2013), 2 pages.
Pending Application No. EP 10824248.8, Communication Pursuant to Rule 70(2) dated Feb. 6, 2014, 1 page.
Pending Application No. EP 10824248.8, Response to Invitation Pursuant to rule 62a(1) EPC (Sep. 25, 2013), Response filed Nov. 18, 2013.
Pending Application No. EP 11842994.3, Communication Pursuant to Rules 70(2) and 70a(2) EPC dated Apr. 28, 2014, 1 page.
Pending Application No. EP 11842994.3, Extended European Search Report dated Apr. 9, 2014, 34 pages.
Pending Application No. EP 15793361.5, Claim amendment filed Jul. 18, 2018, 13 pages.
Pending Application No. EP 15793361.5, Communication Pursuant to Article 94(3) EPC, dated Apr. 4, 2023, 4 pages.
Pending Application No. EP 15793361.5, Communication Pursuant to Article 94(3) EPC, dated May 3, 2021, 4 pages.
Pending Application No. EP 15793361.5, European Search Report dated Dec. 4, 2017, 9 pages.
Pending Application No. EP 15793361.5, Response to Apr. 4, 2023 Communication Pursuant to Article 94(3) EPC, dated Oct. 16, 2023, 13 pages.
Pending Application No. EP 15793361.5, Response to May 3, 2021 Communication Pursuant to Article 94(3) EPC, dated Nov. 12, 2021, 12 pages.
Pending Application No. JP 2013-541050, Voluntary Amendment filed Oct. 29, 2013, 4 pages (with English Version of the Claims, 2 pages).
Pending Application No. JP 2016-567747 Amendment filed Jul. 18, 2019, 7 pgs.
Pending Application No. JP 2016-567747 English translation of amended claims filed Jul. 18, 2019, 6 pgs.
Pending Application No. JP 2016-567747, First Office Action (Translation) dated Feb. 21, 2019, 5 pages.
Pending Application No. JP 2016-567747, First Office Action dated Feb. 21, 2019, 4 pages.
Pending Application No. JP 2016-567747, Decision to Grant with English Version of allowed claims, 9 pages.
Pending Application No. JP 2019-133057, amended claims (English language version) filed Aug. 14, 2019, 5 pages.
Pending Application No. JP 2019-133057, Office Action dated Sep. 1, 2021, 3 pages (and English translation, 4 pages).
Pending Application No. JP 2019-133057, Office Action dated Sep. 14, 2020, 5 pages (and English translation, 6 pages).
Pending Application No. JP 2019-133057, Request for Amendment and Appeal filed Dec. 23, 2021 (8 pages) with English Translation of the Amended Claims (2 pages).
Pending Application No. JP 2019-133057, Request for Appeal and Amended Claims (8 pages) with English translation of amended claims (2 pages) dated Dec. 23, 2021.
Pending Application No. JP 2019-133057, Response to Sep. 14, 2020 Office Action filed Mar. 18, 2021 (6 pages) with English Version of claims and response (5 pages).
Pending Application No. PCT/US21/51551, International Search Report and Written Opinion dated Dec. 29, 2021, 14 pages.
Pending Application No. PCT/US23/15118, International Search Report and Written Opinion dated Jul. 31, 2023, 18 pages.
Arena et al. "High-Frequency Irreversible Electroporation (H-FIRE) for Non-thermal Ablation without Muscle Contraction." Biomed. Eng. Online, vol. 10, 20 pages (2011).
Arena, C. B. et al., "Theoretical Considerations of Tissue Electroporation With High-Frequency Bipolar Pulses," IEEE Trans. Biomed. Eng., vol. 58, No. 5, 1474-1482, 2011, 9 pages.
Arena, C.B., et al., "A three-dimensional in vitro tumor platform for modeling therapeutic irreversible electroporation." Biophysical Journal, 2012.103(9): p. 2033-2042.
Arena, Christopher B., et al., "Towards the development of latent heat storage electrodes for electroporation-based therapies", Applied Physics Letters, 101, 083902 (2012).
Arena, Christopher B., et al., "Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Asami et al., "Dielectric properties of mouse lymphocytes and erythrocytes." Biochimica et Biophysica Acta (BBA)—Molecular Cell Research, 1010 (1989) pp. 49-55.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.
Ball, C., K.R. Thomson, and H. Kavnoudias, "Irreversible electroporation: a new challenge in "out of-operating theater" anesthesia." Anesth Analg, 2010. 110(5): p. 1305-9.
Bancroft, et al., Design of a Flow Perfusion Bioreactor System for Bone Tissue-Engineering Applications, Tissue Engineering, vol. 9, No. 3, 2003, p. 549-554.

(56) References Cited

OTHER PUBLICATIONS

Baptista et al., "The Use of Whole Organ Decellularization for the Generation of a Vascularized Liver Organoid," Heptatology, vol. 53, No. 2, pp. 604-617 (2011).
Barber, Electrical Impedance Tomography Applied Potential Tomography, Advances in Biomedical Engineering, Beneken and Thevenin, eds., IOS Press, pp. 165-173, 1993.
Beebe, S.J., et al., "Diverse effects of nanosecond pulsed electric fields on cells and tissues", DNA and Cell Biology, 22(12): 785-796 (2003).
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Beebe, S.J., et al.,, "Nanosecond, high-intensity pulsed electric fields induce apoptosis in human cells", FASEB J, 17 (9): p. 1493-5 (2003).
Beitel-White, N., S. Bhonsle, R. Martin, and R. V. Davalos, "Electrical characterization of human biological tissue for irreversible electroporation treatments," in 2018 40th Annual International Conference of the IEEE Engineering in Medicine and Biology Society (EMBC). IEEE, 2018, pp. 4170-4173.
Belehradek, J., et al., "Electropermeabilization of Cells in Tissues Assessed by the Qualitative and Quantitative Electroloading of Bleomycin", Biochimica Et Biophysica Acta-Biomembranes, 1190(1): p. 155-163 (1994).
Ben-David, E. et al., "Irreversible Electroporation: Treatment Effect Is Susceptible to Local Environment and Tissue Properties," Radiology, vol. 269, No. 3, 2013, 738-747.
Ben-David, E., et al., "Characterization of Irreversible Electroporation Ablation in In Vivo Procine Liver" Am. J. Roentgenol. 198(1), W62-W68 (2012).
Benz, R., et al. "Reversible electrical breakdown of lipid bilayer membranes: a charge-pulse relaxation study". J Membr Biol, 48(2): p. 181-204 (1979).
Bhonsle, S. et al., "Characterization of Irreversible Electroporation Ablation with a Validated Perfused Organ Model," J. Vasc. Interv. Radiol., vol. 27, No. 12, pp. 1913-1922.e2, 2016.
Bhonsle, S. P. et al., "Mitigation of impedance changes due to electroporation therapy using bursts of high-frequency bipolar pulses," Biomed. Eng. (NY)., vol. 14, No. Suppl 3, 14 pages, 2015.
Bhonsle, S., M. F. Lorenzo, A. Safaai-Jazi, and R. V. Davalos, "Characterization of nonlinearity and dispersion in tissue impedance during high-frequency electroporation," IEEE Transactions on Biomedical Engineering, vol. 65, No. 10, pp. 2190-2201, 2018.
Blad, et al., Impedance Spectra of Tumour Tissue in Comparison with Normal Tissue; a Possible Clinical Application for Electrical Impedance Tomography, Physiol. Meas. 17 (1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Bonakdar, M., E. L. Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, pp. 2674-2684, 2015.
Bondarenko, A. and G. Ragoisha, Eis spectrum analyser (the program is available online at http://www.abc.chemistry.bsu.by/vi/analyser/.
Boone, K., Barber, D. & Brown, B. Review—Imaging with electricity: report of the European Concerted Action on Impedance Tomography. J. Med. Eng. Technol. 21, 201-232 (1997).
Boussetta, N., N. Grimi, N. I. Lebovka, and E. Vorobiev, "Cold" electroporation in potato tissue induced by pulsed electric field, Journal of food engineering, vol. 115, No. 2, pp. 232-236, 2013.

Bower et al., "Irreversible electroporation of the pancreas: definitive local therapy without systemic effects." Journal of surgical oncology, 2011. 104(1): p. 22-28.
BPH Management Strategies: Improving Patient Satisfaction, Urology Times, May 2001, vol. 29, Supplement 1.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Buist et al., "Efficacy of multi-electrode linear irreversible electroporation," Europace, vol. 23, No. 3, pp. 464-468, 2021, 5 pages.
Bulvik, B. E. et al. "Irreversible Electroporation versus Radiofrequency Ablation II: A Comparison of Local and Systemic Effects in a Small Animal Model," Radiology, vol. 280, No. 2, 2016, 413-424.
Butikofer, R. et al., "Electrocutaneous Nerve Stimulation-I: Model and Experiment," IEEE Trans. Biomed. Eng., vol. BME-25, No. 6, 526-531, 1978,6 pages.
Butikofer, R. et al., "Electrocutaneous Nerve Stimulation-II: Stimulus Waveform Selection," IEEE Trans. Biomed. Eng., vol. BME-26, No. 2, 69-75, 1979, abstract only, 2 pages.
Cannon et al., "Safety and early efficacy of irreversible electroporation for hepatic tumors in proximity to vital structures." Journal of Surgical Oncology, 6 pages (2012).
Carpenter A.E. et al., "CellProfiler: image analysis software for identifying and quantifying cell phenotypes." Genome Biol. 2006; 7(10): R100. Published online Oct. 31, 2006, 11 pages.
Castellvi, Q., B. Mercadal, and A. Ivorra, "Assessment of electroporation by electrical impedance methods," in Handbook of electroporation. Springer-Verlag, 2016, pp. 671-690.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Chang, D.C., "Cell Poration and Cell-Fusion Using an Oscillating Electric-Field". Biophysical Journal, 56(4): p. 641-652 (1989).
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Chen, M.T., et al., "Two-dimensional nanosecond electric field mapping based on cell electropermeabilization", PMC Biophys, 2(1):9 (2009).
Clark et al., "The electrical properties of resting and secreting pancreas." The Journal of Physiology, vol. 189, pp. 247-260 (1967).
Coates, C.W.,et al., "The Electrical Discharge of the Electric Eel, Electrophorous Electricus," Zoologica, 1937, 22(1), pp. 1-32.
Cook, et al., ACT3: A High-Speed, High-Precision Electrical Impedance Tomograph, IEEE Transactions on Biomedical Engineering, vol. 41, No. 8, Aug. 1994.
Corovic et al., "Analytical and numerical quantification and comparison of the local electric field in the tissue for different electrode configurations," Biomed Eng Online, 6, 14 pages, 2007.
(Davalos, Rafael V. et al.) Co-pending U.S. Appl. No. 18/404,473, filed Jan. 4, 2024, Specification, Claims, Figures.
Lv, Y. et al. "The Englargement of Ablation Area by Electrolytic Irreversible Electroporation (E-IRE) Using Pulsed Field with Bias DC Field", Annals of Biomedical Engineering, vol. 50, No. 12, Dec. 2022, 10 pages.
Pending U.S. Appl. No. 17/172,731, Response to Oct. 31, 2023 Non-Final Office Action, dated Jan. 31, 2024, 7 pages.
Pending U.S. Appl. No. 17/591,992, Non-Final Office Action dated Feb. 23, 2024, 9 pages.
Pending U.S. Appl. No. 17/591,992, Non-Final Office Action dated Jan. 24, 2024, 7 pages.
Pending U.S. Appl. No. 18/130,330, Second Preliminary Amendment dated Feb. 26, 2024, 3 pages.

(56) References Cited

OTHER PUBLICATIONS

Pending Application No. EP 15793361.5, Communication dated Feb. 8, 2024, 4 pages.
Pending Application No. PCT/US23/76626, Invitation to Pay Additional Fees dated Feb. 21, 2024, 2 pages.
U.S. Appl. No. 14/686,380, file history through Dec. 2023, 265 pages.
U.S. Appl. No. 16/865,772, file history through Aug. 2023, 110 pages.
(Arena, Christopher B. et al.) Co-pending U.S. Appl. No. 15/186,653, filed Jun. 20, 2016, and published as U.S. Publication No. 2016/0287314 on Oct. 6, 2016, Specification, Claims, Figures.
(Arena, Christopher B. et al.) Co-pending U.S. Appl. No. 16/372,520, filed Apr. 2, 2019, which published as 20190223938 on Jul. 25, 2019, Specification, Claims, Figures.
(Arena, Christopher B. et al.) Co-Pending Application No. PCT/US11/66239, filed Dec. 20, 2011, Specification, Claims, Figures.
(Arena, Christopher B. et al.) Co-Pending Application No. U.S. Appl. No. 13/332,133, filed Dec. 20, 2011 and published as U.S. Publication No. 2012/0109122 on May 3, 2012, Specification, Claims, Figures.
(Aycock, Kenneth N. et al.) Co-pending U.S. Appl. No. 17/535,742, filed Nov. 26, 2021, Specification, Claims, and Figures.
(Davalos, Rafael et al.) Co-Pending Application No. PCT/US21/51551, filed Sep. 22, 2021, Specification, Claims, Figures.
(Davalos, Rafael et al.) Co-pending U.S. Appl. No. 10/571,162, filed Oct. 18, 2006 (published as 2007/0043345 on Feb. 22, 2007), Specification, Figures, Claims.
(Davalos, Rafael et al.) Co-Pending U.S. Appl. No. 12/757,901, filed Apr. 9, 2010, Specification, Claims, Figures.
(Davalos, Rafael et al.) Co-Pending Application No. PCT/US04/43477, filed Dec. 21, 2004, Specification, Claims, Figures.
(Davalos, Rafael et al.) Co-Pending Application No. PCT/US23/15118, filed Mar. 13, 2023, Specification, Claims, Figures.
(Davalos, Rafael et al.) Co-Pending Application No. PCT/US23/76626, filed Oct. 11, 2023, Specification, Claims, Figures.
(Davalos, Rafael V. et al.) Co-Pending Application No. PCT/US10/53077, filed Oct. 18, 2010, Specification, Claims, Figures.
(Davalos, Rafael V. et al.) Co-pending U.S. Appl. No. 12/491,151, filed Jun. 24, 2009, and published as U.S. Publication No. 2010/0030211 on Feb. 4, 2010, Specification, Claims, Figures.
(Davalos, Rafael V. et al.) Co-pending U.S. Appl. No. 12/609,779, filed Oct. 30, 2009, and published as U.S. Publication No. 2010/0331758 on Dec. 30, 2010, Specification, Claims, Figures.
(Davalos, Rafael V. et al.) Co-pending U.S. Appl. No. 13/919,640, filed Jun. 17, 2013, and published as U.S. Publication No. 2013/0281968 on Oct. 24, 2013, Specification, Claims, Figures.
(Davalos, Rafael V. et al.) Co-Pending U.S. Appl. No. 14/686,380, filed Apr. 14, 2015 and Published as US 2015/0289923 on Oct. 15, 2015, Specification, Claims, Figures.
(Davalos, Rafael V. et al.) Co-pending U.S. Appl. No. 15/424,335, filed Feb. 3, 2017, and published as U.S. Publication No. 2017/0189579 on Jul. 6, 2017, Specification, Claims, Figures.
(Davalos, Rafael V. et al.) Co-pending U.S. Appl. No. 15/536,333, filed Jun. 15, 2017, and published as U.S. Publication No. 2017/0360326 on Dec. 21, 2017, Specification, Claims, Figures.
(Davalos, Rafael V. et al.) Co-pending U.S. Appl. No. 15/881,414, filed Jan. 26, 2018, and published as U.S. Publication No. 2018/0161086 on Jun. 14, 2018, Specification, Claims, Figures.
(Davalos, Rafael V. et al.) Co-pending U.S. Appl. No. 16/177,745, filed Nov. 1, 2018, and published as U.S. Publication No. 2019/0069945 on Mar. 7, 2019, Specification, Claims, Figures.
(Davalos, Rafael V. et al.) Co-pending U.S. Appl. No. 16/232,962, filed Dec. 26, 2018, and published as U.S. Publication No. 2019/0133671 on May 9, 2019, Specification, Claims, Figures.
(Davalos, Rafael V. et al.) Co-pending U.S. Appl. No. 16/275,429, filed Feb. 14, 2019, which published as 2019/0175260 on Jun. 13, 2019, Specification, Claims, Figures.
(Davalos, Rafael V. et al.) Co-pending U.S. Appl. No. 16/352,759, filed Mar. 13, 2019, Specification, Claims, Figures.
(Davalos, Rafael V. et al.) Co-pending U.S. Appl. No. 16/535,451, filed Aug. 8, 2019, and Published as U.S. Publication No. 2019/0376055 on Dec. 12, 2019, Specification, Claims, Figures.
(Davalos, Rafael V. et al.) Co-pending U.S. Appl. No. 16/865,031, filed May 1, 2020, Specification, Claims, Figures.
(Davalos, Rafael V. et al.) Co-pending U.S. Appl. No. 17/069,359, filed Oct. 13, 2020, Specification, Claims, Drawings.
(Davalos, Rafael V. et al.) Co-pending U.S. Appl. No. 17/172,731, filed Feb. 10, 2021, Specification, Claims, Figures.
(Davalos, Rafael V. et al.) Co-pending U.S. Appl. No. 17/277,662, filed Mar. 18, 2021, Specification, Claims, Figures.
(Davalos, Rafael V. et al.) Co-Pending U.S. Appl. No. 18/027,824, filed Mar. 22, 2023, Specification, Claims, and Figures.
(Davalos, Rafael V. et al.) Co-Pending U.S. Appl. No. 18/130,330, filed Apr. 3, 2023, Specification, Claims, Figures.
(Davalos, Rafael V. et al.) Co-pending U.S. Appl. No. 18/348,605, filed Jul. 7, 2023, Specification, Claims, Drawings.
(Davalos, Rafael V. et al.) Co-pending U.S. Appl. No. 18/402,231, filed Jan. 2, 2024, Specification, Claims, Figures.
(Davalos, Rafael V. et al.) Co-pending Application No. 19861489.3 filed Apr. 16, 2021, Specification, figures (See PCT/US19/51731), and claims (3 pages).
(Davalos, Rafael V. et al.) Co-Pending Application No. AU 2009243079, filed Apr. 29, 2009 (see PCT/US2009/042100 for documents as filed), Specification, Claims, Figures.
(Davalos, Rafael V. et al.) Co-Pending Application No. PCT/US09/62806, filed Oct. 30, 2009, Specification, Claims, Figures.
(Davalos, Rafael V. et al.) Co-Pending Application No. PCT/US10/30629, filed Apr. 9, 2010, Specification, Claims, Figures.
(Davalos, Rafael V. et al.) Co-pending application No. PCT/US19/51731 filed Sep. 18, 2019, Specification, Claims, Figures.
(Davalos, Rafael V. et al.) Co-Pending U.S. Appl. No. 14/017,210, filed Sep. 3, 2013, and published as U.S. Publication No. 2014/0039489 on Feb. 6, 2014, Specification, Claims, Figures.
(Davalos, Rafael V. et al.) Co-Pending U.S. Appl. No. 14/627,046, filed Feb. 20, 2015, and published as U.S. Publication No. 2015/0164584 on Jun. 18, 2015, Specification, Claims, Figures.
(Davalos, Rafael V. et al.) Co-Pending International Application No. PCT/US15/65792, filed Dec. 15, 2015, Specification, Claims, Drawings.
(Davalos, Rafael V.) Co-Pending U.S. Appl. No. 12/432,295, filed Apr. 29, 2009, and published as U. S. Publication No. 2009/0269317-A1 on Oct. 29, 2009, Specification, Figures, Claims.
(Davalos, Rafael V.) Co-pending U.S. Appl. No. 15/423,986, filed Feb. 3, 2017, and published as U.S. Publication No. 2017/0209620 on Jul. 27, 2017, Specification, Claims, Figures.
(Davalos, Rafael V.) Co-Pending Application No. CA 2,722,296, filed Apr. 29, 2009, Amended Claims (7 pages), Specification, Figures (See PCT/US2009/042100 for Specification and figures as filed).
(Davalos, Rafael V.) Co-Pending Application No. EP 09739678.2 filed Apr. 29, 2009, Amended Claims (3 pages), Specification and Figures (See PCT/US2009/042100).
(Davalos, Rafael V.) Co-Pending Application No. PCT/US09/42100, filed Apr. 29, 2009, Specification, Claims, Figures.
(Garcia, Paulo A. et al.) Co-Pending U.S. Appl. No. 14/012,832, filed Aug. 28, 2013, and published as U.S. Publication No. 2013/0345697 on Dec. 26, 2013, Specification, Claims, Figures.
(Garcia, Paulo A. et al.) Co-Pending U.S. Appl. No. 14/558,631, filed Dec. 2, 2014, and published as U.S. Publication No. 2015/0088120 on Mar. 26, 2015, Specification, Claims, Figures.
(Garcia, Paulo A. et al.) Co-Pending U.S. Appl. No. 15/011,752, filed Feb. 1, 2016, and published as U.S. Publication No. 2016/0143698 on May 26, 2016, Specification, Claims, Figures.
(Garcia, Paulo A. et al.) Co-pending U.S. Appl. No. 16/655,845, filed Oct. 17, 2019, Specification, Claims, Figures.
(Garcia, Paulo A. et al.) Co-pending U.S. Appl. No. 18/100,835, filed Jan. 24, 2023, Specification, Claims, Figures.
(Garcia, Paulo A. et al.) Co-pending U.S. Appl. No. 16/152,743, filed Oct. 5, 2018, Specification, Claims, Figures.
(Garcia, Paulo A. et al.) Co-pending U.S. Appl. No. 17/591,992, filed Feb. 3, 2022, Specification, Claims, Figures.

(56) References Cited

OTHER PUBLICATIONS (Latouche, Eduardo et al.) Co-pending U.S. Appl. No. 16/210,771, filed Dec. 5, 2018, and which published as US Patent Publication No. 2019/0232048 on Aug. 1, 2019, Specification, Claims, Figures.
(Lorenzo, Melvin F. et al.) Co-pending U.S. Appl. No. 16/938,778, filed Jul. 24, 2020, Specification, Claims, Figures.
(Mahajan, Roop L. et al.) Co-pending U.S. Appl. No. 13/958,152, filed Aug. 2, 2013, Specification, Claims, Figures.
(Neal, Robert E. et al.) Co-Pending U.S. Appl. No. 12/906,923, filed Oct. 18, 2010, Specification, Claims, Figures.
(Neal, Robert E. et al.) Co-Pending U.S. Appl. No. 14/808,679, filed Jul. 24, 2015 and Published as U.S. Publication No. 2015/0327944 on Nov. 19, 2015, Specification, Claims, Figures.
(Neal, Robert E. et al.) Co-Pending U.S. Appl. No. 16/375,878, filed Apr. 5, 2019, which published on Aug. 1, 2019 as US 2019-0233809 A1, Specification, Claims, Figures.
(Neal, Robert E. et al.) Co-Pending U.S. Appl. No. 16/404,392, filed May 6, 2019, and published as U.S. Publication No. 2019/0256839 on Aug. 22, 2019, Specification, Claims, Figures.
(Neal, Robert E. et al.) Co-Pending U.S. Appl. No. 16/865,772, filed May 4, 2020, Specification, Claims, Figures.
(Neal, Robert E. et al.) Co-Pending U.S. Appl. No. 18/120,158, filed Mar. 10, 2023, Specification, Claims, Figures.
(Neal, Robert E. et al.) Co-Pending U.S. Appl. No. 13/550,307, filed Jul. 16, 2012, and published as U.S. Publication No. 2013/0184702 on Jul. 18, 2013, Specification, Claims, Figures.
(Neal, Robert E. et al.) Co-Pending U.S. Appl. No. 14/940,863, filed Nov. 13, 2015 and Published as US 2016/0066977 on Mar. 10, 2016, Specification, Claims, Figures.
(Neal, Robert et al.) Co-pending U.S. Appl. No. 16/280,511, filed Feb. 20, 2019, and published as U.S. Publication No. 2019/0175248 on Jun. 13, 2019, Specification, Claims, Figures.
(Neal, Robert et al.) Co-pending U.S. Appl. No. 17/338,960, filed Jun. 4, 2021, Specification, Claims, Figures.
(Neal, Robert et al.) Co-pending U.S. Appl. No. 18/528,051, filed Dec. 4, 2023, Specification, Claims, Figures.
(Neal, Robert et al.) Co-Pending Application No. EP 10824248.8, filed May 9, 2012, Amended Claims (3 pages), Specification and Figures (See PCT/US10/53077).
(O'Brien, Timothy J. et al.) Co-Pending U.S. Appl. No. 16/915,760, filed Jun. 29, 2020, Specification, Claims, Figures.
(O'Brien, Timothy J. et al.) Co-Pending U.S. Appl. No. 17/152,379, filed Jan. 19, 2021, Specification, Claims, Figures.
(Pearson, Robert M. et al.) Co-pending Application No. PCT/US2010/029243, filed Mar. 30, 2010, published as WO 2010/117806 on Oct. 14, 2010, Specification, Claims, Figures.
(Pearson, Robert M. et al.) Co-pending U.S. Appl. No. 12/751,826, filed Mar. 31, 2010 (published as 2010/0250209 on Sep. 30, 2010), Specification, Claims, Figures.
(Pearson, Robert M. et al.) Co-pending U.S. Appl. No. 12/751,854, filed Mar. 31, 2010 (published as 2010/0249771 on Sep. 30, 2010), Specification, Claims, Figures.
(Sano, Michael B. et al.) Co-Pending Application No. PCT/US2015/030429, Filed May 12, 2015, Published on Nov. 19, 2015 as WO 2015/175570, Specification, Claims, Figures.
(Sano, Michael B et al.) Co-Pending U.S. Appl. No. 13/989,175, filed May 23, 2013, and published as U.S. Publication No. 2013/0253415 on Sep. 26, 2013, Specification, Claims, Figures.
(Sano, Michael B. et al.) Co-Pending U.S. Appl. No. 15/310,114, filed Nov. 10, 2016, and published as U.S. Publication No. 2017/0266438 on Sep. 21, 2017, Specification, Claims, Figures.
(Sano, Michael B. et al.) Co-Pending U.S. Appl. No. 15/843,888, filed Dec. 15, 2017, and published as U.S. Publication No. 2018/0125565 on May 10, 2018, Specification, Claims, Figures.
(Sano, Michael B. et al.) Co-Pending U.S. Appl. No. 16/443,351, filed Jun. 17, 2019 (published as 20190328445 on Oct. 31, 2019), Specification, Claims, Figures.
(Sano, Michael B. et al.) Co-Pending U.S. Appl. No. 16/520,901, filed Jul. 24, 2019, and published as U.S. Publication No. 2019/0351224 on Nov. 21, 2019, Specification, Claims, Figures.

(Sano, Michael B. et al.) Co-Pending U.S. Appl. No. 16/747,219, filed Jan. 20, 2020, Specification, Claims, Figures.
(Sano, Michael B. et al.) Co-pending U.S. Appl. No. 17/862,486, filed Jul. 12, 2022, Specification, Claims, Figures.
(Sano, Michael B. et al.) Co-pending U.S. Appl. No. 18/123,719, filed Mar. 20, 2023, Specification, Claims, Figures.
(Sano, Michael B. et al.) Co-Pending Application No. AU 2015259303, filed Oct. 24, 2016, Specification, Figures, Claims.
(Sano, Michael B. et al.) Co-Pending Application No. CN 201580025135.6, filed Nov. 14, 2016, Specification, Claims, Figures (Chinese language and english language versions).
(Sano, Michael B. et al.) Co-Pending Application No. CN 202011281572.3, filed Nov. 16, 2020, Specification, Claims, Figures (Chinese version, 129 pages (see also WO 2015/175570), English Version of claims, 2 pages).
(Sano, Michael B. et al.) Co-Pending Application No. EP 11842994.3, filed Jun. 24, 2013, Amended Claims (18 pages), Specification and Figures (See PCT/US11/62067).
(Sano, Michael B. et al.) Co-Pending Application No. EP 15793361.5, filed Dec. 12, 2016, Specification, Claims, Figures.
(Sano, Michael B. et al.) Co-pending application No. HK 17112121.8, filed Nov. 20, 2017 and published as Publication No. HK1238288 on Apr. 27, 2018, Specification, Claims, Figures (See PCT/US15/30429 for English Version of documents as filed).
(Sano, Michael B. et al.) Co-Pending Application No. JP 2013-541050, filed May 22, 2013, Claims, Specification, and Figures (See PCT/US11/62067 for English Version).
(Sano, Michael B. et al.) Co-Pending Application No. JP 2016-567747, filed Nov. 10, 2016, Specification, Claims, Figures (see PCT/US15/30429 for English Version of documents as filed).
(Sano, Michael B. et al.) Co-Pending Application No. JP 2019-133057 filed Jul. 18, 2019, 155 pgs, Specification, Claims, Figures (See PCT/US15/30429 for English Version of documents as filed).
(Sano, Michael et al.) Co-Pending Application No. PCT/US11/62067, filed Nov. 23, 2011, Specification, Claims, Figures.
(Wasson, Elisa M. et al.) Co-pending U.S. Appl. No. 17/000,049, filed Aug. 21, 2020, Specification, Claims, Figures.
Abiror, I.G., et al., "Electric Breakdown of Bilayer Lipid-Membranes . 1. Main Experimental Facts and Their Qualitative Discussion", Bioelectrochemistry and Bioenergetics, 6(1): p. 37-52 (1979).
Agerholm-Larsen, B., et al., "Preclinical Validation of Electrochemotherapy as an Effective Treatment for Brain Tumors", Cancer Research 71: 3753-3762 (2011).
Alberts et al., "Molecular Biology of the Cell," 3rd edition, Garland Science, New York, 1994, 1 page.
Alinezhadbalalami, N. et al., "Generation of Tumor-activated T cells Using Electroporation", Bioelectrochemistry 142 (2021) 107886, Jul. 13, 2021, 11 pages.
Al-Sakere et al., "Tumor ablation with irreversible electroporation," PLoS ONE, 2, e1135, 2007, 8 pages.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss. Cult. Meth., 15:56-62, 1993.
Appelbaum, L., et al., "US Findings after Irreversible Electroporation Ablation: Radiologic-Pathologic Correlation" Radiology 262(1), 117-125 (2012).
Talele, S. and P. Gaynor, "Non-linear time domain model of electropermeabilization: Effect of extracellular conductivity and applied electric field parameters", Journal of Electrostatics, 66(5-6): p. 328-334 (2008).
Talele, S. and P. Gaynor, "Non-linear time domain model of electropermeabilization: Response of a single cell to an arbitrary applied electric field", Journal of Electrostatics, 65(12): p. 775-784 (2007).
Talele, S., et al., "Modelling single cell electroporation with bipolar pulse parameters and dynamic pore radii". Journal of Electrostatics, 68(3): p. 261-274 (2010).

(56) References Cited

OTHER PUBLICATIONS

Teissie, J. and T.Y. Tsong, "Electric-Field Induced Transient Pores in Phospholipid-Bilayer Vesicles". Biochemistry, 20(6): p. 1548-1554 (1981).
Tekle, Ephrem, R. Dean Astumian, and P. Boon Chock, Electroporation by using bipolar oscillating electric field: An improved method for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra, BJU International (1999), 84, 1035-1037.
Thomson et al., "Investigation of the safety of irreversible electroporation in humans," J Vasc Interv Radiol, 22, pp. 611-621, 2011.
Tibbitt et al., "Hydrogels as Extracellular Matrix Mimics for 3D Cell Culture", Jul. 2009, Biotechnol Bioeng, 103(4),655-663.
TUNA—Suggested Local Anesthesia Guidelines, no date available.
U.S. Appl. No. 12/491,151 (U.S. Pat. No. 8,992,517), file history through Feb. 2015, 113 pages.
U.S. Appl. No. 12/609,779 (U.S. Pat. No. 8,465,484), file history through May 2013, 100 pages.
U.S. Appl. No. 12/757,901 (U.S. Pat. No. 8,926,606), file history through Jan. 2015, 165 pages.
U.S. Appl. No. 12/906,923 (U.S. Pat. No. 9,198,733), file history through Nov. 2015, 55 pages.
U.S. Appl. No. 13/332,133 (U.S. Pat. No. 10,448,989), file history through Sep. 2019, 226 pages.
U.S. Appl. No. 13/550,307 (U.S. Pat. No. 10,702,326), file history through May 2020, 224 pages.
U.S. Appl. No. 13/919,640 (U.S. Pat. No. 8,814,860), file history through Jul. 2014, 41 pages.
U.S. Appl. No. 13/958,152, file history through Dec. 2019, 391 pages.
U.S. Appl. No. 13/989,175 (U.S. Pat. No. 9,867,652), file history through Dec. 2017, 200 pages.
U.S. Appl. No. 14/012,832 (U.S. Pat. No. 9,283,051), file history through Nov. 2015, 17 pages.
U.S. Appl. No. 14/017,210 (U.S. Pat. No. 10,245,098), file history through Jan. 2019, 294 pages.
U.S. Appl. No. 14/558,631 (U.S. Pat. No. 10,117,707), file history through Jul. 2018, 58 pages.
U.S. Appl. No. 14/627,046 (U.S. Pat. No. 10,245,105), file history through Feb. 2019, 77 pages.
U.S. Appl. No. 14/808,679 (U.S. Pat. No. 11,655,466), file history through Aug. 2022, 253 pages.
U.S. Appl. No. 14/940,863 (U.S. Pat. No. 10,238,447), file history through Oct. 2019, 23 pages.
U.S. Appl. No. 15/011,752 (U.S. Pat. No. 10,470,822), file history through Jul. 2019, 54 pages.
U.S. Appl. No. 15/186,653 (U.S. Pat. No. 10,292,755), file history through Mar. 2019, 21 pages.
U.S. Appl. No. 15/310,114 (U.S. Pat. No. 10,471,254), file history through Aug. 2019, 44 pages.
U.S. Appl. No. 15/423,986 (U.S. Pat. No. 10,286,108), file history through Jan. 2019, 124 pages.
U.S. Appl. No. 15/424,335 (U.S. Pat. No. 10,272,178), file history through Feb. 2019, 57 pages.
U.S. Appl. No. 15/536,333 (U.S. Pat. No. 10,694,972), file history through Apr. 2020, 78 pages.
U.S. Appl. No. 15/843,888 (U.S. Pat. No. 10,537,379), file history through Sep. 2019, 83 pages.
U.S. Appl. No. 15/881,414 (U.S. Pat. No. 10,154,874), file history through Nov. 2018, 43 pages.
U.S. Appl. No. 16/152,743 (U.S. Pat. No. 11,272,979), file history through Jan. 2022, 89 pages.
U.S. Appl. No. 16/177,745 (U.S. Pat. No. 10,828,085), file history through Jun. 2020, 57 pages.
U.S. Appl. No. 16/210,771 (U.S. Pat. No. 11,607,537), file history through Dec. 2022, 139 pages.
U.S. Appl. No. 16/232,962 (U.S. Pat. No. 10,828,086), file history through Jun. 2020, 44 pages.
U.S. Appl. No. 16/275,429 (U.S. Pat. No. 10,959,772), file history through Feb. 2021, 18 pages.
U.S. Appl. No. 16/280,511, file history through Aug. 2021, 31 pages.
U.S. Appl. No. 16/352,759 (U.S. Pat. No. 11,311,329), file history through Mar. 2022, 258 pages.
U.S. Appl. No. 16/372,520 (U.S. Pat. No. 11,382,681), file history through Jun. 2022, 107 pages.
U.S. Appl. No. 16/404,392 (U.S. Pat. No. 11,254,926), file history through Jan. 2022, 153 pages.
U.S. Appl. No. 16/443,351 (U.S. Pat. No. 11,638,603), file history through Mar. 2023, 114 pages.
U.S. Appl. No. 16/520,901 (U.S. Pat. No. 11,406,820), file history through May 2022, 39 pages.
U.S. Appl. No. 16/535,451 (U.S. Pat. No. 11,453,873), file history through Aug. 2022, 85 pages.
U.S. Appl. No. 16/655,845 (U.S. Pat. No. 11,607,271), file history through Jan. 2023, 68 pages.
U.S. Appl. No. 17/069,359 (U.S. Pat. No. 11,737,810), file history through Apr. 2023, 27 pages.
Valdez, C. M. et al., "The interphase interval within a bipolar nanosecond electric pulse modulates bipolar cancellation," Bioelectromagnetics, vol. 39, No. 6, 441-450, 2018, 28 pages.
Van Den Bos, W. et al., "MRI and contrast-enhanced ultrasound imaging for evaluation of focal irreversible electroporation treatment: results from a phase i-ii study in patients undergoing ire followed by radical prostatectomy," European radiology, vol. 26, No. 7, pp. 2252-2260, 2016.
Verbridge et al., "Oxygen-Controlled Three-Dimensional Cultures to Analyze Tumor Angiogenesis." Tissue Engineering, Part A vol. 16, pp. 2133-2141 (2010).
Verma, A. et al., "Primer on Pulsed Electrical Field Ablation: Understanding the Benefits and Limitations," Circ. Arrhythmia Electrophysiol., no. September, pp. 1-16, 2021, 16 pages.
Pending U.S. Appl. No. 14/686,380, Advisory Action dated Oct. 20, 2021, 3 pages.
Pending U.S. Appl. No. 14/686,380, Amendment After Board Decision dated Apr. 3, 2023, 8 pages.
Pending U.S. Appl. No. 14/686,380, Appeal Brief filed Nov. 5, 2021, 21 pages.
Pending U.S. Appl. No. 14/686,380, Appeal Decision dated Jan. 30, 2023, 15 pages.
Pending U.S. Appl. No. 14/686,380, Applicant Initiated Interview Summary dated Feb. 9, 2021, 3 pages.
Pending U.S. Appl. No. 14/686,380, Applicant Initiated Interview Summary dated Mar. 8, 2021, 2 pages.
Pending U.S. Appl. No. 14/686,380, Examiner's Answer to Appeal Brief, dated Feb. 18, 2022, 16 pages.
Pending U.S. Appl. No. 14/686,380, Final Office Action dated May 9, 2018, 14 pages.
Pending U.S. Appl. No. 14/686,380, Final Office Action dated Oct. 6, 2020, 14 pages.
Pending U.S. Appl. No. 14/686,380, Final Office Action dated Sep. 3, 2019, 28 pages.
Pending U.S. Appl. No. 14/686,380, Non-Final Office Action dated Feb. 13, 2020, 11 pages.
Pending U.S. Appl. No. 14/686,380, Non-Final Office Action dated May 1, 2019, 18 pages.
Pending U.S. Appl. No. 14/686,380, Non-Final Office Action dated Nov. 22, 2017, 11 pages.
Pending U.S. Appl. No. 14/686,380, Notice of Non-Compliant Amendment dated May 25, 2023, 3 pages.
Pending U.S. Appl. No. 14/686,380, Reply Brief, dated Apr. 12, 2022, 4 pages.
Pending U.S. Appl. No. 14/686,380, Response to Feb. 13, 2020 Non-Final Office Action, filed Jul. 1, 2020, 8 pages.
Pending U.S. Appl. No. 14/686,380, Response to Jul. 19, 2017 Restriction Requirement, dated Sep. 15, 2017, 2 pages.
Pending U.S. Appl. No. 14/686,380, Response to May 9, 2018 Final Office Action with RCE, dated Aug. 30, 2018, 14 pages.

(56) References Cited

OTHER PUBLICATIONS

Pending U.S. Appl. No. 14/686,380, Response to Non-Final Office Action Filed Aug. 1, 2019, 11 pages.
Pending U.S. Appl. No. 14/686,380, Response to Nov. 22, 2017 Non-Final Office Action dated Mar. 28, 2018, 11 pages.
Pending U.S. Appl. No. 14/686,380, Response to Oct. 6, 2020 Final Office Action with RCE, dated Jan. 6, 2020, 11 pages.
Pending U.S. Appl. No. 14/686,380, Response to Sep. 3, 2019 Final Office Action, filed Jan. 3, 2020, 10 pages.
Pending U.S. Appl. No. 14/686,380, Restriction Requirement Jul. 19, 2017, 7 pages.
Pending U.S. Appl. No. 14/686,380, Amendment after Notice of Appeal, dated Oct. 12, 2021, 6 pages.
Pending U.S. Appl. No. 14/686,380, Non-Final Office Action dated May 7, 2021, 17 pages.
Pending U.S. Appl. No. 16/375,878, Applicant-Initiated Interview Summary dated Aug. 23, 2022, 7 pages.
Pending U.S. Appl. No. 16/375,878, Final Office Action dated Apr. 15, 2022, 8 pages.
Pending U.S. Appl. No. 16/375,878, Final Office Action dated Aug. 18, 2023, 11 pages.
Pending U.S. Appl. No. 16/375,878, Non-Final Office Action dated Jan. 23, 2023, 8 pages.
Pending U.S. Appl. No. 16/375,878, Non-Final Office Action dated Jun. 24, 2021, 8 pages.
Pending U.S. Appl. No. 16/375,878, Notice of Allowance dated Nov. 15, 2023, 6 pages.
Pending U.S. Appl. No. 16/375,878, Preliminary Amendment, filed Apr. 9, 2019, 9 pages.
Pending U.S. Appl. No. 16/375,878, Response to Apr. 15, 2022 Final Office Action, dated Aug. 15, 2022, 8 pages.
Pending U.S. Appl. No. 16/375,878, Response to Aug. 18, 2023 Final Office Action, dated Oct. 18, 2023, 9 pages.
Pending U.S. Appl. No. 16/375,878, Response to Jan. 23, 2023 Final Office Action, dated Apr. 24, 2023, 10 pages.
Pending U.S. Appl. No. 16/375,878, Response to Jun. 24, 2021 Non-Final Office Action, dated Dec. 22, 2021, 8 pages.
Pending U.S. Appl. No. 16/375,878, Second Preliminary Amendment, filed Feb. 5, 2020, 3 pages.
Pending U.S. Appl. No. 16/747,219, Applicant-Initiated Interview Summary dated Aug. 3, 2022, 4 pages.
Pending U.S. Appl. No. 16/747,219, Final Office Action dated Nov. 10, 2022, 12 pages.
Pending U.S. Appl. No. 16/747,219, Non-Final Office Action dated Mar. 31, 2022, 12 pages.
Pending U.S. Appl. No. 16/747,219, Non-Final Office Action dated May 25, 2023, 13 pages.
Pending U.S. Appl. No. 16/747,219, Notice of Allowance dated Dec. 26, 2023, 12 pages.
Pending U.S. Appl. No. 16/747,219, Preliminary Amendment filed Jan. 20, 2020, 5 pages.
Pending U.S. Appl. No. 16/747,219, Preliminary Amendment filed Jan. 4, 2021, 5 pages.
Pending U.S. Appl. No. 16/747,219, Response to Mar. 31, 2022 Non-Final Office Action, dated Aug. 1, 2022, 8 pages.
Pending U.S. Appl. No. 16/747,219, Response to May 25, 2023 Non-Final Office Action, dated Aug. 25, 2023, 9 pages.
Pending U.S. Appl. No. 16/747,219, Response to Nov. 10, 2022 Final Office Action, dated Feb. 10, 2023, 6 pages.
Pending U.S. Appl. No. 16/865,031, Final Office Action dated May 24, 2023, 18 pages.
Pending U.S. Appl. No. 16/865,031, Non-Final Office Action dated Nov. 28, 2022, 16 pages.
Pending U.S. Appl. No. 16/865,031, Notice of Allowance dated Oct. 4, 2023, 10 pages.
(Davalos, Rafael et al.) Co-Pending U.S. Appl. No. 18/846,198, filed Sep. 11, 2024, Specification, Claims, Figures.
(Davalos, Rafael V. et al.) Co-pending U.S. Appl. No. 18/767,746, filed Jul. 9, 2024, Specification, Claims, Figures.
(O'Brien, Timothy J. et al.) Co-Pending U.S. Appl. No. 18/608,958, filed Mar. 19, 2024, Specification, Claims, Figures.
Korohoda, W. et al. "Reversible and Irreversible Electroporation of Cell Suspensions Flowing Through a Localized DC Electric Field", Cellular & Molecular Biology Letters, vol. 18 (2013), pp. 102-119 (published Dec. 27, 2012).
Pending U.S. Appl. No. 16/938,778, Interview Summary dated Jun. 21, 2024, 1 page.
Pending U.S. Appl. No. 16/938,778, Notice of Allowance dated Jun. 21, 2024, 10 pages.
Pending U.S. Appl. No. 16/938,778, Response to Jan. 2, 2024 Non-Final Office Action, dated Apr. 2, 2024, 13 pages.
Pending U.S. Appl. No. 17/000,049, Examiner Interview Summary dated Jul. 8, 2024, 7 pages.
Pending U.S. Appl. No. 17/000,049, Final Office Action dated Mar. 29, 2024, 15 pages.
Pending U.S. Appl. No. 17/000,049, Response to Dec. 11, 2023 Non-Final Office Action, dated Mar. 11, 2024, 9 pages.
Pending U.S. Appl. No. 17/152,379, Non-Final Office Action dated Apr. 23, 2024, 14 pages.
Pending U.S. Appl. No. 17/152,379, Response to Apr. 23, 2024 Non-Final Office Action, filed Aug. 23, 2024, 7 pages.
Pending U.S. Appl. No. 17/172,731, Final Office Action dated Apr. 10, 2024, 5 pages.
Pending U.S. Appl. No. 17/172,731, Notice of Allowance dated Jun. 27, 2024, 7 pages.
Pending U.S. Appl. No. 17/172,731, Response to Apr. 10, 2024 Final Office Action, dated Jun. 10, 2024, 6 pages.
Pending U.S. Appl. No. 17/591,992, Final Office Action dated Jul. 30, 2024, 10 pages.
Pending U.S. Appl. No. 17/591,992, Response to Feb. 23, 2024 Non-Final Office Action dated May 23, 2024, 10 pages.
Pending U.S. Appl. No. 18/100,835, Restriction Requirement dated Jun. 28, 2024, 6 pages.
Pending U.S. Appl. No. 18/120,158, Non-Final Office Action dated Jun. 20, 2024, 13 pages.
Pending U.S. Appl. No. 18/348,605, Non-Final Office Action dated Sep. 5, 2024, 10 pages.
Pending U.S. Appl. No. 18/402,231, Preliminary Amendment dated Mar. 5, 2024, 5 pages.
Pending U.S. Appl. No. 18/404,473, Preliminary Amendment dated May 13, 2024, 6 pages.
Pending U.S. Appl. No. 18/846,198, Preliminary Amendment dated Sep. 11, 2024, 8 pages.
Pending Application No. EP 15793361.5, Brief Communication from the EPO, dated Aug. 19, 2024, 1 page.
Pending Application No. EP 15793361.5, EPO Result of Consultation, Aug. 12, 2024, 3 pages.
Pending Application No. EP 15793361.5, Response to Feb. 8, 2024 Communication, Filed Aug. 2, 2024, 40 pages.
Pending Application No. EP 15793361.5, Supplemental Response to Feb. 8, 2024 Communication, Filed Aug. 16, 2024, 9 pages.
Pending Application No. PCT/US23/76626, International Search Report and Written Opinion, dated Apr. 17, 2024, 12 pages.
Reti, I. M. and Davydow, D. S., "Electroconvulsive Therapy and Antibiotics: A Case Report", J. ECT, vol. 23, No. 4, Dec. 2007, pp. 289-290.
(Neal, Robert E. et al.) Co-pending U.S. Appl. No. 18/930,252, filed Oct. 29, 2024, Specification, Claims, Figures.
(Neal, Robert E. et al.) Co-pending U.S. Appl. No. 19/019,625, filed Jan. 14, 2025, Specification, Claims, Figures.
Co-pending U.S. Appl. No. 17/535,742, Non-final Office Action dated Dec. 13, 2024, 12 pages.
Pending U.S. Appl. No. 17/152,379, Final Office Action dated Dec. 11, 2024, 8 pages.
Pending U.S. Appl. No. 17/591,992, Non-Final Office Action dated Nov. 18, 2024, 9 pages.
Pending U.S. Appl. No. 18/100,835, Non-Final Office Action dated Oct. 23, 2024, 10 pages.
Pending U.S. Appl. No. 18/348,605, Response to Sep. 5, 2024 Non-Final Office Action, dated Dec. 5, 2024, 7 pages.

(56) References Cited

OTHER PUBLICATIONS

Pending U.S. Appl. No. 18/402,231, Non-Final Office Action dated Dec. 13, 2024, 8 pages.

* cited by examiner

TEMPERATURE, K

TEMPERATURE, K

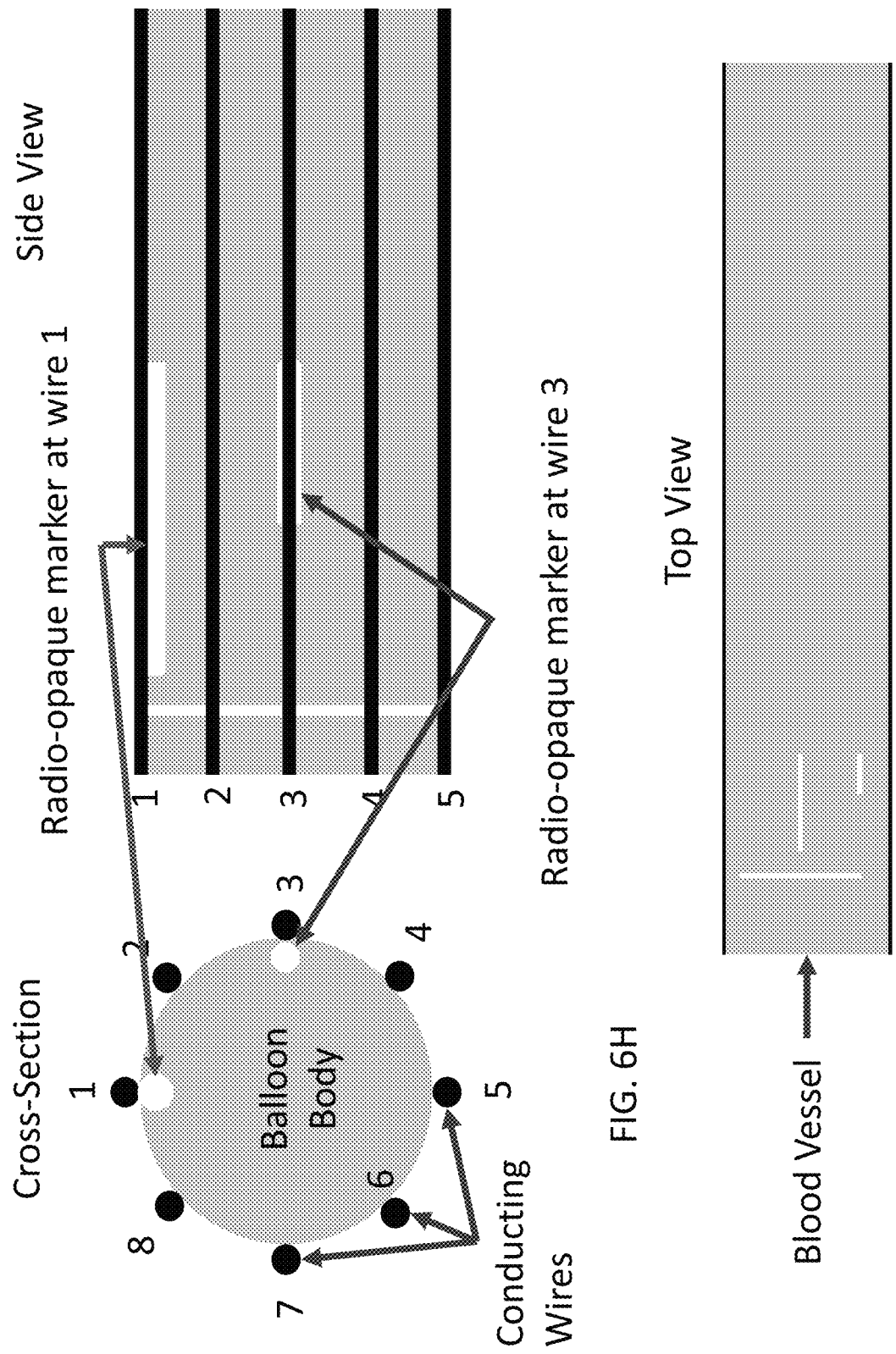

DEVICE AND METHOD FOR ELECTROPORATION BASED TREATMENT

CROSS-REFERENCE TO RELATED APPLICATIONS

This application is a Continuation application of U.S. patent application Ser. No. 16/865,772, filed May 4, 2020, which application published as U.S. Patent Application Publication No. 2020/0323576 on Oct. 15, 2020, and which is abandoned. The '772 application is a Continuation application of U.S. patent application Ser. No. 13/550,307, filed Jul. 16, 2012, which published as U.S. Patent Application Publication No. U.S. 2013/0184702 on Jul. 18, 2013. The '307 application issued as U.S. Pat. No. 10,702,326 on Jul. 7, 2020, and relies on the disclosure of and claims priority to and the benefit of the filing date of U.S. Provisional Application No. 61/508,251, filed Jul. 15, 2011. The disclosures of which are hereby incorporated by reference herein in their entireties.

BACKGROUND OF THE INVENTION

Field of the Invention

The present invention relates to medical devices and methods for treating, reducing, or preventing stenosis using non-thermal irreversible electroporation. Embodiments of the present invention provide balloon catheter devices for treating or preventing stenosis comprising a plurality of electrodes for selectively and irreversibly electroporating a portion of the inner circumference of a tubular structure within the body. Such devices, systems and methods are particularly useful for treating asymmetrical stenosis.

Description of Related Art

Atherosclerosis is the main cause of heart attack, stroke and gangrene of the extremities. See Burt H M, Hunter W L (2006), Drug-eluting stents: a multidisciplinary success story, Adv Drug Deliv Rev 58: 350-357 ("Burt 2006"); and Lusis A J (2000) Atherosclerosis, Nature 407: 233-241 ("Lusis 2000"). Three different processes have been identified in studies of animals with induced hypercholesterolaemia that are thought to participate in the formation of atherosclerotic lesions: 1) proliferation of smooth muscle cells, macrophages and lymphocytes; 2) the formation by smooth muscle cells of a connective tissue matrix comprising elastic fiber proteins, collagen and proteoglycans; and 3) accumulation of lipid and mostly free and sterified cholesterol in the surrounding matrix and the associated cells. See Ross R (1993), The pathogenesis of atherosclerosis: a perspective for the 1990s, Nature 362: 801-809.

The introductions of balloon angioplasty and stent implantation in the coronary arteries have reduced significantly the fatalities associated with this disease, however, coronary artery restenosis and neointimal hyperplasia remain clinical problems. See Lusis 2000; and A I Suwaidi J, Berger P B, Holmes D R, Jr. (2000) Coronary artery stents, Jama 284: 1828-1836. Millions of people are affected by atherosclerosis. One feature of this disease is stenosis, which is defined as an abnormal narrowing or contraction of a tubular body part such as arteries, veins, non-vascular ducts and other tubular structures such as urethra, fallopian tubes, esophageal, bronchial passages, and the like. Stenosis causes decreased blood flow through the vessel. A common treatment for stenosis is bypass surgery with less invasive procedures, such as angioplasty procedures like PTA (percutaneous transluminal angioplasty) also available. Angioplasty involves inserting a balloon catheter into the body to the location of the stenosis, then inflating the balloon against the lesion, and applying pressure to compress the lesion and widen or restore the inside diameter of the blood vessel to restore blood flow. Variations of PTA procedures have been used to treat peripheral arterial stenosis, coronary lesions and other non-vascular tubular structures such as biliary ducts.

Although PTA treatments find success in restoring blood flow, such success may be limited or temporary under certain circumstances. For instance, it has been found that anywhere from three to six months following the angioplasty procedure about half of those treated with PTA develop a re-narrowing or occlusion of the vessel, referred to as restenosis. While the original blockage is formed by plaque deposits on the vessel wall, restenosis is caused by growth of smooth muscle cells of the treated artery after angioplasty. It is the trauma imposed on the vessel wall during angioplasty itself that is the cause of restenosis. More particularly, the body reacts to the angioplasty procedure as an injury and produces scar tissue as cells regenerate on the inner wall of the blood vessel in response to the procedure. It is overgrowth of these cells that causes the restenosis, which is the recurrence of stenosis after the PTA procedure. A second angioplasty procedure or bypass are common treatments for restenosis, but each of these exposes the patient to additional risks. This is because the angioplasty procedure is often a temporary fix as it will retraumatize the vessel wall—resulting in the recurrence of smooth muscle cell proliferation. Adding further complexity to the issue, restenosis often presents itself asymmetrically, characterized by cellular regrowth on only portions of the circumference of the vessel wall. It has been found that eccentric and polypoid narrowings are not amenable to treatment with PTA alone. See Becker G J, Katzen B T, Dake M D, Noncoronary angioplasty, Radiology 1989; 170:921-940.

In attempts to limit the amount of restenosis after angioplasty, efforts have been made to reduce the trauma associated during treatment procedures for stenosis. Such efforts include using balloon catheters equipped for cutting or excising the lesions or in combination with an endomyocardial biopsy device. These efforts, however, have not proven any greater success over conventional angioplasty techniques in preventing restenosis after surgery.

Post-angioplasty approaches for reducing restenosis have also been pursued. One such technique involves implanting drug-eluting stents comprising compositions for suppressing the growth of scar tissue. These techniques have been known to reduce restenosis but are not preferred due to complications, such as localized blood clots after elution of the drug, stent fracture, or other long-term implant issues. Most notable risk factors with stents concern the arterial wall injury that is generated with the implantation of the stent and the pressure applied by the balloon. In-stent restenosis after bare-metal stent (BMS) placement results in an aggressive healing response (neointimal hyperplasia) that causes vascular narrowing. See Burt 2006; Legrand V (2007), Therapy insight: diabetes and drug-eluting stents, Nat Clin Pract Cardiovasc Med 4: 143-150; and Ward M R, Pasterkamp G, Yeung A C, Borst C (2000) Arterial remodeling, Mechanisms and clinical implications, Circulation 102: 1186-1191.

Still others have used angioplasty combined with a technique referred to as non-thermal irreversible electroporation. The IRE approach generally involves treatment of the cells subjected to angioplasty to a therapeutic electric field. The goal is to target the vascular cells to ablate and kill the cells without causing thermal or mechanical damage. This approach selectively kills the target cells while avoiding damage to the structure of the artery and surrounding tissue. Restenosis is thus avoided or reduced because the targeted vascular cells are killed, which then do not have the capability of forming scar tissue (neointimal).

Generally, irreversible electroporation (IRE) is a minimally invasive technique to ablate undesired tissue. See Davalos R V, Mir L M, Rubinsky B (2005), Tissue ablation with irreversible electroporation, Annals of Biomedical Engineering 33: 223-231 ("Davalos 2005"). Maor and colleagues showed that IRE reduces the vascular smooth muscle cells population of major blood vessels without affecting the extracellular matrix, which is crucial in the treatment of coronary artery disease. See Maor E, Ivorra A, Leor J, Rubinsky B (2007), The effect of irreversible electroporation on blood vessels, Technology in Cancer Research and Treatment 6: 307-312. The procedure involves delivering a series of low energy (intense but short) electric pulses to the targeted tissue. These pulses permanently destabilize the cell membranes of the treated tissue and cause cell death. IRE has been shown to be an effective means of tissue ablation that does not require drugs, and creates no secondary thermal effects thereby, preserves extracellular matrix, micro-vasculature and nerves. See Rubinsky B (2007), Irreversible Electroporation in Medicine, Technology in Cancer Research and Treatment 6: 255-260. Furthermore, IRE ablates tissue with sub-millimeter resolution and the treated area can be imaged in real-time using ultrasound, or other imaging techniques such as Magnetic Resonance Imaging, Computed Tomography and/or Intravascular Ultrasound (IVUS).

More particularly, as a result of being exposed to the IRE electric field, the pores of the target cells are opened to a degree beyond which they can recover and the cells die. Concerning restenosis in particular, with fewer cells remaining on the vascular wall after the angioplasty procedure, the cells are unable to grow thus preventing restenosis altogether, or the cells which are limited in number can only experience a limited amount of cellular regrowth thus reducing the amount of restenosis. IRE can be performed before, during, and/or after angioplasty. In some cases, the IRE is preferably performed before restenosis occurs, e.g., before angioplasty to treat tissue that will later be exposed to an angioplasty procedure.

It has been known to use IRE on blood vessels using plate electrodes placed around the carotid artery to apply the electric pulses. See Maor, E., A. Ivorra, J. Leor, and B. Rubinsky, The Effect of Irreversible Electroporation on Blood Vessels, Technol Cancer Res Treat, 2007, 6(4): p. 307-312; Maor, E., A. Ivorra, J. Leor, and B. Rubinsky, Irreversible electroporation attenuates neointimal formation after angioplasty, IEEE Trans Biomed Eng, 2008, 55(9): p. 2268-74; and Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757. Unfortunately, this electrode design is highly invasive and requires the physical exposure of the targeted vessel in order to treat it.

In other existing IRE procedures for treatment of restenosis, the entire circumference of the vessel wall is exposed to the IRE electric field. In such designs it has been known to use an electrode with positive and negative independent conducting surfaces, which are energized in an all-or-nothing system, energizing the entire circumference of the electrode at the same time and with equal energy delivery. Such an approach is not desirable for cases of asymmetrical restenosis, however, where only a portion or less than the entire circumference of the vessel wall is diseased. In treating asymmetric restenosis with circumferential IRE, vascular cells on non-diseased portions of the vessel wall are unnecessarily destroyed.

Thus, it is apparent that there is a need for less invasive, less traumatic treatment procedures for treating, reducing, or preventing restenosis. Especially needed are procedures capable of targeting only the diseased portions of the vascular structure, or capable of targeting only portions of the vascular structure susceptible to restenosis, such as tissue previously subjected to stenosis treatment and/or stenotic tissue prior to treatment.

SUMMARY OF THE INVENTION

To this end, embodiments of the present invention provide devices, systems, and methods for treating lesions such as vascular stenosis including restenosis. Especially preferred are such devices, systems, and methods for treating asymmetric lesions, i.e., lesions that extends only partially around the vessel.

Non-thermal irreversible electroporation (NTIRE) treatment methods and devices of the invention include a plurality of electrodes positioned along a balloon of a balloon catheter that are electrically independent from each other so as to be individually selectable in order to more precisely treat an asymmetrical lesion.

According to one aspect of the present invention, a method of treating a stenosis of a tubular body part by non-thermal irreversible electroporation is provided. The method involves: inserting, through the tubular body part, a balloon catheter having at least three electrodes positioned and spaced apart along the balloon, the electrodes being electrically independent from each other; expanding the balloon to bring the electrodes near a stenosis to be treated; determining which electrodes are near the stenosis; and applying electrical pulses to the electrodes according to the determination of which electrodes are near the stenosis, the applied pulses being in an amount which is sufficient to induce irreversible electroporation of cells of the stenosis, but which is insufficient to induce thermal damage to substantially all of the cells of the stenosis such that substantially all stenosis cells are killed by non-thermal irreversible electroporation.

In another aspect of the invention, an entire circumferential area of a vessel can be treated by selectively energizing selected conductive surfaces of an electrode, i.e., delivering the electrical charge asymmetrically with respect to the vessel, however, selection of the conductive surfaces can be rotated for example sequentially to cover a whole circumferential section of a vessel. In such embodiments, since smaller segments of the electrode are being activated at certain times, less power is needed and developing electronics for this would be less complex task.

In another aspect of the invention, the step of applying electrical pulses includes selecting at least one electrode to which the electrical pulses are not to be applied.

In another aspect of the invention, the step of applying electrical pulses includes connecting through a switch a pulse generator output to any pair of the electrodes independent of the other electrodes.

In another aspect of the invention, the step of applying electrical pulses includes control the switch to output the electrical pulses to only those electrodes that have been selected based on a determination of which electrodes are near the stenosis.

In another aspect of the invention, the method further comprises determining at least one individualized electrical parameter for each pair of electrodes based on the determination of which electrodes are near the stenosis.

In another aspect of the invention, the electrical parameter includes Voltage or pulse duration.

In another aspect of the invention, the method further comprises determining at last one individualized electrical parameter for each pair of electrodes based on the depth and proximity of the stenosis in relation to the electrode positions.

In another aspect of the invention, the method includes determining an individualized voltage level to use for each pair of electrodes based on the depth of the restenosis near the each pair.

In another aspect of the invention, which electrodes are near the stenosis is determined by one or more imaging markers disposed near the electrodes.

In another aspect of the invention, the imaging markers include a radiopaque marker capable of rendering an image on any imaging modality, such as CT or IVUS.

In another aspect of the invention, which electrodes are near the stenosis is determined by applying test pulses to different pairs of the electrodes and measuring at least one electrical characteristic of the stenosis cells for the different pairs of electrodes.

In another aspect of the invention, the step of determining includes measuring an electrical resistance as the at least one electrical characteristic of tissue cells.

In another aspect of the invention, the method further comprises displaying a graphical representation and identification of the electrodes in positional relationship to the stenosis. In other words, electrode numbers are shown in relation to the position of the lesion so as to enable a user to determine which electrodes are the closest to the lesion and which electrodes close to the deepest part of the lesion.

In another aspect of the invention, the method further comprises displaying a graphical representation of the stenosis and a graphical representation and identification of the electrodes in positional relationship to the stenosis.

In another aspect of the invention, the method comprises electroporating tissue for the purpose of facilitating electro-chemotherapy or electrogenetherapy, wherein cells are reversibly electroporated instead of killed, or the treatment is administered without necessarily killing cells or target tissue. Such methods can include inserting into a vessel an electrode having a plurality of elongated electrically conductive wires disposed lengthwise along the electrode and circumferentially spaced a selected distance from one another; orienting the electrode within the vessel to provide one or more of the electrically conductive wires in position to deliver one or more electrical pulse to target tissue; selecting one or more but less than all of the electrically conductive wires for administering the electrical pulse(s); administering the electrical pulse(s) from the selected electrically conductive wires to deliver the electrical pulse(s) to the target tissue and less than all vessel circumference; and wherein the administering is performed for a time and under circumstances sufficient to deliver drugs or genes to the target tissue or a portion thereof.

Such electrodes can also be used to enable directional targeting for other electroporation based therapies as well. For example, methods of directional targeting for selective macromolecule delivery, such as gene transfer are another application for electrodes of the invention. More particularly, the electrodes can be used for delivering insulin-making genes to pancreatic islets by way of the splenic artery; or can be used in chemotherapy treatments, especially for tumors; or can be used for other improved drug uptakes, such as for non-cancerous drug transports as well. Indeed, devices of the invention can be used as a device for directionally delivering any number of electrically-relevant interventional procedures to be delivered in a radially directed manner through blood vessels. Yet other applications include directional radiofrequency ablation or deep-brain stimulation, to name a couple.

According to another embodiment of the present invention, a medical device for treating a stenosis of a tubular body part by non-thermal irreversible electroporation is provided. The device includes a pulse generator, a balloon catheter, and at least three individually addressable (electrically independent) electrodes. The pulse generator generates electrical pulses in an amount which is sufficient to induce irreversible electroporation of cells of a stenosis to be treated, but which is insufficient to induce thermal damage to substantially all of the cells of the stenosis. The electrodes are positioned and spaced apart along the balloon, and electrically independent from each other. The electrodes are adapted to receive the electrical pulses from the pulse generator such that substantially all of the cells of the stenosis are killed by non-thermal irreversible electroporation. The ability to select which electrodes to energize based on the proximity of the lesion to the electrodes allows more precise targeting of the lesion while minimizing possible damage to surrounding healthy tissue.

In another aspect of the invention, the medical device further comprises a switch connected between a pulse generator and the electrodes, and adapted to connect the pulse generator output to any pair of the electrodes independent of the other electrodes.

In another aspect of the invention, the medical device further comprises a treatment control module adapted to control the switch to output the electrical pulses to those electrodes that have been selected based on a determination of which electrodes are near the stenosis.

In another aspect of the invention, the treatment control module is adapted to determine at least one individualized electrical parameter for each pair of electrodes based on a determination of which electrodes are near the stenosis.

In another aspect of the invention, the electrical parameter of the treatment control module includes Voltage or pulse duration.

In another aspect of the invention, the medical device further comprises one or more imaging markers disposed near the electrodes to determine which electrodes are near the stenosis.

In another aspect of the invention, the medical device comprises imaging markers that include a radiopaque marker.

In another aspect of the invention, the treatment control module is adapted to determine which electrodes are near the stenosis by applying test pulses to different pairs of the electrodes and measuring at least one electrical characteristic of the stenosis cells for the different pairs of electrodes.

In another aspect of the invention, the treatment control module is adapted to measure an electrical resistance as the at least one electrical characteristic of tissue cells.

In another aspect of the invention, the treatment control module is adapted to display a graphical representation and identification of the electrodes in positional relationship to the stenosis.

In another aspect of the invention, the treatment control module is adapted to display a graphical representation of the stenosis and a graphical representation and identification of the electrodes in positional relationship to the stenosis.

In another aspect of the invention, the treatment control module is adapted to determine at last one individualized electrical parameter for each pair of electrodes based on the depth and proximity of the stenosis in relation to the electrode positions.

In another aspect of the invention, the treatment control module is adapted to determine an individualized voltage level to use for each pair of electrodes based on the depth of the restenosis near the each pair.

In another embodiment of the invention, a method for treating a lesion of a tubular body part by non-thermal irreversible electroporation is provided. The method includes: (a) inserting into the tubular body part a plurality of elongated electrodes disposed lengthwise and circumferentially spaced a selected distance from one another; (b) positioning the electrodes within the tubular body part to provide one or more of the electrodes in position to deliver a plurality of electrical pulse to a target lesion; (c) selecting electrodes among the plurality of electrodes for administering the electrical pulses; and (d) administering the electrical pulses through only the selected electrodes to the target lesion in an amount which is sufficient to induce irreversible electroporation of cells of the target lesion, but which is insufficient to induce thermal damage to substantially all of the cells of the target lesion such that substantially all cells f the target lesion are killed by non-thermal irreversible electroporation.

In another aspect of the invention, the electrode comprises a flexible catheter and inflatable balloon and the electrodes are disposed lengthwise along and are circumferentially spaced around a surface of the inflatable balloon.

In another aspect of the invention, the method further comprises determining an orientation of the electrode within the tubular body part by imaging, wherein the electrode comprises at least one imaging marker for determining location of the electrodes.

In another aspect of the invention, the method further comprises measuring a distance between the imaging markers and using the distances to calculate rotational orientation of the electrode.

In another aspect of the invention, the one marker is radio-opaque.

In another aspect of the invention, at least two radio-opaque markers and at least one intravascular ultrasound marker are provided on or near an inflatable balloon.

In another aspect of the invention, the selection step includes: (a) administering one or more test pulses through any one or more of pairs of the electrodes; (b) determining from the test pulses one or more electrical characteristics of tissue subjected to the test pulses and based on the electrical characteristics further determining a depth of the target lesion; and (c) generating a protocol for administering higher voltage electrical pulses between electrode pairs positioned for treating deep restenosis and for administering lower voltage electrical pulses between electrode pairs positioned for treating shallow restenosis.

In another aspect of the invention, the test pulse or signal is a non-electroporating test pulse.

Additionally, in embodiments having an inflatable balloon, the electrically conductive wires (electrodes) can be disposed lengthwise along the electrode and can be circumferentially spaced around the electrode. In preferred embodiments, the electrically conductive wires are disposed circumferentially around the electrode and in contact with a surface of the inflatable balloon.

According to methods of the invention, orientation of the electrode within a body or vessel can be determined. This is particularly helpful for example in situations where it is desired to treat only a portion of the circumferential surface area of a blood vessel. In this situation, it may be desired to know the location of fewer than all of the electrically conductive wires relative to the location of asymmetrical restenosis within a blood vessel. Knowing the relative location of the wires, a practitioner can selectively energize only that portion of the electrode to treat the restenosis site thus leaving intact healthy tissue remaining on other portions of the circumferential surface area of the blood vessel. One such technique can employ an electrode comprising at least one imaging marker and determining the location of the electrically conductive wires by imaging the device in a body or vessel.

Using techniques of the invention and an electrode with at least one imaging marker, methods of the invention can include measuring a distance between the imaging markers and using the distances to calculate rotational orientation of the electrode.

Imaging markers disposed in the electrodes of the invention can be radio-opaque. In embodiments, electrodes can comprise at least one radio-opaque marker. In preferred embodiments, the electrodes can comprise at least two radio-opaque markers and at least one intravascular ultrasound marker. Further, there can be a plurality of radio-opaque markers, each associated with an individual electrically conductive wire of the electrode.

Another method for determining orientation relative to stenotic tissue of electrically conductive wires of an electrode can comprise: (a) inserting into a treatment area, such as a vessel, an electrode having a plurality of electrically conductive wires; (b) administering one or more test signals between two of the electrically conductive wires and subjecting tissue to the test signal(s); (c) determining from the test signal(s) one or more electrical characteristics of the tissue subjected to the test signal(s); and (d) comparing the electrical characteristic(s) to one or more threshold to confirm whether the tissue subjected to the test signal(s) is stenotic and whether the electrically conductive wires are in position to deliver an electrical charge to target stenotic tissue.

The electrical characteristics of the tissue can be determined, e.g., from resistance measurements, impedance measurements, and electrical impedance tomography.

Further embodiments of the invention include a method of mapping depth of stenotic tissue in real-time comprising: (a) inserting into a vessel an electrode having pairs of electrically conductive wires; (b) administering one or more test pulse between any one or more, or all, of the electrically conductive wire pairs; (c) determining from the test pulse(s) one or more electrical characteristics of tissue subjected to the test pulse(s) and based on the electrical characteristics further determining depth of stenosis; and (d) generating a protocol for administering higher voltage electrical pulse(s) between electrically conductive wire pairs positioned for treating deep stenosis and for administering lower voltage electrical pulse(s) between electrically conductive wire pairs positioned for treating shallow stenosis.

Methods disclosed in this specification can be used for treating, preventing, and/or reducing stenosis. Thus, methods according to embodiments of the invention may include identifying stenotic tissue as the target tissue.

An irreversible electroporation medical device is also encompassed within the scope of the present invention and can comprise: (a) an intravascular catheter type electrode having an inflatable balloon and a plurality of electrically conductive wires disposed lengthwise along the electrode/balloon/catheter; and (b) a plurality of imaging markers, each disposed relative to an electrically conductive wire, such that the markers, when subjected to imaging, reveal the identification of each wire and the distance between markers from which rotational orientation of the electrode within a body can be determined. In embodiments, the electrically conductive wires can be elongated and circumferentially spaced around the electrode a selected distance from one another. In other embodiments, the electrically conductive wires can be annular and longitudinally spaced along the length of the electrode a selected distance from one another.

Such methods can employ devices comprising imaging markers that are radio-opaque. Preferably, methods can comprise an electrode with at least two radio-opaque markers and at least one intravascular ultrasound marker to be used in determining orientation of the electrode relative to a treatment site.

Systems are also included within the scope of the invention. Such systems can include an intravascular IRE system comprising: (a) at least one intravascular catheter type electrode having an inflatable balloon and a plurality of electrically conductive wires disposed lengthwise along the electrode and circumferentially spaced a selected distance from one another; (b) an electrical pulse generator in operable communication with and for delivering electrical pulses to the plurality of electrically conductive wires; and (c) a control system in operable communication with the electrical pulse generator comprising a computer program embodied in a computer-readable storage medium, which program when executed, enables a computer to perform a method comprising: (i) determining orientation of the electrically conductive wires relative to target tissue; (ii) selecting one or more but less than all of the electrically conductive wires for administering the electrical pulse(s); and (iii) energizing one or more of the electrically conductive wires to deliver the electrical pulse(s) to the target tissue.

Objects of the invention include computer programs for running the IRE methods, systems, and devices described in this specification. Such computer programs can be embodied in a computer-readable storage medium, which when executed, enables a computer to perform a method comprising: (a) determining orientation relative to target tissue of at least one electrically conductive wire of an electrode; (b) selecting one or more but less than all of the electrically conductive wires for administering electrical pulse(s); and (c) energizing the selected wires to deliver the electrical pulse(s) to the target tissue.

BRIEF DESCRIPTION OF THE DRAWINGS

The accompanying drawings illustrate certain aspects of some embodiments of the present invention, and should not be used to limit or define the invention. Together with the written description the drawings serve to explain certain principles of the invention.

FIG. 1A shows all components clear to see underlying structure and where FIG. 1B shows the labeled components with opaque inner components.

FIG. 6H is a schematic diagram showing the cross section and a side view of a representative electrode with imaging markers to indicate electrode orientation.

FIGS. 6I-M are schematic diagrams showing a top view of the electrode in a blood vessel, illustrating how the imaging markers would show up on an imaging apparatus when oriented in various rotational orientations within the vessel.

DETAILED DESCRIPTION OF VARIOUS EMBODIMENTS OF THE INVENTION

Figure 1A:
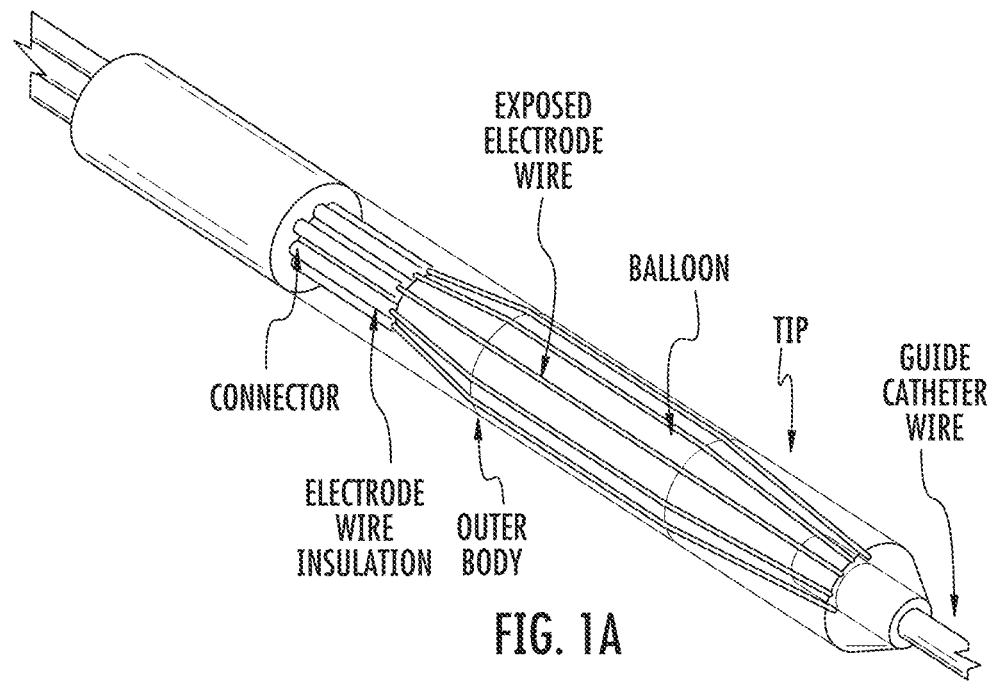
FIGS. 1A-B are schematic diagrams showing a representative embodiment of a catheter type electrode device according to the present invention, where

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Embodiments of the present invention include devices, systems, and methods employing expandable radially targeting electrodes. The electrodes can be designed for endovascular-based electroporation therapies and adapted for implementation with catheter-based guidance. This type of electrode with independently energized surfaces is also adaptable to any number of physical and clinical scenarios where radial targeting is desired.

Preferred electrode designs can be configured to use the combination of electrically conductive wires with an angioplasty balloon to bring the electrodes into direct contact with the targeted region, such as neointimal tissue. More specifically, designs of the present invention can employ for example eight independent conducting surfaces (wires or highly conducting solutions) to administer the electric pulses. The use of multiple conducting surfaces contained within the same electrode presents many advantages over the current state of the art designs. The electrically conductive surfaces of the electrode are not limited to wires. For example, any structure capable of providing a surface for delivering an electric charge can be used, including where the electrically conductive surfaces are bands or strips of material, or are printed on the surface of the balloon, or even further are compartments within an inflatable balloon comprising a highly conductive solution. Energizing the electrically conductive surfaces in sequence rather than collectively promotes an outward distribution of the electric field, reducing thermal effects and requiring lower voltages for treatment. Such techniques provide for an expanded treatment zone by energizing only a few of the electrically conductive wires at a time rather than the entire circumference of the electrode in one shot. In addition, by allowing independent spatial control of which portions of the electrode are energized (i.e., which wires), the electric field distribution may be customized in a manner that most effectively treats a specific lesion, such as an asymmetrical restenosis, while minimizing any damaging effects on healthy tissue. This allows a practitioner to more aggressively treat focally enlarged portions of a lesion while being more conservative on smaller regions of the same stenosis, which is important because it allows for improved accuracy in restenosis-ablation vascular-based surgeries. Further, applications include targeting other volumes located only on one side of a vessel, such as gene transfer targets just outside the vessel or tumor ablation using the tumor vasculature.

Accordingly, embodiments of this invention may be used as a catheter-style electrode to access target restenotic lesions from within the vessel. Embodiments of the present invention may also be used to target tissue disposed outside of the outer circumference of a vessel, such as an area between two or more blood vessels within a body. The use of a catheter electrode allows a practitioner to insert the electrode through a peripheral vessel, as is typical of current percutaneous vascular techniques, such as angioplasty and stenting. This renders treatments minimally invasive and advantageous over previous IRE investigations on blood vessels.

In the context of this specification, it should be noted that the terms "electrode," "electrode device," "device," "balloon catheter electrode," "catheter electrode," or "device" are typically used to refer to the IRE medical device as a whole, which may include a catheter, balloon, and electrically conductive wires. The terms "conducting surfaces," "electrically conductive wires," "conducting wires," "wire electrodes," and "wires" are typically used to refer to a portion of the electrode, such as a pair or pairs of electrodes, which may be selectively energized to deliver electrical pulses. Notwithstanding these typical meanings, in some embodiments in this specification, the terms may be used interchangeably.

Figure 1B:
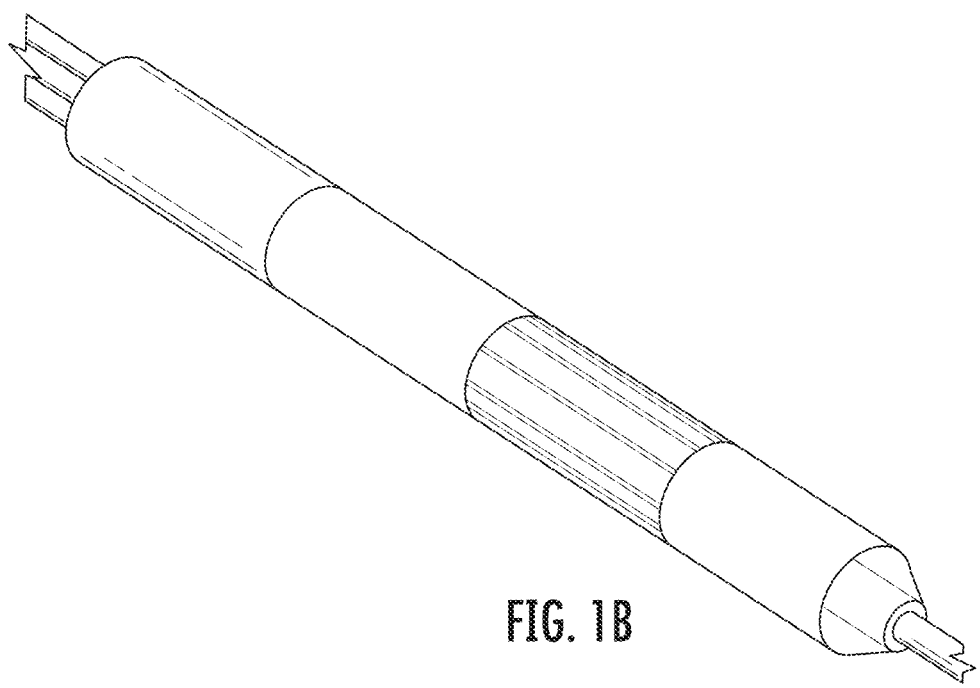

Exemplary electrodes according to embodiments of the invention are shown in FIGS. 1A-E. More particularly, as shown in FIGS. 1A-B, some of the components of the electrode device include a guidewire, tip, outer body, connector, balloon, and partially insulated conducting wires. The configuration depicted in this embodiment has a 2 mm diameter and is therefore designed for larger coronary vessels, such as the right coronary artery or left main artery, with proximal to medial lumen diameters of roughly 3.6 and 4.3 mm, respectively. See Dodge, J. T., Jr., B. G. Brown, E. L. Bolson, and H. T. Dodge, Lumen diameter of normal human coronary arteries, Influence of age, sex, anatomic variation, and left ventricular hypertrophy or dilation, Circulation, 1992, 86(1): p. 232-46. Such vessels may have typical restenotic lumen diameters of approximately 2.5 mm. See Radke, P. W., A. Kaiser, C. Frost, and U. Sigwart, Outcome after treatment of coronary in-stent restenosis—Results from a systematic review using meta-analysis techniques, European Heart Journal, 2003, 24(3): p. 266-273.

Modern micromachining techniques will allow for the construction of even smaller designs that may target smaller vessels, such as the distal portions and branches of the coronary arteries. Indeed, the devices of the present invention may also be scaled up for other applications. Accordingly, the diameter of the outer body of electrodes of the invention can range for example from about 0.1 mm up to about 5 cm. Preferably, electrode embodiments of the invention have an outer diameter ranging from about 0.5 mm to 5 mm, such as from about 1 mm to about 3 mm, such as about 1.5 mm to about 2 mm, or from about 0.75 mm to 3 cm.

In embodiments, the guidewire is the narrowest physical component and is used to direct the surgeon into the appropriate vessel. Although not typical, it can be hollow so that it may be used with a soluble contrast agent used for angiography and fluoroscopy, similar to typical endovascular therapies. See Schwartz, R. S., J. G. Murphy, W. D. Edwards, A. R. Camrud, R. E. Vliestra, and D. R. Holmes, Restenosis after balloon angioplasty, A practical proliferative model in porcine coronary arteries, Circulation, 1990, 82(6): p. 2190-200. The guidewire is usually of a smaller diameter than the diameter of the outer body of the balloon.

The guidewire or catheter forms the support for which all other components of the device are arranged. Over a portion of the catheter between the distal tip and the proximal end of the device is disposed an inflatable balloon. The balloon is secured to the catheter at the distal and proximal ends of the device. An inflation mechanism for providing a fluid into the area between the balloon and catheter is also provided. The balloon can be inflated during use with any inert fluid, such as saline, contrast fluid, air, or even low electrical conductivity sucrose solution. In embodiments where the electrically conductive wires are disposed on the inside of the balloon (between the balloon and the catheter) and where there is present a highly conductive fluid in the lumen (inside the balloon), the flow of the current would be preferentially through the fluid rather than through the wires which may result in a more diffuse electrical field. In preferred embodiments, a low-conductivity buffer is preferred as the fluid to inflate the balloon to more accurately treat target tissue.

The partially insulated conductive wires or electrodes provide for delivering the IRE electrical charge to target tissue from an electrical pulse generator. During use of the device, proximal ends of the wires/electrodes are in operable communication with a pulse generator. The wires can be hardwired directly to the pulse generator, or in preferred embodiments the electrode is equipped with a universal connector (or other connecting structure) for securing the electrically conductive wires/electrodes to the electrical pulse generator in an operably connective manner. For electrodes having a greater number of electrically conductive wires than the number of outputs available on a pulse generator it is desired to be used with, the electrodes and or pulse generator can be retrofitted or adapted accordingly to operably cooperate with one another. In embodiments, when there are more conductive wires on the electrode, e.g., 8 wires, than there are outputs on the pulse generator, e.g., 6 outputs, systems of the invention can comprise an electrode-generator interface that cooperates with the generator to switch which wires are active for a given pulse set in the overall sequence. More specifically, the interface can comprise a switch for switching between wires 4 and 8 for an 8-electrode system, since those wires would be least likely to be energized at the same time at 180° apart. Other examples for operation of an interface for treatments using basic 2-at-a-time pulsing pairs, the system can be connected to all 8 wires on the output, and just have a positive and negative input to take from the generator, where it would automatically switch pairs 1-2 to 2-3 and so on, while the generator's positive and negative outputs (port 1 and 2) would change pulse set 1 at (ex.) 2000 V (wires 1-2), then change to 1500 V (wires 2-3) for the second.

In this embodiment, the electrically conductive wires are elongated and are disposed along the length of the balloon. The wires are spaced a selected distance from one another around the circumference of the electrode. In FIGS. 1A-B, there are eight electrically conductive wires/electrodes circumferentially spaced around the balloon. The distal ends and proximal ends of the electrically conductive wires/electrodes are protected or encased by an outer insulative body, while a medial portion of the wires/electrodes is exposed to the atmosphere or vessel wall when implanted.

The distal tip of the balloon preferably includes a conical distal end to allow easy advancement through the vessel lumen. The conical distal end is preferably formed from or is in operable communication with a portion of the outer body of the device. The outer body of the device is an insulative encasing providing protection for the components of the device and for controlling the amount of exposure of the electrically conductive wires. Another portion of the outer body of the device provides for a proximal encasing disposed at the proximal end of the electrode. In embodiments, there is a gap or separation distance between the distal and proximal encasings or portions of the outer body. This gap or unprotected area of the electrode exposes the electrically conductive wires to the atmosphere.

A connector is disposed proximally of the balloon. The connector is hollow to allow movement with respect to the guidewire, and has an internal chamber that extends all the way back to the proximal ends of the balloon catheter that can carry fluids, such as physiologic saline or air or low electrical conductivity sucrose solution.

The balloon is attached to the connector. Running through the body/connector assembly is an array of 8 conducting 35 gauge wires (0.15 mm). These wires are insulated throughout the electrode apparatus until they reach the highly insulative balloon, after which they are exposed. In embodiments, the conducting wires can be attached to the proximal portion of the connector, but their distal ends are free and enclosed within the casing of the tip. This allows free expansion of the wires with inflation of the balloon. In other embodiments, the wires can be attached to the surface of the balloon and/or the distal ends of the wires attached to the distal tip, or distal outer body, or distal portion of the connector of the electrode. One example of an electrode balloon catheter is disclosed in U.S. patent application Ser. No. 12/413,332 filed Mar. 27, 2009 and entitled "Irreversible Electroporation Device And Method For Attenuating Neointimal", which is incorporated herein by reference.

During use with the electrode inserted into a blood vessel, when the balloon is inflated with a fluid, the electrodes (electrically conductive wires) are expanded, and placed into contact with the targeted neointimal tissue disposed within the inner circumference of the blood vessel. In the embodiment shown, the length of exposure of each electrode is about 5 mm. However, larger exposure lengths may be used to treat diffuse restenosis lesions. See Rajagopal, V. and S. G. Rockson, Coronary restenosis: a review of mechanisms and management, The American Journal of Medicine, 2003, 115(7): p. 547-553. In specific embodiments, the exposure length of the electrically conductive wires and thus the exposed portion of the electrode can range from about 0.1 mm to about 5 cm, such as from about 0.5 mm to about 3 cm, or from about 0.8 mm to about 2 cm, or from about 1 mm to about 1 cm, or from about 1.5 mm to about 0.5 cm, or from about 2 mm to about 10 mm, or from about 2.5 mm to about 7 mm, or from about 3 mm to about 6 mm, such as from about 3.5 mm to about 4mm, etc.

Figure 1C:
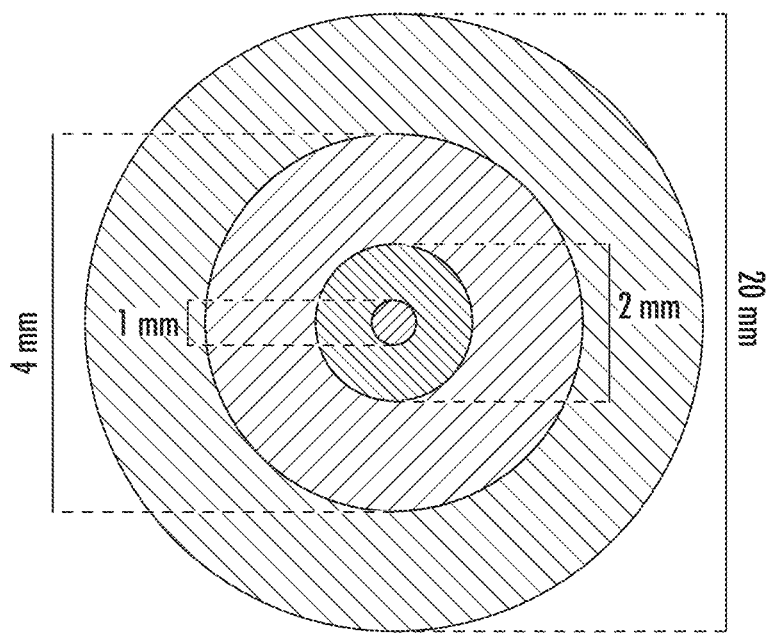
FIG. 1C is a schematic diagram representing the different layers and dimensions used in various numerical simulations of IRE in the coronary artery, in which (described from the innermost region to the outermost region) a catheter with electrodes, blood, plaque, and smooth muscle were modeled.
Figure 1D:
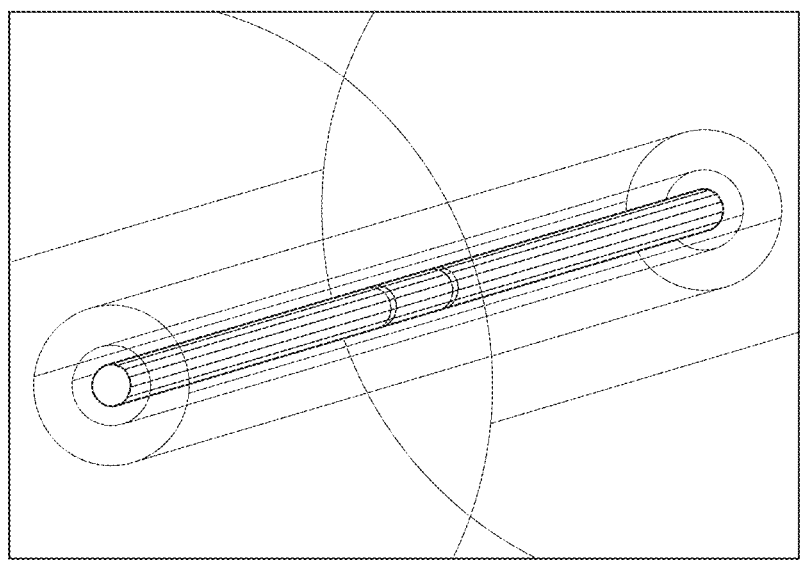
FIG. 1D is a schematic diagram of an electrode of the invention comprising a catheter type device with embedded electrodes at a longitudinal separation distance of 5 mm.

FIGS. 1C-D provide another device embodiment of the invention. In this embodiment, the electrodes can comprise electrically conductive wires that are longitudinally spaced a selected distance from one another along the circumference of the balloon. As shown in FIG. 1C, an electrode of about 1 mm in diameter can be inserted lengthwise into a blood vessel. For illustration purposes, the blood vessel here has an outer diameter of about 20 mm and, when healthy, an inner diameter of about 4 mm. As illustrated in this case here, however, there is plaque build up, stenosis, or restenosis in the blood vessel, leaving only about a 2 mm inner diameter for the flow of blood through the vessel. As shown, an IRE device according to the invention is inserted into the blood vessel and used to ablate all or a portion of the growth within the vessel that is obstructing blood flow. In embodiments, there can be multiple rings (instead of 2) spaced along the longitudinal length of the electrode, and the applied voltages between each ring-pair (2 conductive regions energized) or ring-set (>2 conductive regions energized at a time). Preferably, the IRE device is oriented rotationally within the blood vessel to deliver one or more electrical charge(s) to target tissue disposed only around a portion of the inner circumference of the blood vessel. To further illustrate placement of the electrode within a blood vessel, FIG. 1D provides a perspective view of an electrode device embodiment of the invention inserted lengthwise into a blood vessel with the electrically conductive wires disposed proximate target tissue.

Figure 1E:
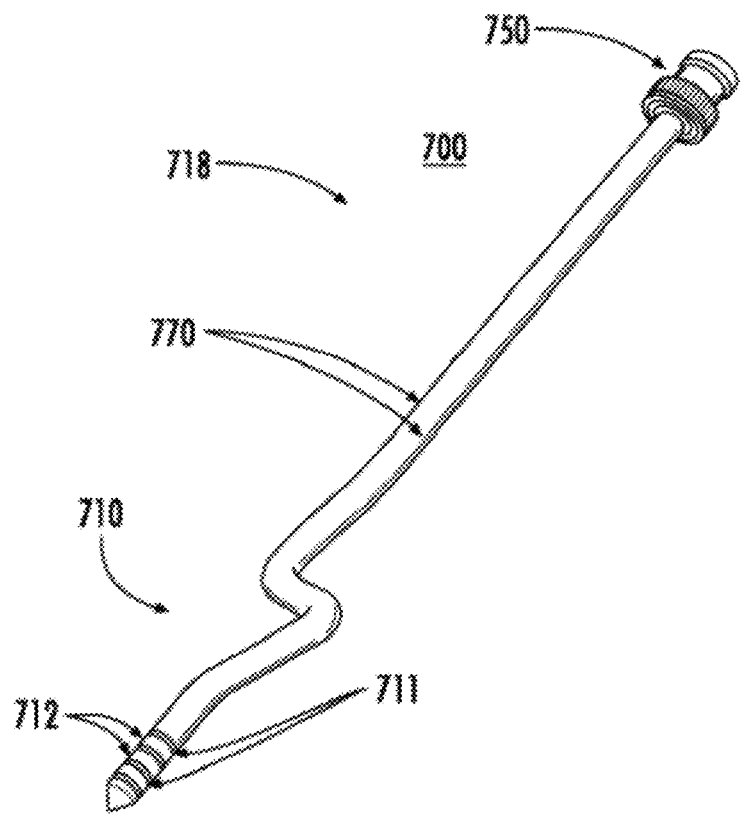
FIG. 1E is a schematic diagram illustrating an electrode embodiment of the invention which is a catheter type device with embedded electrodes that can be used for IRE treatment of neointimal hyperplasia.

FIG. 1E provides a representative example of another electrode configuration according to embodiments of the invention. Examples of other configurations that can be used are disclosed in US Published Patent Application No. 2010/0030211, filed Jun. 24, 2009; US Published Patent Application No. 2001/0044596, filed May 4, 2001; and US Published Application No. 2009/0247933, filed Mar. 27, 2009.

The device 700 illustrated here in FIG. 1E, provides a minimally invasive microsurgical tool that uses IRE in coronary arteries to treat neointimal hyperplasia. Generally, the electrode 700 is a catheter type device with embedded active 712 and ground 711 electrically conductive wires. The electrically conductive wires 711, 712 are annular in shape and are disposed lengthwise along the length of the distal tip 710 of the electrode 700. The conductive wires 711, 712 are spaced a selected distance from one another longitudinally along the length of the electrode 700 and are separated by sections of insulation. The electrode 700 is compatible with existing electroporation electronics and comprises a universal connector 750 for connecting the proximal end 718 of the electrode 700 in operable communication with an electrical pulse generator. Existing systems that can be used and/or adapted for use with devices and methods of the invention include the NanoKnife® system from AngioDynamics® of Latham, NY. A portion of the electrically conductive wires 711, 712 is encased within the outer body 770 of electrode 700, or electrically conductive leads run from the electrically conductive wires 711, 712 along the length of the electrode 700 from the distal tip 710 to the proximal end 718 for operable communication with an electrical pulse generator.

The electrically conductive wires can comprise any type of conducting metal, such as platinum/iridium. Different materials will have different radio-opacity and can be selected according to this characteristic to achieve a particular result. For example, silver is much more radio-opaque than titanium and thus some embodiments of electrodes of the invention can have titanium conductive surfaces/wires, while using silver for the markers. To ensure biocompatibility, embodiments of the electrode can be sheathed with an insulating polyurethane jacket 770 to enclose the electrically conductive wires leading to the electrical pulse generator. In embodiments, the electrical conducting wires do not need to be entirely conducting. For example, the electrical conductive surfaces can comprise a portion or portions with an insulating coating (especially near their base). The exposed portions or surfaces of the electrically conductive wires 711, 712 on the distal tip 710 can be any thickness and width. Likewise, the amount of separation distance between the electrically conductive wires at the distal tip 710 can be any amount, and the electrodes can comprise any number of conductive wires. In embodiments, the electrodes can be configured in a manner to provide for an adjustable separation distance between electrically conductive wires, and/or an adjustable amount of exposed conductive surface.

This embodiment is constructed as a thin device, which allows for easy navigation through the cardiovascular system directly into the treatment site. In embodiments where there is no guidance catheter placed first (as in FIG. 1E), the electrode can comprise a J-shaped tip (or similar shape) as is common in angioplasty and catheter-based interventions so as to enable guidance of the electrode through the vasculature to reach the target site. Such an asymmetric tip could also be used as a source for determining rotational orientation for this particular embodiment. The electrically conductive wires, separated by an insulating material, generate the electric field distribution that determines the IRE treated regions. Representative dimensions of the electrode device, such as about 0.5 mm in diameter, ensures that it is feasible to be placed in the coronary artery since it is smaller than those already used in catheterization. The diameter or width is thus on the order of 0.5 mm to 1 cm. Preferably, the diameter or width is about 0.5 mm to about 5 mm, such as about 1 mm, 2 mm, 3 mm, or 4 mm. The length of the device is not particularly limited, but is generally set such that a surgeon can use the device comfortably to treat lesions at any position in the body. Thus, for human use, the device is typically on the order of 40 cm or less in length, such as about 30 cm, 25 cm, or 15 cm, whereas for veterinary use, the length can be much larger, depending on the size of animal to be treated. For treatment of human brain tumors, the length can be on the order of 40 cm.

The device can be customized by varying the diameters and separation distances of the electrically conductive wires, thus unique IRE treated areas can be predicted using mathematical models. As a result, successful treatment for neointimal hyperplasia is ensured due to the ability to match different plaque sizes and shapes.

Further, in some embodiments, the IRE device, or a portion thereof, is flexible. A flexible device is advantageous for use in accessing lesions non-invasively or minimally invasively through natural body cavities. In embodiments where the device or a portion of it is flexible, the shape of the device can change based on contact with body tissues, can be pre-set, or can be altered in real-time through use of wires or other control elements, as known in the art, for example in use with laparoscopic instruments.

Smooth muscle cells are the primary component of the neointimal hyperplasia typical of in-stent restenosis. See Rajagopal, V. and S. G. Rockson, *Coronary restenosis: a review of mechanisms and management*, The American Journal of Medicine, 2003, 115(7): p. 547-553. In order to kill these cells without damaging the healthy vessel architecture, it is desirable to harness the non-thermal mechanism of IRE to kill cells without inducing thermal damage. Mitigating thermal damage allows the extracellular matrix, nerves, and other sensitive structures to be spared. This allows for healthy regrowth of the tissue.

The primary factor determining the effect of an electroporation procedure is the electric field to which the tissue is exposed. However, IRE protocols have a variety of electrical pulse parameters that may also affect the toxicity of the treatment. In addition to the electric field, these include pulse shape, number of pulses, pulse length, and repetition rate. The thermal effects of an IRE treatment during a pulse are a direct function of the conductivity of the tissue and the voltage to which it is exposed. Therefore, minimizing the thermal effects for a particular tissue type may be done by finding the minimum required electric field, and thus applied voltage, to kill the cells in the tissue.

To this end, pulsing parameters and electrode configurations according to embodiments of the invention can include any combination of any of the following: a pulse length in the range of about 1 μs to 1 ms; a number of pulses ranging from 1 to 10,000; an electric field distribution for each conductive wire pair and/or across a treatment region ranging from about 5-5,000 V/cm; a total electrical charge delivered by way of each conductive wire pair and/or across a treatment region of about 0.1 to about 500 mC; a frequency of pulse application ranging from about 0.001-100 Hz; a frequency of pulse signal ranging from about 0-100 MHz; a pulse shape that is square, exponential decay, sawtooth, sinusoidal, or of alternating polarity although the currently favored pulse shape is a biphasic DC pulse; a positive, negative, and neutral electrical charge pulses (changing polarity within the pulse); a resulting current in the treated tissue ranging from about 0 to about 100 amps; from 1-20 electrodes and/or electrically conductive wires; an electrode and/or electrically conductive wire separation distance ranging from about 0.1 mm to about 5 cm; and multiple sets of pulse/electrode parameters for a single treatment, including changing any of the above parameters within the same treatment, such as removing the electrodes and replacing them in different locations within the tissue or changing the number of electrodes, to specialize/customize outcome.

For example, in embodiments a pulse length in the range of about 1 µs to 1 ms, such as from about 5 µs to about 0.5 ms, or from about 10 µs to about 0.1 ms, or from about 15 µs to about 95 µs. Pulse lengths of 20 µs, 25 µs, 30 µs, 35 µs, 40 µs, 45 µs, 50 µs, 55 µs, 60 µs, 65 µs, 70 µs, 75 µs, 80 µs, 85 µs, 90 µs, 110 µs, 150 µs, or 200 µs, and so on are also acceptable. The number of pulses can range for example from 5 to 5,000, or from about 10 to 2,000, or from about 20 to 1,000, or from about 30 to 500, or from about 50 to 200, or from about 75 to 150, or from about 90 to 120, or from about 95 to 110, or about 100 pulses.

Typically, the electric field distribution for each conductive wire pair and/or across a treatment region for IRE is performed using voltages ranging for example between 1500 V/cm to 4,000 V/cm. Voltages of much lower power can also be used, including using less than about 1500 V/cm. Applied fields of about 500 V/cm to 1000 V/cm can be used, or even of about 10 V/cm to about 750 V/cm, such as from about 50 V/cm to about 200 V/cm, or an electric field distribution of about 75 V/cm to about 100 V/cm. For example, in the treatment of brain tumors, typically, an applied field of less than 1000 V/cm can be used. Electrical pulse generators that can be used include those capable of delivering from 0 to about 5,000 V, such as the NanoKnife® system of AngioDynamics®, which for example can deliver from 0-3,000 V.

In preferred embodiments, a total electrical charge delivered by way of each conductive wire pair and/or across a treatment region of about 0.5 to about 25 mC can be used, such as about 1 mC to about 20 mC, or from about 1.5 mC to about 15 mC, or from about 2 mC to about 10 mC, or from about 5 mC to about 8 mC, and so on. Similarly, in preferred embodiments, the resulting current in the treated tissue can range for example from about 1 A to about 8 A, or from about 2 A to about 6 A, or from about 3 A to about 5 A, such as 4 A. Indeed, for certain applications the total electrical charge delivered can range from about 0.5 to about 500 mC, such as about 10 mC to about 200 mC, or from about 15 mC to about 150 mC, or from about 20 mC to about 100 mC, or from about 50 mC to about 80 mC, and so on. The resulting current in the treated tissue can range for example from about 1 A to about 80 A, or from about 20 A to about 60 A, or from about 30 A to about 50 A, such as 40 A. It is not uncommon for currents for IRE treatments to reach or exceed 40 and 50 amps, and it is further feasible to operate under even higher current with pulse generators capable of operating under such conditions as well. Currents are expected to be high in certain applications, especially when working in an area where the tissue or the medium is highly conductive, such as with blood present in a blood vessel. Pulse width, pulse shape, number of pulses, and the resultant current in the tissue can be adjusted to achieve specific target goals for limiting the total electric charge, and any of the specific values disclosed in this specification can be used to calculate the target expected charge.

Any number of electrically conductive wires or electrodes can also be used. However, in preferred embodiments 3 to about 18 electrodes are used, such as 3 to 16, or from about 3 to 15, or from 4 to 12, or from 5 to 10, or from 6 to 8. Any one or more of the electrodes/wires can be selectively energized to achieve a particular treatment result. Further, the separation distance between electrically conductive surfaces, such as electrically conductive wires and/or electrodes, can range from about 0.2 mm to about 4 mm, such as ranging from about 0.3 mm to about 3 mm, or from about 0.4 mm to about 2 mm, or from about 0.5 mm to about 1 mm, or from about 0.8 mm to about 4 cm, such as from about 0.9 mm to about 3 cm, or from about 1.2 cm to about 2 cm, or from about 1.5 cm to about 1.8 cm, and so on.

The electric field needed for a particular situation may be predicted through numerical modeling, allowing for reliable treatment planning. See Davalos, R. V., L. M. Mir, and B. Rubinsky, Tissue Ablation with Irreversible Electroporation, Ann Biomed Eng, 2005, 33(2): p. 223-231; Robert E. Neal II and R. V. Davalos, The Feasibility of Irreversible Electroporation for the Treatment of Breast Cancer and Other Heterogeneous Systems, Ann Biomed Eng, 2009, 37(12): p. 2615-2625; and Edd, J. F. and R. V. Davalos, Mathematical Modeling of Irreversible Electroporation for Treatment Planning, Technol Cancer Res Treat, 2007, 6(4): p. 275-286. To determine the efficacy of the electrode and understand the effects of the pulses on tissue, a numerical model has been developed capable of simulating treatments. This was done using a finite element software package, COMSOL Multiphysics (COMSOL, Stockholm, Sweden).

Figure 2B:
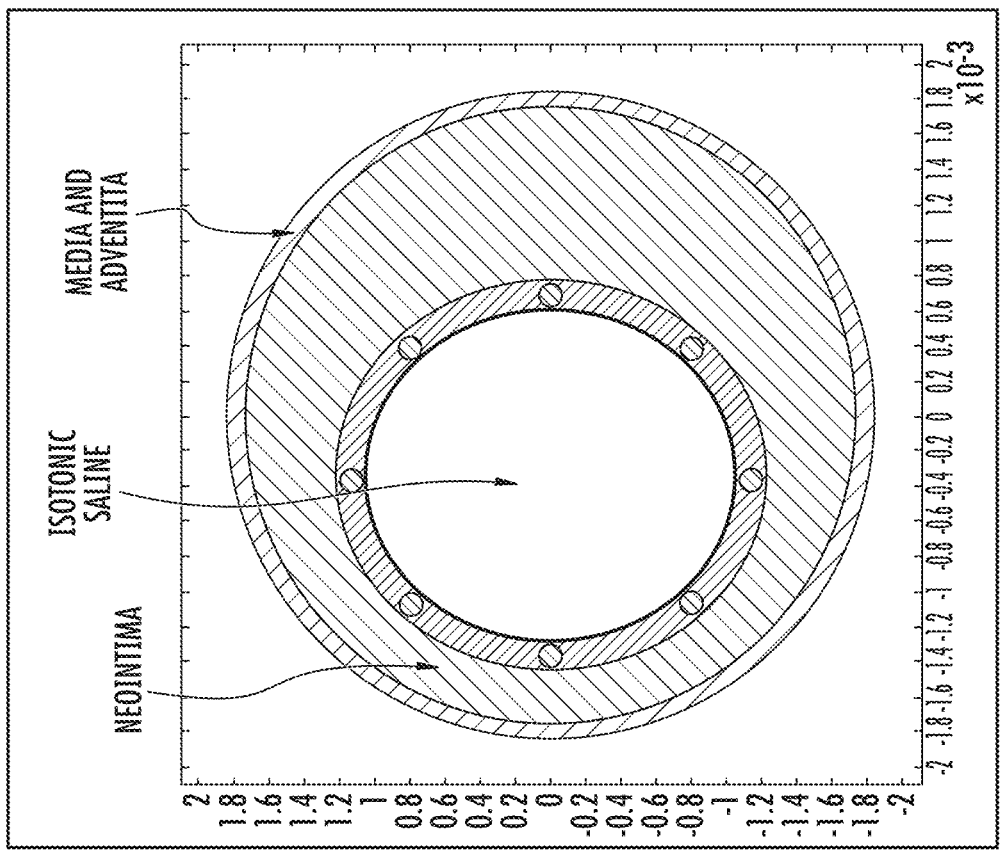
FIGS. 2A-B are schematic diagrams showing a cross-sectional view of a numerical model setup for symmetric restenosis (FIG. 2A) and asymmetric restenosis (FIG. 2B).
Figure 2A:
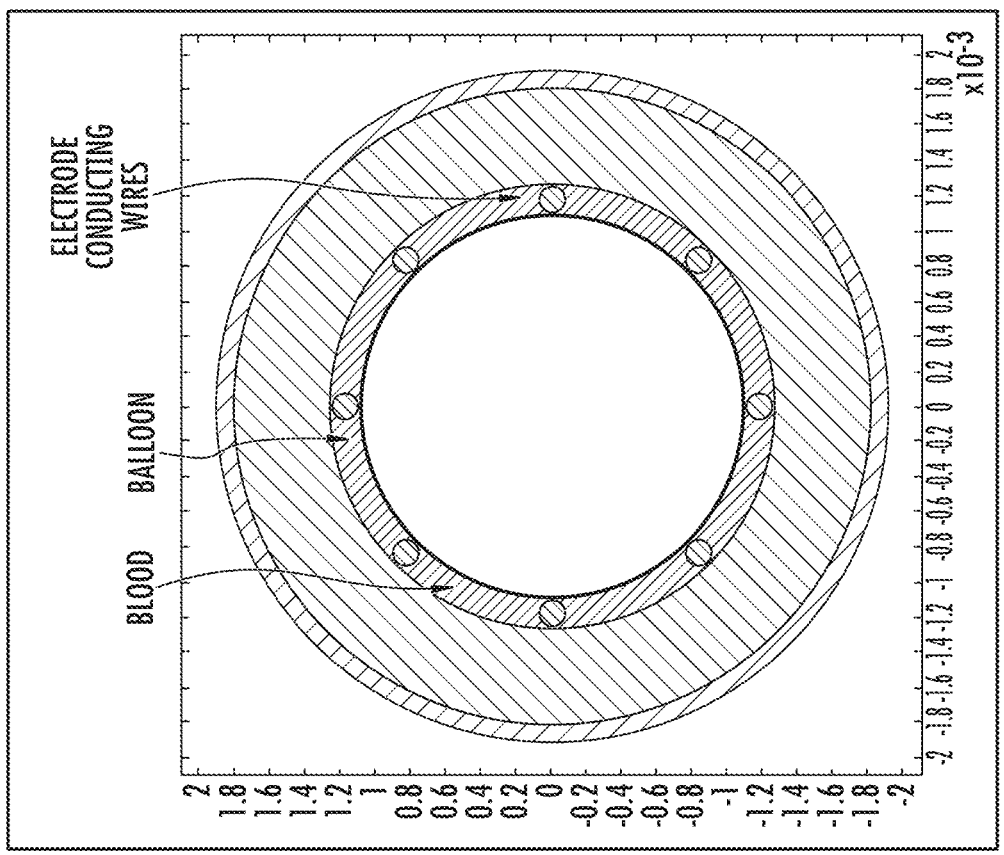

Two representative models were developed, simulating the cross section of a typical artery with a symmetric or an asymmetric restenosis. The model setups for the electrodes of FIGS. 1A-B are illustrated in FIGS. 2A-B.

In the numerical models illustrated, both use a blood vessel outer diameter of about 3.6 mm, with a combined tunica media and adventitia thickness of 200 µm, which are representative values derived from visual inspection of results from Maor, E., A. Ivorra, J. Leor, and B. Rubinsky, The Effect of Irreversible Electroporation on Blood Vessels, Technol Cancer Res Treat, 2007, 6(4): p. 307-312. These vessel layers are considered to be composed of collagen and elastin, as described in Saladin, K. S., The Circulatory System III-Blood Vessels, in Human Anatomy. 2008, Mcgraw-Hill: New York. p. 595-638.

The symmetric restenosis (FIG. 2A) assumed an equal amount of neointimal hyperplasia all around the vessel, reducing the luminal diameter to 2.5 mm, a cross-sectional reduction of 52% (stenosis of 48%). Inside the lumen, the model then contains a circular array of 8 electrode surfaces, each 0.15 mm in diameter, equally spaced around the neointimal tissue at 45° angles from the center, an angle switch of about 45 degrees. Inside the electrodes is a thin-walled balloon having an outer diameter of about 2.2 mm, modeled as rubber, and blood is assumed to be in the space between the balloon and the neointima. Inside the balloon is modeled as slightly hypotonic saline. The electrical and thermal properties of model components may be found in Table 1.

TABLE 1

Electrical and Thermal Properties Used in Numerical Modeling

| Property | Symbol | Tissue | Value | Units | Reference |
|---|---|---|---|---|---|
| Electrical Conductivity | $\sigma$ | Media and Adventitia | 0.25 | S/m | Carrara 2007 |
| | | Neointima | 0.2 | | Carrara 2007 |
| | | Electrodes | $4.032 \times 10^6$ | | Metals 1990 |
| | | Blood | 0.7 | | Carrara 2007; Duck 1990 |
| | | Balloon | $1 \times 10^{-13}$ | | Serway 1998 |
| | | Isotonic Saline (0.15M) | 1.39 | | Gabriel 2009 |
| Density | $\rho$ | Media and Adventitia | 1085 | kg/m$^3$ | Werner 1988 |
| | | Neointima | 1085 | | Werner 1988 |
| | | Electrodes | 7850 | | Metals 1990 |
| | | Blood | 1059 | | Werner 1988 |
| | | Balloon | 2.17 | | |
| | | Isotonic Saline (0.15M) | 1000 | | Kenner 1977 |
| Thermal Conductivity | k | Media and Adventitia | 0.55 | W/(m · K) | Werner 1988; Bhattacharya 2003 |
| | | Neointima | 0.50 | | Werner 1988 |
| | | Electrodes | 44.5 | | Metals 1990 |
| | | Blood | 0.50 | | Duck 1990 |
| | | Balloon | 0.23 | | |
| | | Isotonic Saline (0.15M) | 0.50 | | |
| Specific Heat Capacity | $c_p$ | Media and Adventitia | 3.20 | J/(kg · K) | Werner 1988 |
| | | Neointima | 3.72 | | Duck 1990 |
| | | Electrodes | 475 | | Metals 1990 |
| | | Blood | 3.84 | | Duck 1990 |
| | | Balloon | 385 | | |
| | | Isotonic Saline (0.15M) | 3.84 | | |

See Carrara, N. Dielectric Properties of Body Tissues, Italian National Research Council: Institute for Applied Physics, 2007 ("Carrara 2007") cited 2010, available from: http://niremf.ifac.cnr.it/tissprop/; see also Properties and Selection: Irons, Steels, and High-Performance Alloys, 10 ed. Metals Handbook, Vol. 1, 1990: ASM International ("Metals 1990"); see also Duck, F. A., Physical Properties of Tissue: A Comprehensive Reference Book, 1990, New York: Academic Press ("Duck 1990"); see also Serway, R. A., Principles of Physics, 2nd ed. Principles of Physics, 1998, Fort Worth, Texas; London: Saunders College Pub ("Serway 1998"); see also Gabriel, C., A. Peyman, and E. H. Grant, Electrical conductivity of tissue at frequencies below 1 MHz, Physics in Medicine and Biology, 2009, 54(16): p. 4863-4878 ("Gabriel 2009"); see also Werner, J. and M. Buse, Temperature profiles with respect to inhomogeneity and geometry of the human body, J Appl Physiol, 1988, 65(30): p. 1110-1118 ("Werner 1988"); see also Kenner, T., H. Leopold, and H. Hinghoferszalkay, Continuous High-Precision Measurement of Density of Flowing Blood, Pflugers Archiv-European Journal of Physiology, 1977, 370 (1): p. 25-29 ("Kenner 1977"); see also Bhattacharya, A. and R. L. Mahajan, Temperature dependence of thermal conductivity of biological tissues, Physiological Measurement, 2003, 24(3): p. 769-783 ("Bhattacharya 2003").

The representative numerical model was solved for the electric field distribution for a voltage of 400 V/cm. This was done either with all conducting surfaces energized in an alternating (V0-0-V0) fashion around the electrode, or with only two adjacent surfaces energized (one as V0 and one as ground). According to embodiments of the invention, any range of energized wire arrangements are possible (E1 at V0 and E3 at 0; or even E1 at V0, E4 at V0/3, and E7 at 0). Indeed, multiple electrodes can be energized while multiple others are set to ground. There is also no limitation on which electrodes can be energized and which are set to ground, which will depend on a particular treatment protocol being administered. FIGS. 3A-D show the resulting electric field distribution between 0 and 1500 V/cm, with a black contour at 637 V/cm, a typical IRE threshold taken from the literature. See Miklavcic, D., D. Semrov, H. Mekid, and L. M. Mir, A validated model of in vivo electric field distribution in tissues for electrochemotherapy and for DNA electrotransfer for gene therapy, Biochimica et Biophysica Acta, 2000, 1523: p. 73-83.

Figure 3A:
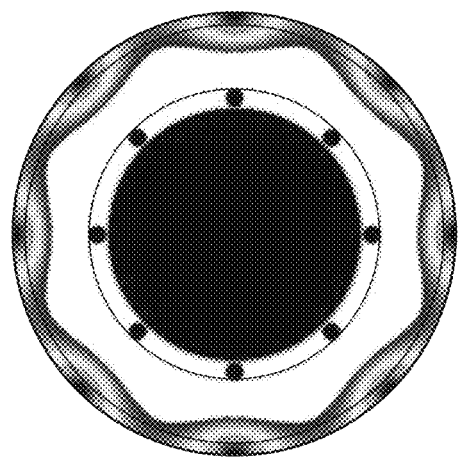
FIGS. 3A-D are schematic drawings illustrating a cross-sectional view of a representative numerical model output of electric field following a 100 μs pulse at 400 V, and more particularly: for treating symmetric restenosis with all 8 wires energized (FIG. 3A); for treating symmetric restenosis with 2 wires energized (FIG. 3B); for treating asymmetric restenosis with all 8 wires energized (FIG. 3C); and for treating asymmetric restenosis with 2 wires energized (FIG. 3D).
Figure 3B:
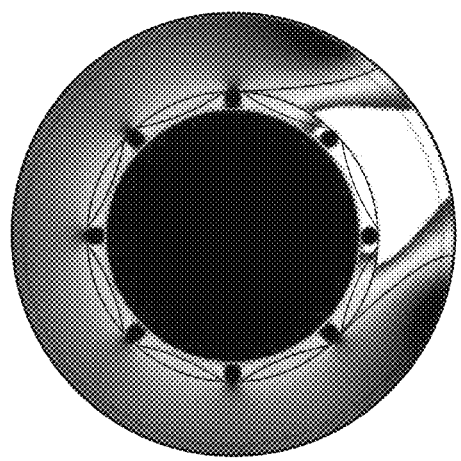
Figure 3C:
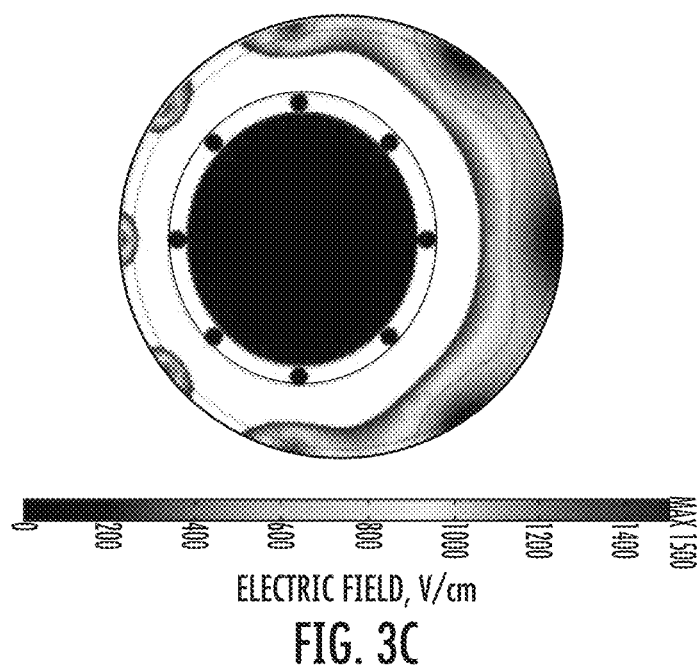
Figure 3D:
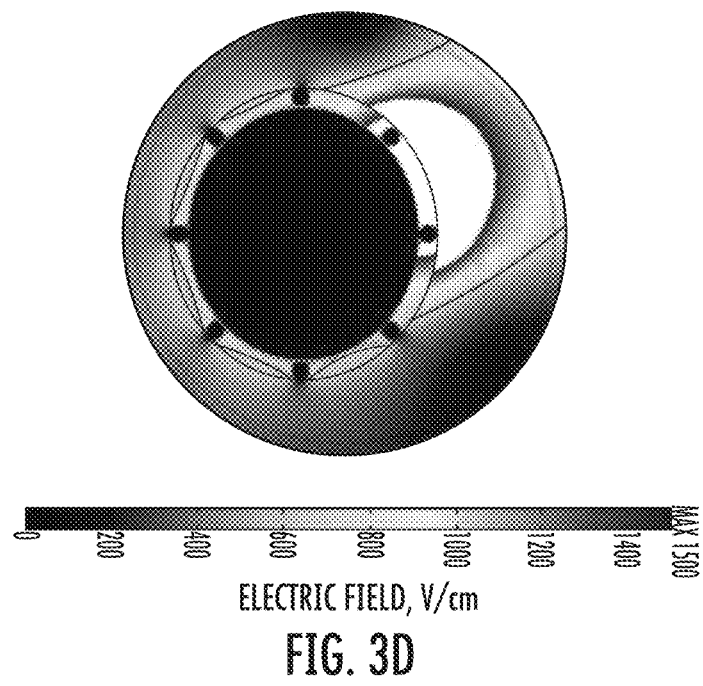

The representative numerical model output of electric field (FIGS. 3A-D) and temperature (FIGS. 3E-F) is illustrated following a 100 μs pulse at 400 V. More particularly, FIG. 3A illustrates treatment of symmetric restenosis with all 8 wires energized, while FIG. 3B illustrates treatment of symmetric restenosis with only 2 wires energized. Likewise, treatment of asymmetric restenosis with all eight wires energized is shown in FIG. 3C, while treatment of asymmetric restenosis with only two wires energized is shown in FIG. 3D. The black contour line shown in FIGS. A-D is 637 V/cm.

Figure 6A:
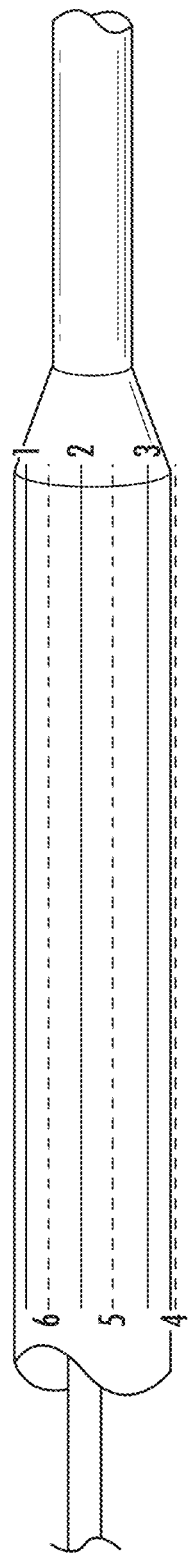
FIG. 6A is a schematic diagram of a balloon type catheter electrode comprising a plurality of electrically conductive wires disposed longitudinally over the length of the balloon.
Figure 6B:
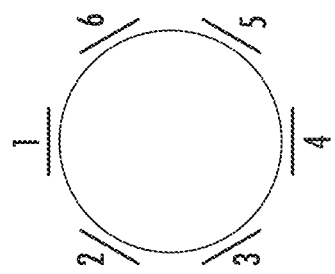
FIG. 6B is a schematic diagram showing a cross-sectional view of the electrode illustrated in FIG. 6A comprising a radio-opaque marker disposed proximate each wire.

It is important to note that the devices of the invention can comprise any number of electrically conductive wires disposed in any manner on the electrode. In methods of the invention, any number of electrically conductive wires can be energized in any order and in any combination. For example, for an electrode having ten electrically conductive wires disposed around the circumference of the electrode and spaced circumferentially or longitudinally from one another and progressing upwardly in number order from 1 to 10, the wires can be selectively energized using all, or less than all of the wires around the circumference of the electrode or along the length of the electrode. Referring to FIG. 6A-6B, in such embodiments, wires 5 and 6 can be energized, then wires 2 and 4 energized, then wires 3 and 5 energized to treat a target region disposed proximate the area near electrodes 2-6. This leaves the area or substantially most of the area proximate wires 6 to 1 untreated.

Referring back to FIGS. 3A-3F, when all the wires of the 8-wire electrode were energized, it was found that only the corners of the outermost regions of the neointimal hyperplasia were not treated with 637 V/cm in the symmetrical stenosis; while there is a large gap at the expanded side in the asymmetrical case. In order to effectively treat the entirety of the asymmetrical stenosis, significantly larger voltages should be used. Since previous designs would have to energize all the conducting surfaces equally, the region of tissue exposed to IRE would likely expand beyond the vessel, possibly affecting healthy tissues, which highlights insufficiencies of previous catheter-based electrode designs regarding non-cylindrical stenoses.

Notably, when two adjacent wires were energized, the treatment margins of IRE (presumed at 637 V/cm) extend easily through the local neointimal tissue. This shows that lower voltages may be used if pairs of electrodes are energized in succession rather than simultaneously. Furthermore, treating in this way allows for a practitioner to finely tune the applied voltage for each sequence, locally extending treatment regions at thicker regions of restenosis while decreasing treatment margins at thinner regions. From the determination that a lower voltage is required when only two electrodes are energized at a time, it can clearly be seen how the proposed model may be used to investigate the effects of various treatment parameters in order to optimize treatments to be used in clinical and pre-clinical settings.

Figure 3E:
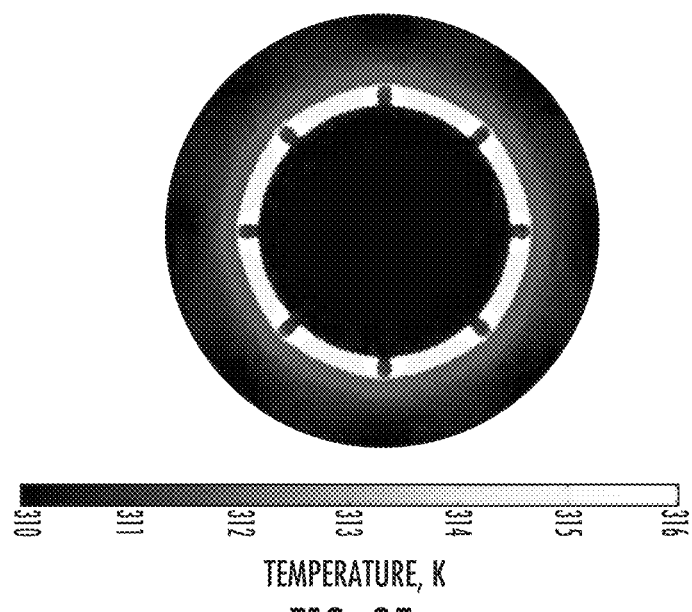
FIGS. 3E-F are schematic drawings illustrating a cross-sectional view of a representative numerical model output of temperature following a 100 μs pulse at 400 V, and more particularly: for treating symmetric restenosis with all 8 wires energized (FIG. 3E) and with only 2 wires energized (FIG. 3F).
Figure 3F:
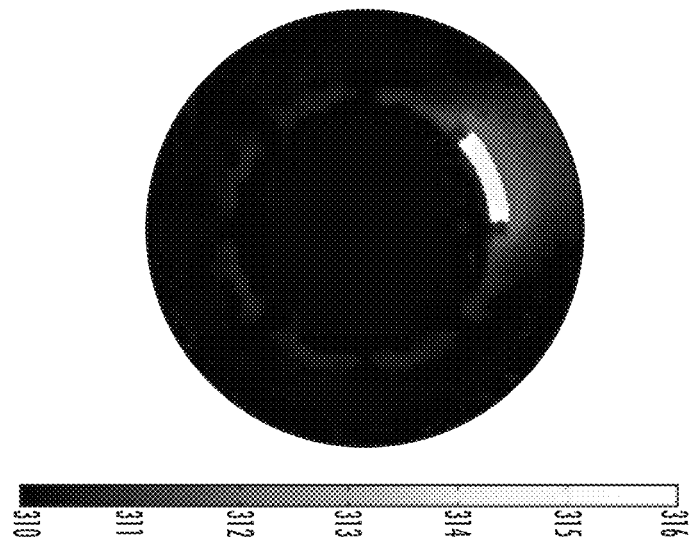

The electric potentials used to generate the electric fields used in IRE also cause Joule heating of the tissue. This is a function of the electric potential to which a bulk of tissue is exposed, its electrical conductivity, and the time for which it is exposed. The thermal effects of catheter type IRE are illustrated in FIGS. 3E-F. Representative numerical models for temperature output are illustrated for treatment of symmetric restenosis using all eight wires energized (FIG. 3E) and using only two wires energized (FIG. 3F). In order to accomplish complete IRE ablation of a targeted region without damaging the extracellular matrix and other sensitive structures, a comprehensive quantitative understanding of the thermal effects from a treatment protocol is vital. By numerically modeling these effects, one is able to determine the potential for any thermal damage to the tissue structures and adjust treatment plan protocols prior to application in order to minimize or eliminate this undesired form of potential damage. Therefore quantitative modeling of the thermal effects will be done through utilization of the numerical model previously described for understanding electric field behavior.

More particularly, the thermal behavior of tissue may be assessed using a modified Pennes Bioheat equation with the addition of a Joule heating term as outlined below:

$$\nabla(k\nabla T) + w_b c_b (T_a - T) + q''' + \sigma|\nabla\Phi|^2 = \rho c_p \frac{dT}{dt} \quad (1)$$

where k is the thermal conductivity of the tissue, T is the temperature, $c_b$ and $c_p$ are blood and tissue heat capacity, respectively, $w_b$ is blood perfusion, $T_a$ is arterial temperature, $\rho$ is tissue density, $\sigma|\nabla\Phi|^2$ is the joule heating term, and $q'''$ is metabolic heat creation. The outer vessel boundary was treated as adiabatic. See Davalos, R. V. and B. Rubinsky, Temperature considerations during irreversible electroporation, International Journal of Heat and Mass Transfer, 2008, 51(23-24): p. 5617-5622. Because the time scale of the electroporation pulses (microseconds) is much lower than those involved in metabolic heat generation and blood flow (see Werner, J. and M. Buse, Temperature profiles with respect to inhomogeneity and geometry of the human body, J Appl Physiol, 1988, 65(30): p. 1110-1118; and Gautherie, M., Y. Quenneville, and C. M. Gros, Metabolic heat production, growth rate, and prognosis of early breast carcinomas, Biomedicine, 1975, 22: p. 328-336), one is able to see that the dominant terms affecting change in temperature for a volume of tissue is the contributions of heat conduction from neighboring tissues and electroporation pulse induced Joule heating.

By eliminating the blood perfusion and metabolic heat generation terms and rearranging the terms, the equation becomes:

$$\frac{dT}{dt} = \frac{\nabla(k\nabla T) + \sigma|\nabla\Phi|^2}{\rho c_p} \quad (2)$$

For a single pulse of infinitely small duration, δt, the change in temperature may be described by:

$$dT = \frac{\nabla(k\nabla T) + \sigma|\nabla\Phi|^2}{\rho c_p} dt \quad (3)$$

From the modified Pennes' Bioheat equation above, it becomes evident that the controllable terms affecting electroporation-induced temperature changes are the magnitude of the electric field and the duration of the pulse. Assessment of thermal effects from the model would allow one to adjust the protocols to prevent thermal damage and understand its impact on the electric field distribution. For instance, the pulse length could be shortened, a low-conductivity gel could be injected into the tissue, or an actively-cooled electrode could be used to cool the tissue prior to and during pulsing.

The representative numerical model of FIGS. 3A-F has been evaluated for the temperature distribution resulting from a single 100 μs pulse. The initial condition for the temperature of the entire tissue was taken to be 310.15 K (37° C.), which is the physiological temperature. FIGS. 3E-F show the results when a voltage of 400 V was applied to the symmetric stenosis for the case of eight and two energized surfaces. From this, it can be seen that only a very small portion of blood near the electrodes reaches temperatures above 314 K, a change of 4 K. In addition, most of the thermal effects occur in the blood between the energized surfaces, with very little noticeable effect to the neointimal tissue.

To evaluate potential thermal damage, the maximum temperature could be compared to a typical threshold of protein denaturation and scarring of 50° C. (323 K). See Diller, K. R., Advances in Heat Transfer, in Bioengineering Heat Transfer, Y. I. Choi, Editor, 1992, Academic Press: Boston. p. 157-357. Because 316 K falls well below this temperature threshold, it is clear that the treatment protocols used in the first part of this numerically modeled example are able to fully treat the targeted region without inflicting thermal damage. It should be noted that thermal damage may occur at temperatures below 50° C. when carried out over a long period of time (such as hours, for example), and that the combined effects of many pulses may further increase the temperatures. However, for the current example of the numerical model outlined above, it may be assumed that the high perfusion rate of blood in an artery will rapidly dissipate the heat generated. In embodiments, however, where the balloon is inflated blood flow within the blood vessel may be greatly reduced or completely blocked and heat dissipation may occur in some other manner. This, in addition to the relatively long span between pulses (for example, meaning 0.25 seconds as compared to 0.0001 seconds of a 100 µs long pulse); allows one to expect that the temperature will return to physiologic temperatures prior to the next pulse, preventing it from ever exceeding the 50° C. threshold.

Figure 4:
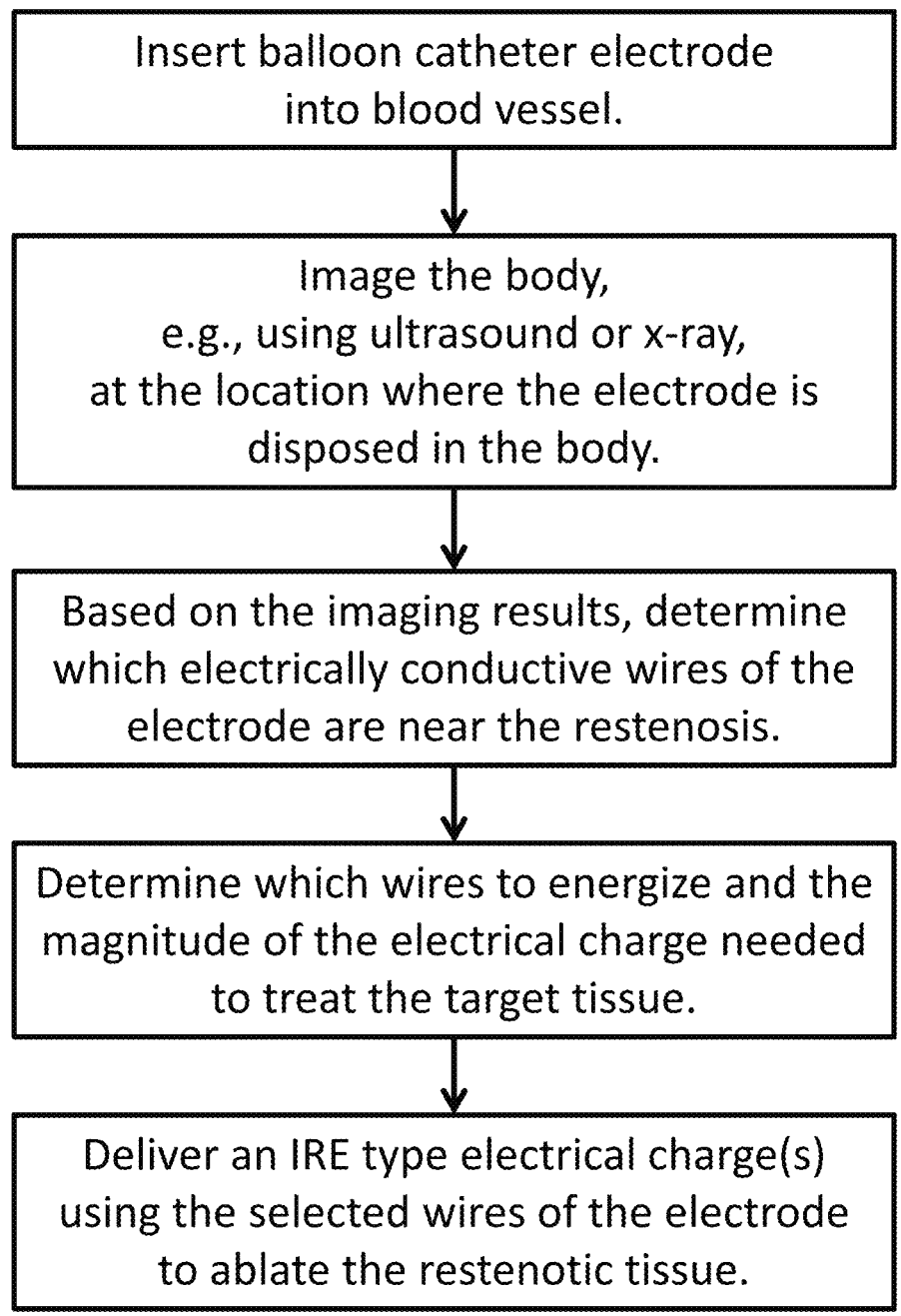
FIG. 4 is a flowchart illustrating a method of selectively energizing one or more electrically conductive wires of an electrode for treating target tissue.

A method of selectively ablating asymmetric restenosis is illustrated in FIG. 4. Such methods can involve one or more of the following: inserting a balloon catheter electrode in a blood vessel; imaging the body in which the catheter is placed, for example, using ultrasound, x-ray, CT, MRI, etc.; based on the imaging results, determining which electrically conductive wires of the electrode are near the restenosis; determining which wires of the electrode to energize and the magnitude of the electrical charge needed to treat the target tissue; and delivering an IRE type electrical charge(s) between the selected wires of the electrode to ablate the restenotic tissue. These method steps can be used singularly or one or more together with other methods and/or method steps described in this specification. One of skill in the art will know how to modify the methods according to a particular result to achieve.

Methods of the invention can also include the capability of being able to synchronize the electrical pulses with the cardiac rhythm of the patient to avoid arrhythmia. This is especially important for treatments administered on coronary arteries, e.g., directly at the heart, where chances of arrhythmia are highest. In addition, treatment of arrhythmogenic regions of the heart from the inside is yet another application for the asymmetric ablation protocols of the present invention. In some situations, it is feasible that such treatments could be used in lieu of open heart surgery.

Preferred methods of embodiments of the invention are directed to electrically ablating tissue, with the method comprising: inserting into a vessel an electrode having a plurality of electrically conductive wires disposed lengthwise along the electrode and circumferentially spaced a selected distance from one another; orienting the electrode within the vessel to provide one or more of the electrically conductive wires in position to deliver one or more electrical pulse to target tissue; selecting one or more but less than all of the electrically conductive wires for administering the electrical pulse(s); administering the electrical pulse(s) from the selected electrically conductive wires to deliver the electrical pulse(s) to the target tissue and less than all vessel circumference; and wherein the administering is performed for a time and under circumstances sufficient to cause irreversible electroporation of the target tissue or a portion thereof.

Methods of the invention can also be used for reversible electroporation of tissue to assist or enable electrochemotherapies and/or electrogenetherapies. Even further, aspects of methods of the invention include inserting the electrode device into any organ or vessel which is not in particular a blood vessel, such as within the lymphatic system for treating undesired tissue such as lymphoma. Even further, the electrodes can be used in arrhythmogenic regions of the heart or tumor nodules in the lungs, which can be accessed through vessels of the respiratory tract such as bronchial tubes or blood vessels.

Methods of the invention can employ an electrode comprising a flexible catheter and inflatable balloon with the electrically conductive wires disposed lengthwise along and circumferentially spaced around the electrode, such as on a surface of the inflatable balloon.

In embodiments, the electrically conductive wires can be selectively energized, especially in a sequential manner across only a portion of the circumference of a blood vessel or other treatment area. For example, in embodiments where an electrode comprises eight electrically conductive wires, the method can comprise orienting only a portion of the wires proximate a target treatment area, such as wires 1, 2, and 3 of the eight-wire system. A selected number of pulses at a selected electrical charge can be administered between wires 1 and 2, then a selected number of pulses at a selected electrical charge (which may be different or the same as that applied between wires 1 and 2) may be delivered between wires 2 and 3. Then this pattern or a different pulsing protocol can be administered selectively and sequentially using selected wire pairs. In preferred embodiments, less than all of the wire pairs are used and less than all of the circumference of the electrode is energized during a treatment. In this manner, less than all of the surface area of a blood vessel can be subjected to the IRE.

More particularly, for example, 10 pulses of 50 µs in length at 500 V/cm can be delivered between a first selected electrically conductive wire pair, then 100 pulses of 100 µs in length at 2500 V/cm can be delivered using a second wire pair, then 50 pulses at 75 µs in length at 1000 V/cm can be administered using a third wire pair. This sequence of pulsing can then be repeated any number of times until a desired treatment outcome is reached. Alternatively, any one or more of the pulsing parameters can be changed during the treatment to modify the effect the pulsing protocol is having on the tissue. For example, a second round of pulsing using the first, second, and third wire pairs can be administered by changing the parameters for the third wire pair, such as by delivering 20 pulses that are 90 µs in length at 1500 V/cm. This round of pulsing protocols, or combinations of the protocols, can then be continuously and sequentially administered until a desired treatment result is achieved. By energizing only a portion of the circumference of the electrode (only the first, second, and third wire pairs), only a portion of a selected region of the body that surrounds the electrode, such as a portion of a blood vessel, is subjected to the IRE thus rendering the non-targeted regions unaffected. Changing parameters impacts the depth of IRE ablation. Accordingly, the treatment can be customized to ensure complete treatment of thicker stenotic segments without over-treating regions with shallower stenotic segments.

Figure 5:
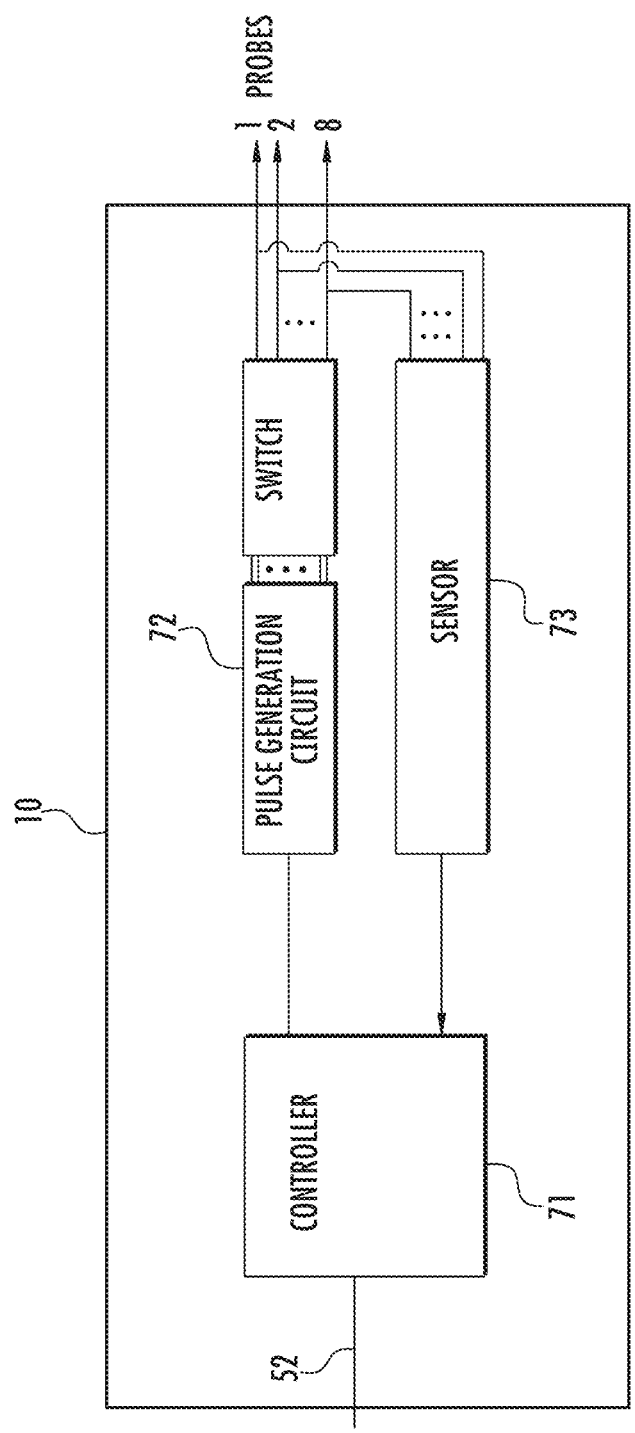
FIG. 5 is a schematic diagram of a representative electrical circuit for an electrode system of the invention, which circuit enables selective electrode energizing.

FIG. 5 is a schematic diagram illustrating a representative electrical circuit for an electroporation system according to embodiments of the invention. More particularly, FIG. 5 provides a schematic of an electrical circuit for an electroporation system, the system comprising a plurality of electrically conductive wires (electrodes) or solutions with high electrical conductivity (blood); a pulse generator and sensor(s) in operable communication with the probes; and a controller or control system in operable communication with the pulse generator and sensor(s). The controller in operable communication with the other components of the system together provide for a system capable of selective electrode energizing. The electrical circuit 10, in particular, comprises an electrical connection with a power source for delivery of electrical energy to the controller 71. The controller 71, alone or in combination with sensor(s) 73, in turns provides power to the pulse generation circuit 72. The pulse generation circuit 72 is in operable communication with a switch for delivering the electrical energy to one or more, all, or less than all of the probes. The switch is operably configured to selectively deliver electrical energy to the probes in any manner. In preferred embodiments, the switch is capable of providing electrical energy sequentially to each of the probes over the entire circumference of the electrode, or over only a portion of the circumference of the electrode. Likewise, the switch is capable of providing electrical energy to a single probe, or more than one probe, or combinations of any two probes, in combination with any pulse protocol using any number, or length, or intensity of electrical pulses. The switch and pulse generator are operably connected with any number of probes. Here, up to eight probes or electrically conductive wires are illustrated for this representative system.

As shown in FIGS. 6A-G, other aspects of embodiments of the invention include devices and methods for determining the identification, location and/or orientation of the electrode and/or electrically conductive wires when inserted into the body, and especially with respect to the location of target tissue, including asymmetrical stenosis in a blood vessel.

A representative embodiment is provided in FIGS. 6A-G. By equipping devices and systems of the invention with one or more imaging markers, the overall rotational orientation of the electrode as disposed in a body or vessel can be determined. As shown in FIG. 6A, an angioplasty balloon type catheter electrode can comprise six electrically conductive wires disposed longitudinally over the length of the electrode and circumferentially spaced a selected distance from one another around the circumference of the catheter or electrode. FIG. 6B, shows brief radio-opaque plugs (such as silver) provided on or in connection with one or more or all of the electrically conductive wires of the electrode. Here, an imaging marker is associated with each of the electrically conductive wires and is disposed in the electrode in a manner to provide the plugs progressing clockwise/counter-clockwise around the wires of the electrode. The schematic of FIG. 6B provides a cross-sectional view of the device illustrating placement of the imaging markers in connection with the electrically conductive wires.

Although a 6-wire system is provided in FIGS. 6A-G, the approach could be used with any number of wires by altering the angle switch from each. In the context of this specification, the term "angle switch" is meant to refer to the angular distance of separation between electrically conductive wires around the circumference of the electrode. For example, an electrode with four wires would have an angle switch of about 90 degrees between wires, while an electrode with six wires has an angle switch of about 60 degrees. In preferred embodiments, electrodes of the invention comprise any number of electrically conductive wires ranging from 1 to 20, such as from 2-10, or from 4-8, or even from 5-6 wires. The wires can also be disposed in any orientation relative to the electrode, such as circumferentially and longitudinally spaced a selected distance from one another; or disposed longitudinally and spaced circumferentially a selected distance from one another; or the electrically conductive wires can be disposed in a spiral or helical manner around the circumference of the electrode.

Additionally, or alternatively, proximal and distal imaging markers can be provided at one or both ends of the electrode device. In preferred embodiments, the proximal and distal markers can comprise a radio-opaque material with an overall annular shape for disposing each imaging marker around the circumference of the electrode/catheter (to give a definitive start and finish).

With the electrode device inserted into the body of a patient, the region of the body where the device is disposed can be imaged, for example, using x-ray, ultrasound, MRI, CT, or angiography, for example. Depending on the shapes that show up on angiography/x-ray, the orientation of the electrode within the body can be determined, especially its rotational orientation within a blood vessel and relative to a stenotic region. In embodiments, any number of imaging markers can be used, such as from 1-25 and any number in between. In preferred embodiments, at least two markers are used, such as one marker to denote each electrically conductive wire. By measuring the 2D distance from one imaging marker to the next as revealed on an imaging modality, the rotation of the electrode can be determined.

Further, in embodiments, a differential echogenicity (extra bright/dark in ultrasound) can be placed at the distal tip and proximal portions at one or more specific electrically conductive wires so that the marker could be picked up on intravascular ultrasound (IVUS). Using these approaches, it is relatively easy to see wire orientations relative to any asymmetrical stenoses or other targets.

Figure 6C:
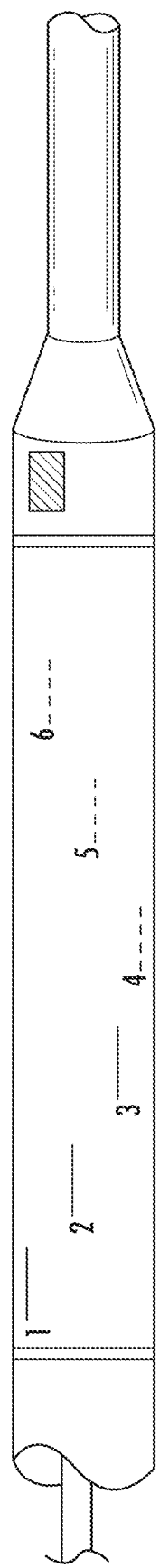
FIG. 6C is a schematic diagram illustrating markers disposed on a balloon type catheter electrode which would appear on an imaging apparatus, such as ultrasound, CT or X-ray, for identification/determination of the electrically conductive wires on the electrode.

FIG. 6C illustrates an electrode embodiment of the invention comprising six electrically conductive wires, each with an associated imaging marker disposed on, proximal to, or in connection therewith. In this embodiment, the imaging markers for the electrically conductive wires are radio-opaque plugs disposed in a counterclockwise progressive manner, which are used to denote the location of each wire. Proximal and distal end imaging markers are also included, which show where the wire imaging markers begin and end. Optionally included is a hyperechoic slug disposed in association with wire 1. As illustrated, represented is the expected x-ray image of the balloon catheter electrode of FIG. 6A inserted in a body and disposed within the vessel in a plane parallel to the drawing sheet.

Figure 6D:
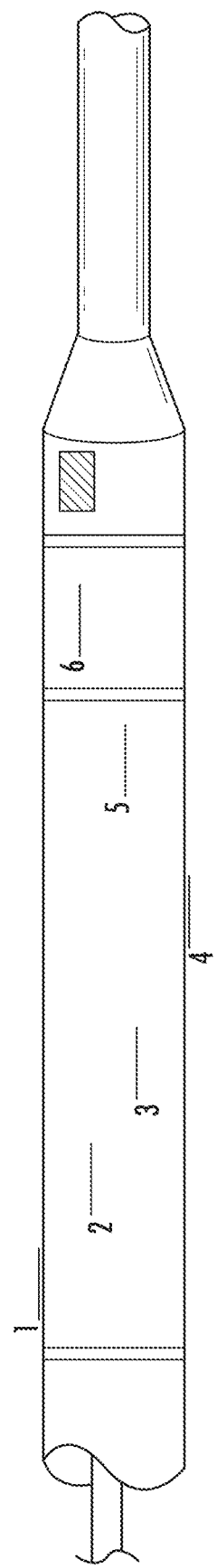
FIGS. 6D-G are schematic diagrams illustrating orientation of the markers comprised in a balloon type electrode, which is shown at various orientations within a body.
Figure 6E:
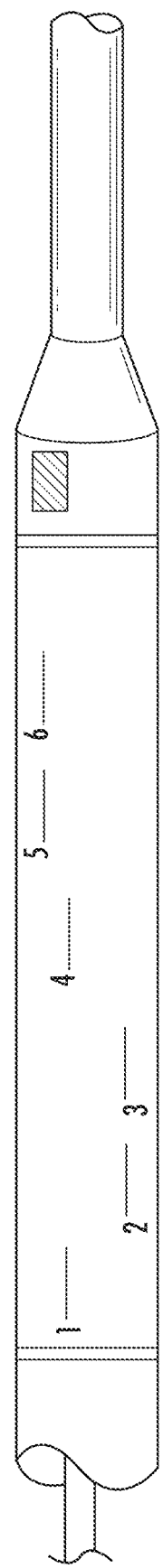
Figure 6F:
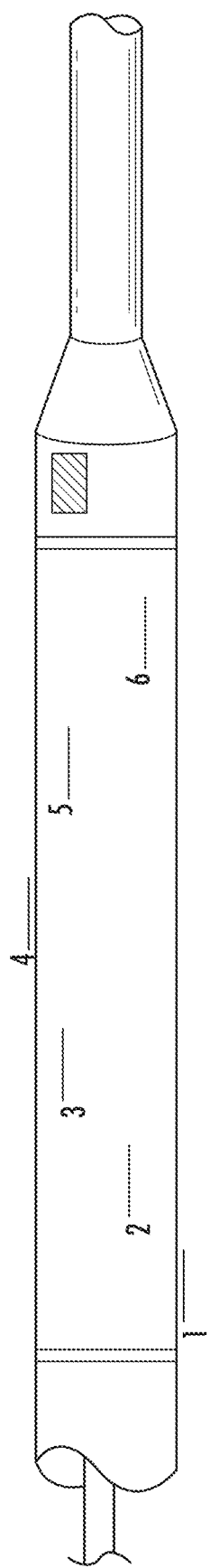
Figure 6G:
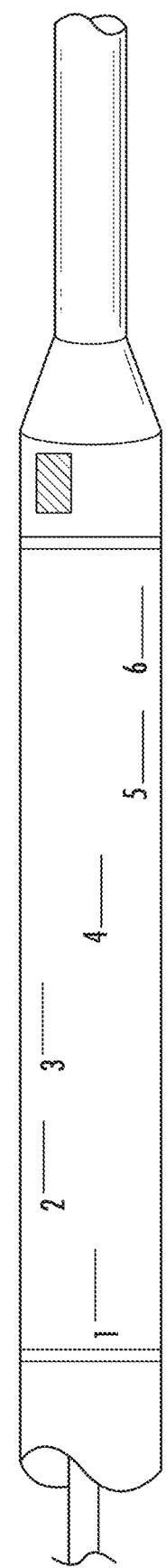

FIGS. 6D-G provide representative x-ray images of the electrode disposed at a rotational orientation relative to that shown in FIG. 6C. More particularly, as shown in FIG. 6D, the image illustrates the balloon catheter disposed in a body in same orientation as shown in FIGS. 6A and 6C. The representative x-ray image of FIG. 6E, indicates the balloon catheter electrode is oriented in the body with wire 1 oriented up toward and closest to the imaging device. Further, the orientation of the device of FIG. 6E is rotated upward out of the plane of the drawing sheet and 90 degrees relative to the position shown in FIGS. 6A, 6C, and 6D. If the device were then rotated another 90 degrees upward from the position shown in FIG. 6E, the imaging markers would be arranged as illustrated in FIG. 6F. Similarly, FIG. 6G shows rotation of the device another 90 degrees upward from the position shown in FIG. 6F, with marker 1 farthest from the imaging device, thus indicating wire 1 is 180 degrees rotated from the source of the imaging device.

Another embodiment can comprise a radio-opaque spiral rotating in a certain direction from a specific wire. The direction where it rotates from and ends on would give an exact orientation of the catheter.

In yet other embodiments, it is possible to use the wires themselves to identify which are the closest to the restenosis site for purposes of determining which electrodes to energize to treat a targeted area within the vessel. For example, using an electrical charge, a non-electroporating test signal (AC or DC pulse or pulses) can be injected between a pair of wires. Then, the electrical characteristics of the tissue lying between the electrode pair can be measured. The electrical characteristics measured can include, for example, resistance, impedance (complex impedance which includes real and imaginary parts), electrical impedance tomography, and so forth. The measured characteristics of healthy tissue will be different from that of restenotic tissue. The measured characteristics can thus be compared with threshold electrical characteristics determined by experiment, such as shown in U.S. Pat. No. 7,742,795, issued Jun. 22, 2010 to Minnow Medical Inc., incorporated herein by reference.

FIGS. 6H-M illustrate another of many potential ways to determine exact rotational orientation of the catheter electrode to ensure that differential targeting occurs in the desired region of the blood vessel. This example provides an 8-conducting wire electrode with a simple system of 2 radiopaque markers oriented 90 degrees apart (wires 1 and 3 ). The system would be appropriate for use with angiography, and the markers could be placed on the balloon below the electrodes, using a more radiopaque marker than the conducting wires themselves, such as silver. Including a circumferential marker in the device ensures starting at the correct wire (more useful for applications such as if every wire were to have a marker).

As shown, the imaging markers in this embodiment are different sizes to identify each marker and differentiate between the two. Here, wire 1's marker is long and wire 3's marker is short. This configuration allows the markers to overlap in length so the distance between the two can be easily measured to get an exact angle of rotation. A schematic providing a cross-sectional view and a side view of the device as it would appear as an image on an imaging device is shown in FIG. 6H. It is noted that in FIGS. 6H-M that the illustrations are not intended to represent exactly how the images would actually look on for example angiography (because more radiopaque materials show up darker), rather the schematics are intended to show how the position of the markers would identify the orientation of the device.

Figure 6J:
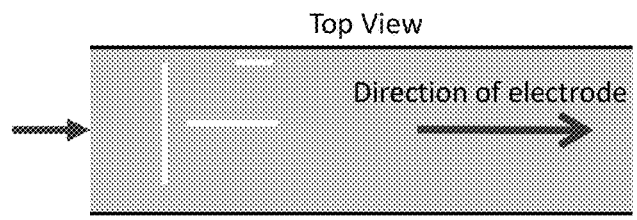
Figure 6J:
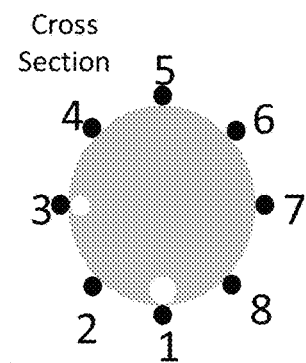
Figure 6K:
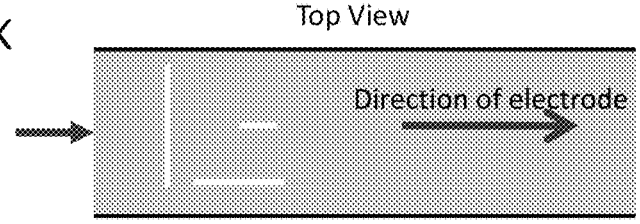
Figure 6K:
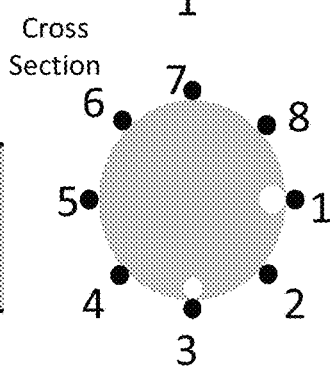
Figure 6L:
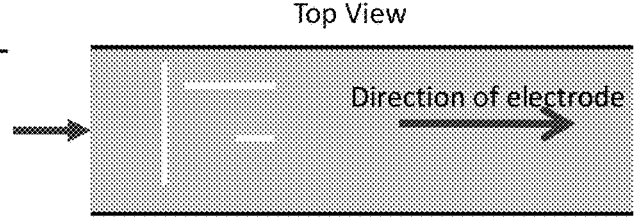
Figure 6L:
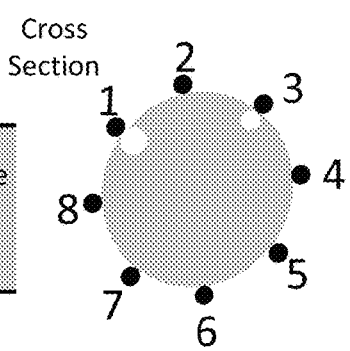
Figure 6M:
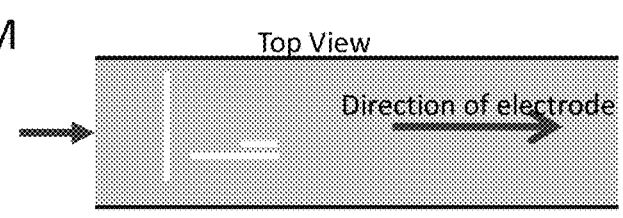
Figure 6M:
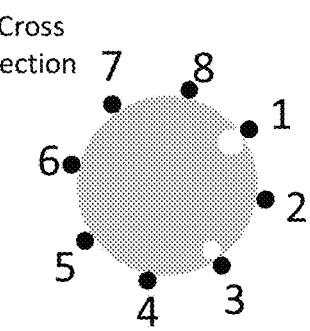

FIG. 6I illustrates how the electrode would look on angiography oriented with conducting wire 1 on top (assuming balloon and wires invisible to scanner); FIG. 6J illustrates the electrode oriented with conducting wire 1 on bottom; FIG. 6K illustrates electrode orientation with conducting wire 1 on right (relative to electrode direction); FIG. 6L illustrates the electrode orientation with conducting wire 1 at 10:30 orientation (relative to electrode direction); and FIG. 6M illustrates how the would look on angiography oriented with conducting wire 1 at 2:30 orientation (relative to electrode direction)—distance measured between the two markers will give the amount of angle electrode.

Determining the proximity of each wire to the restenotic region is possible due to the differences in impedance between restenotic tissue (densely packed disorganized cells) and blood vessel walls (endothelial layer surrounded by connective tissue). In embodiments, a sequence of non-electroporating electrical test pulses (AC or DC) between any one or more, or all, conducting wire pairs around the perimeter of the catheter could be used to determine the extent/depth of restenosis between each pair in real-time while the balloon is inside the tubular body part. This data could then be used to generate a "map" of restenosis depth around the electrode. This data can further be used to generate a protocol for how strong the electrical pulses should be between each wire pair to ablate all of the restenosis for that portion of the vessel. In other words, greater restenosis depth between electrode pairs would have a greater change in properties, which would guide the practitioner to use higher voltages for that pair to ensure ablation of the entire depth, while areas without as much depth would warrant electrical pulses of lower voltage(s). Accordingly, a machine/program could be used to automatically customize pulse parameters for each pair based on restenosis geometry.

In one embodiment, the treatment control module 54 has been programmed to display on the display device 11 a graphical representation of the stenosis and a graphical representation and identification of the electrodes (e.g., electrode numbers) in positional relationship to the stenosis. Graphically, the image would be similar to that shown in FIG. 2B, except the electrodes would be numbered such that a user would be able to judge for himself which electrodes are closest to the stenosis site as well as the depth of the stenosis for each pair of electrodes. After displaying the graphical images, the treatment control module 54 would then select the proper electrodes pairs to energize and the electrical parameters for the selected pair as the protocol. For example, in FIG. 2B, assume that electrodes starting from the one at 12 o'clock position, clock-wise, are numbered 1 through 8. In that case, the selected electrodes may be pair 0-1, 1-2, 2-3 and 3-4. The selected voltages for the pairs may be 500 V/cm for pairs 0-1 and 3-4, and 1200 V/cm for pairs 1-2 and 2-3. Alternatively, the voltage may be the same for all selected pairs, but the number of pulse repetition may be greater for pairs 1-2 and 2-3 since a larger ablation region can be obtained with a larger number of pulses applied. Alternatively, the pulse duration may be greater for pairs 1-2 and 2-3. The treatment control module 54 then displays on the display device 11 the determined protocol for the user to change or accept. The treatment control module 54 allows the user to change the electrode pairs and other electrical parameters such as voltage, pulse duration and number of repetition for each pair. Preferably, each pulse is a biphasic pulse. To ensure that the thermal damage, if any, is minimized, the treatment control module 54 may apply a few pulses to one pair, apply some pulses to another pair, and then come back to the original pair to apply remaining pulses.

For example, the module 54 may control the switch to electrically energize pair 0-1 for 10 times, 3-4 for 10 times, 1-2 for 10 times, 2-3 for 10 times, and then repeat the same pattern for 10 times for a total number of 100 repetition for each electrode pair.

Even in such an embodiment, it is preferred to have 2-3 radio-opaque markers as well as at least one intravascular ultrasound marker included, especially in cases where a catheter style electrode is used for applications beyond restenosis ablation, such as a minimally invasive method for targeting ablation/Electrochemotherapy/gene transfer in a region of tissue between two vessels. In such a protocol, one catheter style electrode can be inserted into a first vessel and a second catheter style electrode is inserted into a second vessel proximal in location to the first vessel. Targeting the tissue between the vessels for ablation, wire(s) facing each other from each catheter can be energized to target the tissue in this region. Preferably, only the wires facing each other are energized so that surrounding tissue is not affected.

Figure 7:
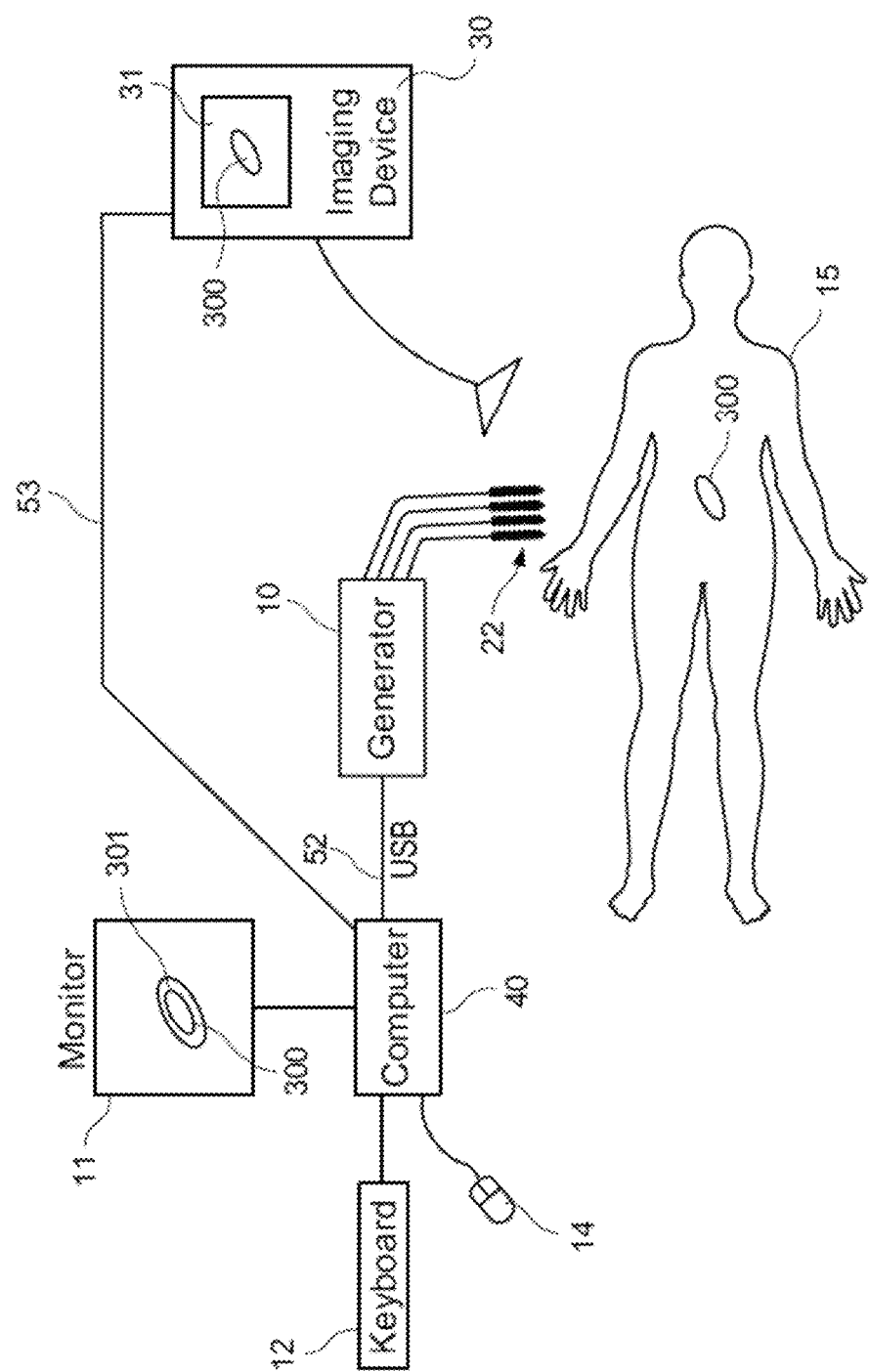
FIG. 7 is a schematic diagram illustrating an IRE system of the invention.

FIG. 7 is a schematic diagram illustrating an IRE system of the invention as disclosed more fully in PCT Patent Application No. PCT/US10/29243, filed Mar. 30, 2010 and entitled "System and Method for Estimating a Treatment Region for a Medical Treatment Device and for Interactively Planning a Treatment of a Patient", incorporated herein by reference. As illustrated, representative systems can comprise a computer 40 comprising or in operable communication with a computer program embodied in a computer-readable storage medium, which program when executed, enables the computer to operate an IRE medical device. The computer 40 is in operable communication with a mouse 14, keyboard 12, and monitor 11 to enable a user to operate the IRE system. Optionally, computer 40 is in operable communication with one or more imaging modality 30, such as an x-ray, for identifying target tissue in a patient 15 and/or identifying the orientation of electrodes inserted into patient 15. Target tissue 300 (but also inserted electrodes 300) can be viewed on the screen 31 of imaging device 30, as well as on monitor 11. During an IRE procedure, the IRE treatment area 301 can be viewed on monitor 11. Computer 40 is also in operable communication with an electrical pulse generator 10, which in turn is in operable communication with electrodes 22. Any electrical connection between components of the system can be used, as for example a USB connection can be used to connect the computer 40 with electrical charge generator 10.

In specific embodiments, an intravascular IRE system is provided comprising: one or more intravascular catheter type electrode 22 having an inflatable balloon and a plurality of electrically conductive wires disposed lengthwise along the electrode and circumferentially spaced a selected distance from one another; an electrical pulse generator 10 in operable communication with and for delivering electrical pulses to the plurality of electrically conductive wires of the electrodes 22; and a control system 40, 30 in operable communication with the electrical pulse generator 10 comprising a computer program embodied in a computer-readable storage medium, which program when executed, enables a computer 40 to perform a method comprising: determining orientation of the wires of the electrode relative to target tissue 300; selecting one or more but less than all of the electrically conductive wires for administering the electrical pulse(s); and energizing the selected wires to deliver the electrical pulse(s) to the target tissue 300.

Figure 8:
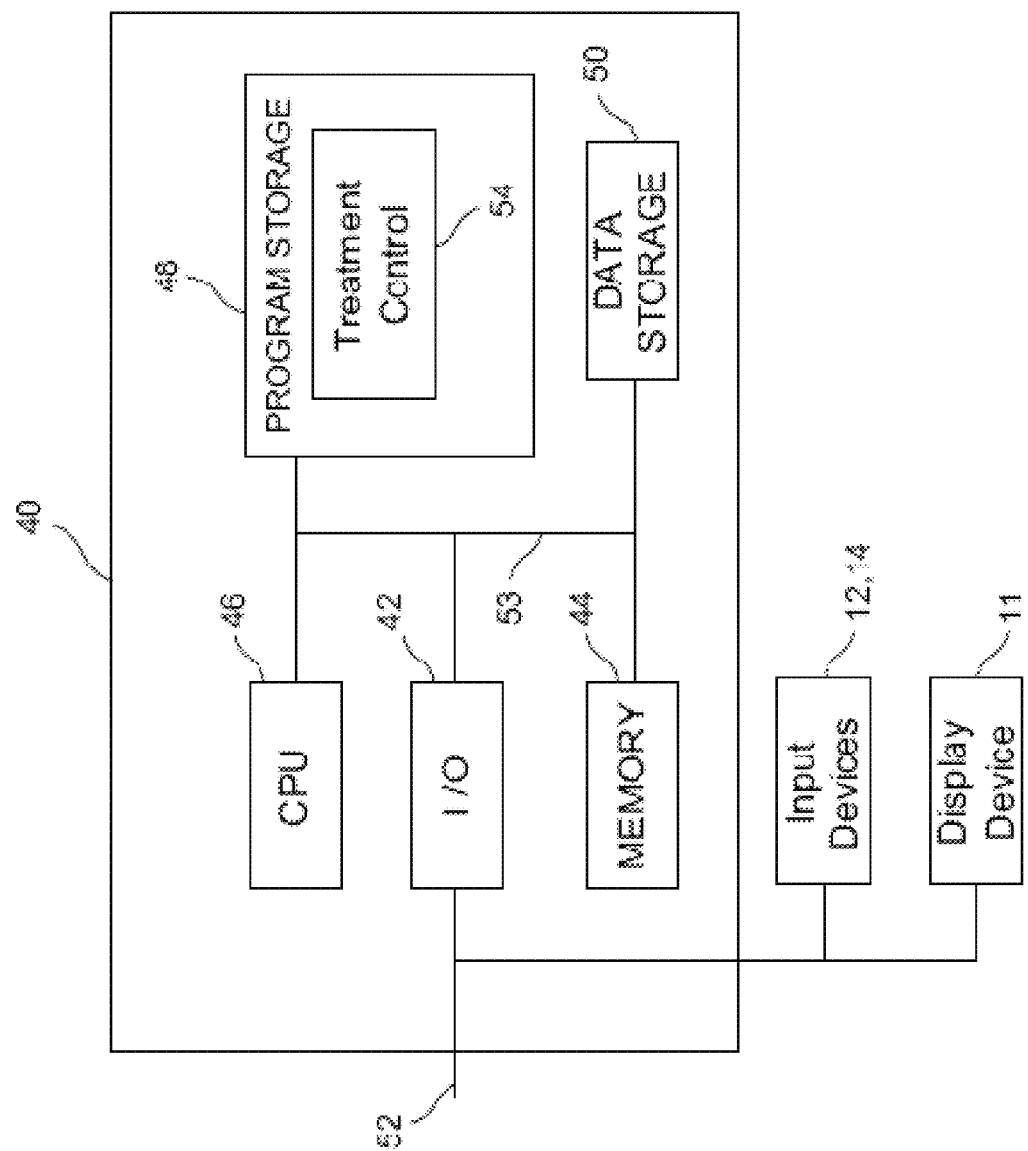
FIG. 8 is a schematic diagram illustrating a control system for implementing methods of the invention and/or operating systems and devices of the invention.

FIG. 8 is a schematic diagram illustrating a control system for implementing methods of the invention and/or operating systems and devices of the invention. Representative embodiments of control systems 40 of the invention can include a computer or computer system with a central processing unit (CPU) 46. The computer system 46 is in operable communication with a power source 52 for supplying electrical power to run the computer, which power supply is controlled using an on/off switch 42. The CPU 46 is operationally connected with one or more computer programs 48 for operating an IRE device or system of the invention. The computer program 48 can comprise instructions 54 for implementing treatment procedures of the invention. By way of connection 53, CPU 46 is in operable communication with memory 44 and one or more data storage device 50. Together, the CPU 46, memory 44, and data storage 50 run computer program(s) 48/54 to operate IRE systems or devices of the invention according to one or more of the methods described in this specification. One or more input devices 12, 14 are in operable communication with the computer system 40 to provide information needed for implementing the treatment protocols. For example, input devices 12, 14 could include one or more imaging modalities to provide information to the practitioner about the target region of interest of a patient, such as shape and size of a tumor or restenosis, or information about the orientation of an electrode in a patient, especially with respect to orientation of certain electrically conductive wires of the electrode relative to a target region of interest. The imaging modalities can include for example MRI, CT, or x-ray. Another such input device 12, 14 could include sensors for collecting information about the tissue being treated, such as current or conductance information. One or more display device 11, such as a monitor, can also be operationally connected with systems of the invention for the practitioner to be able to view the target region of interest and/or positioning or orientation of electrodes in a patient.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. Other embodiments of the invention will be apparent to those skilled in the art from consideration of the specification and practice of the invention.

For example, the device and method described herein may be used to treat other types of lesions such as aneurysm of a blood vessel.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method for treating a target lesion by irreversible electroporation comprising:
    positioning a plurality of elongated electrodes disposed lengthwise and circumferentially spaced a selected distance from one another at the target lesion;
    selecting any combination of electrodes among the plurality of electrodes for administering a plurality of electrical pulses; and
    activating a generator to administer the plurality of electrical pulses through only the selected electrodes to the target lesion in an amount which is sufficient to induce irreversible electroporation of cells of the target lesion, wherein at least one of the electrical pulses is applied with a pulse duration of from 1 µs to 1 ms, wherein at least one of the electrical pulses is applied to a first pair of electrodes comprising a first electrode and a second electrode separated by at least one unenergized electrode, wherein the administration of the plurality of electrical pulses through only the selected electrodes treats tissue proximate the energized electrodes while tissue proximate the un-energized electrodes is substantially untreated.

2. The method of claim 1, wherein the plurality of electrical pulses is administered by sequentially activating different pairs of electrodes.

3. The method of claim 1, wherein the plurality of electrical pulses is administered in a manner such that a different voltage is applied to different pairs of electrodes.

4. The method of claim 1, wherein the plurality of electrical pulses is administered in a manner that provides for an electric field distribution ranging from about 5 to 5,000 V/cm.

5. The method of claim 1, wherein the activating of the generator includes controlling a switch to select at least one electrode to which the electrical pulses are not to be applied.

6. The method of claim 1, further comprising determining at least one individualized electrical parameter for a pair of electrodes.

7. The method of claim 1, wherein the positioning is determined by applying test pulses and measuring at least one electrical characteristic of tissue cells.

8. The method of claim 7, wherein the positioning includes measuring an electrical resistance as the at least one electrical characteristic of the tissue cells.

9. The method of claim 1, wherein the administration of the electrical pulses includes:
applying a first set of pulses between the first pair of electrodes, wherein the first set of pulses is less than a total number of pulses to be applied between the first and second electrodes; and
applying a second set of pulses between a second pair of electrodes, wherein the second set of pulses is less than a total number of pulses to be applied between the second pair of electrodes.

10. The method of claim 9, wherein the administration of the electrical pulses further includes repeating application of sets of pulses between the first and second electrodes followed by sets of pulses between the second pair of electrodes until the total number of pulses is reached.

11. The method of claim 1, wherein the target lesion is asymmetric.

12. A method for treating a target lesion by irreversible electroporation comprising:
positioning a plurality of elongated electrodes disposed lengthwise and circumferentially spaced a selected distance from one another at the target lesion; and
activating a generator to administer a plurality of electrical pulses through only selected electrodes to the target lesion in an amount which is sufficient to induce non-thermal ablation of cells of the target lesion, wherein at least one of the electrical pulses is applied with a pulse duration of from 1 µs to 1 ms,
wherein the selected electrodes includes a number of electrodes less than a total number of electrodes in the plurality of elongated electrodes,
wherein the selected electrodes includes at least a first electrode and a second electrode separated by at least one unenergized electrode, and
wherein the administration of the plurality of electrical pulses through only the selected electrodes treats tissue proximate the energized electrodes while tissue proximate the un-energized electrodes is substantially untreated.

13. The method of claim 12, wherein the plurality of electrical pulses is administered by sequentially activating different pairs of electrodes.

14. The method of claim 12, wherein the plurality of electrical pulses is administered by activating pairs of electrodes positioned in a manner capable of treating the target lesion.

15. The method of claim 12, wherein the plurality of electrical pulses is administered in a manner that provides for an electric field distribution ranging from about 5 to 5,000 V/cm.

16. The method of claim 12, wherein the activating of the generator includes controlling a switch to select at least one electrode to which the electrical pulses are not to be applied.

17. The method of claim 12, further comprising:
determining at least one individualized electrical parameter for a pair of electrodes.

18. The method of claim 12, wherein the positioning is determined by applying test pulses and measuring at least one electrical characteristic of tissue cells.

19. The method of claim 18, wherein the positioning includes measuring an electrical resistance as the at least one electrical characteristic of the tissue cells.

* * * * *